(12) United States Patent
Tsuzuki et al.

(10) Patent No.: US 9,518,863 B2
(45) Date of Patent: Dec. 13, 2016

(54) ELASTIC WAVE ELEMENT AND ELASTIC WAVE SENSOR USING SAME

(71) Applicant: Panasonic Intellectual Property Management Co., Ltd., Osaka (JP)

(72) Inventors: Shigeru Tsuzuki, Osaka (JP);
Kazunori Nishimura, Kyoto (JP);
Hiroyuki Nakamura, Osaka (JP);
Tomohiro Iwasaki, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 196 days.

(21) Appl. No.: 14/414,792

(22) PCT Filed: Oct. 1, 2013

(86) PCT No.: PCT/JP2013/005836
§ 371 (c)(1),
(2) Date: Jan. 14, 2015

(87) PCT Pub. No.: WO2014/054269
PCT Pub. Date: Apr. 10, 2014

(65) Prior Publication Data
US 2015/0168209 A1    Jun. 18, 2015

(30) Foreign Application Priority Data

Oct. 1, 2012 (JP) ................. 2012-219119
Oct. 24, 2012 (JP) ................. 2012-234395
(Continued)

(51) Int. Cl.
*G01H 17/00* (2006.01)
*G01D 5/12* (2006.01)
(Continued)

(52) U.S. Cl.
CPC ............. *G01H 17/00* (2013.01); *B06B 1/0622* (2013.01); *G01D 5/12* (2013.01); *G01N 29/022* (2013.01);
(Continued)

(58) Field of Classification Search
CPC ............ H03H 9/02637; H03H 9/14505; H03H 9/1455; H03H 9/02787; G01N 29/022; G01N 33/5438; G01N 29/036; G01N 2291/011; G01N 2291/015; G01N 2291/0255; G01N 2291/0256; G01N 2291/0423; G01D 5/12; G01H 17/00; B06B 1/0622
(Continued)

(56) References Cited

U.S. PATENT DOCUMENTS 5,365,206 A    11/1994    Machui et al.
5,646,584 A    7/1997    Kondratyev et al.
(Continued)

FOREIGN PATENT DOCUMENTS

EP    924857    6/1999
JP    1-305318    12/1989
(Continued)

OTHER PUBLICATIONS

The Extended European Search Report dated Nov. 16, 2015 for the related European Patent Application No. 13843163.0.
(Continued)

*Primary Examiner* — J M Saint Surin
(74) *Attorney, Agent, or Firm* — McDermott Will & Emery LLP

(57) ABSTRACT

An acoustic wave element includes a piezoelectric substrate, an excitation electrode configured to excite and output a main acoustic wave on the piezoelectric substrate, a receiving electrode configured to receive the main acoustic wave,
(Continued)

a propagation path configured to allow the main acoustic wave to propagate along the piezoelectric substrate between the excitation electrode and the receiving electrode, and a sensing portion configured to react to an object substance. The propagation path is configured to allow the main acoustic wave to pass plural times through the sensing portion along the propagation path. This acoustic wave element has high sensitivity to the object substance.

50 Claims, 29 Drawing Sheets

(30) Foreign Application Priority Data

Nov. 20, 2012 (JP) .................. 2012-253976
Nov. 20, 2012 (JP) .................. 2012-253977

(51) Int. Cl.
| | |
|---|---|
| H03H 9/02 | (2006.01) |
| H03H 9/145 | (2006.01) |
| G01N 33/543 | (2006.01) |
| B06B 1/06 | (2006.01) |
| G01N 29/02 | (2006.01) |
| G01N 29/036 | (2006.01) |

(52) U.S. Cl.
CPC ........ *G01N 29/036* (2013.01); *G01N 33/5438* (2013.01); *H03H 9/02637* (2013.01); *H03H 9/02787* (2013.01); *H03H 9/1455* (2013.01); *H03H 9/14505* (2013.01); *G01N 2291/011* (2013.01); *G01N 2291/015* (2013.01); *G01N 2291/0255* (2013.01); *G01N 2291/0256* (2013.01); *G01N 2291/0423* (2013.01)

(58) Field of Classification Search
USPC ........................................... 73/632
See application file for complete search history.

(56) References Cited

U.S. PATENT DOCUMENTS

| 5,663,696 | A | 9/1997 | Morgan |
| 5,670,920 | A | 9/1997 | Morgan |
| 6,104,260 | A | 8/2000 | Yamada et al. |
| 9,136,458 | B2* | 9/2015 | Komatsu ............ H03H 9/02818 |
| 9,322,809 | B2* | 4/2016 | Komatsu .............. G01N 29/022 |
| 2002/0105392 | A1* | 8/2002 | Fujii .................. H03H 9/14505 |
| | | | 333/193 |
| 2002/0163402 | A1 | 11/2002 | Tsuzuki et al. |
| 2009/0028001 | A1 | 1/2009 | Andle et al. |
| 2012/0073390 | A1 | 3/2012 | Zaghloul et al. |
| 2012/0146457 | A1 | 6/2012 | Goto et al. |
| 2013/0009517 | A1 | 1/2013 | Do et al. |
| 2013/0335170 | A1* | 12/2013 | Ikuta ................... H03H 9/0296 |
| | | | 333/193 |

FOREIGN PATENT DOCUMENTS

| JP | 7-297669 | | 11/1995 |
| JP | 11-186865 | | 7/1999 |
| JP | 2003-234637 | | 8/2003 |
| JP | 2006-258767 | | 9/2006 |
| JP | 2008-122105 | | 5/2008 |
| JP | 2012-085108 | | 4/2012 |
| WO | 01/43284 | | 6/2001 |
| WO | 2010/082266 | | 7/2010 |
| WO | WO2010082266 | * | 7/2010 |
| WO | 2011/030519 | | 3/2011 |

OTHER PUBLICATIONS

Bergmann A et al: "Two-track-reflector-filters for CDMA mobile telephones", Ultrasonics Symposium, 1996. Proceedings., 1996 IEEE San Antonio, TX, USA Nov. 3-6, 1996, IEEE, New York, NY, USA, vol. 1, Nov. 3, 1996 (Nov. 3, 1996), pp. 57-60.
Dill R et al: "A novel SAW filter for IF-filtering in DECT systems", Ultrasonics Symposium, 1995. Proceedings., 1995 IEEE Seattle, WA, USA Nov. 7-10, 1995, New York, NY, USA, IEEE, US, vol. 1, Nov. 7, 1995 (Nov. 7, 1995), pp. 51-54.
Machui J et al: "Z-path IF-filters for mobile telephones", Ultrasonics Symposium, 1992. Proceedings., IEEE 1992 Tucson, AZ, USA Oct. 20-23, 1992, New York, NY, USA, IEEE, US, Oct. 20, 1992 (Oct. 20, 1992), pp. 147-150.
International Search Report of PCT application No. PCT/JP2013/005836 dated Dec. 3, 2013.

* cited by examiner

ELASTIC WAVE ELEMENT AND ELASTIC WAVE SENSOR USING SAME

This application is a U.S. national stage application of the PCT international application No. PCT/JP2013/005836 filed on Oct. 1, 2013, which claims the benefit of foreign priority of Japanese patent applications 2012-219119 filed on Oct. 1, 2012, 2012-234395 filed on Oct. 24, 2012, 2012-253977 filed on Nov. 20, 2012, and 2012-253976 filed on Nov. 20, 2012, the contents all of which are incorporated herein by reference.

TECHNICAL FIELD

The present invention relates to an acoustic wave element having a sensing portion that reacts to an object substance or to which an object substance is attached, and relates to an acoustic wave sensor using the acoustic wave element.

BACKGROUND ART

FIG. 28 is a schematic top view of conventional acoustic wave element 501 disclosed in PTL 1. Acoustic wave element 501 includes piezoelectric substrate 502, excitation electrode 503, and receiving electrode 504 formed on piezoelectric substrate 502, dielectric layer 506 formed on piezoelectric substrate 502 for covering excitation electrode 503 and receiving electrode 504, sensing portion 505, and a detector. Sensing portion 505 is formed on piezoelectric substrate 502 and above a propagation path of main acoustic wave 507 between excitation electrode 503 and the receiving electrode 504. The detector detects characteristics of main acoustic wave 507 excited by excitation electrode 503.

Characteristics, such as a frequency and a phase, of main acoustic wave 507 change upon sensing portion 505 contacting a test substance, such as expired air or test liquid, that may possibly contain an object substance. The detector detects the change in the characteristics, and senses, e.g. a presence or a concentration of the object substance.

Conventional acoustic wave element 501 may not ensure sensitivity of sensing portion 505.

CITATION LIST

Patent Literature

PTL 1: International Publication No. WO2011/030519

SUMMARY

An acoustic wave element includes a piezoelectric substrate, an excitation electrode provided on the piezoelectric substrate and configured to excite and output a main acoustic wave, a receiving electrode configured to receive the main acoustic wave, a propagation path configured to allow the main acoustic wave to propagate along the piezoelectric substrate between the excitation electrode and the receiving electrode, and a sensing portion configured to react to an object substance. The propagation path is configured to allow the main acoustic wave to pass through the sensing portion along the propagation path plural times.

This acoustic wave element has high sensitivity to the object substance.

DETAIL DESCRIPTION OF PREFERRED EMBODIMENTS

Exemplary Embodiment 1

Figure 1:
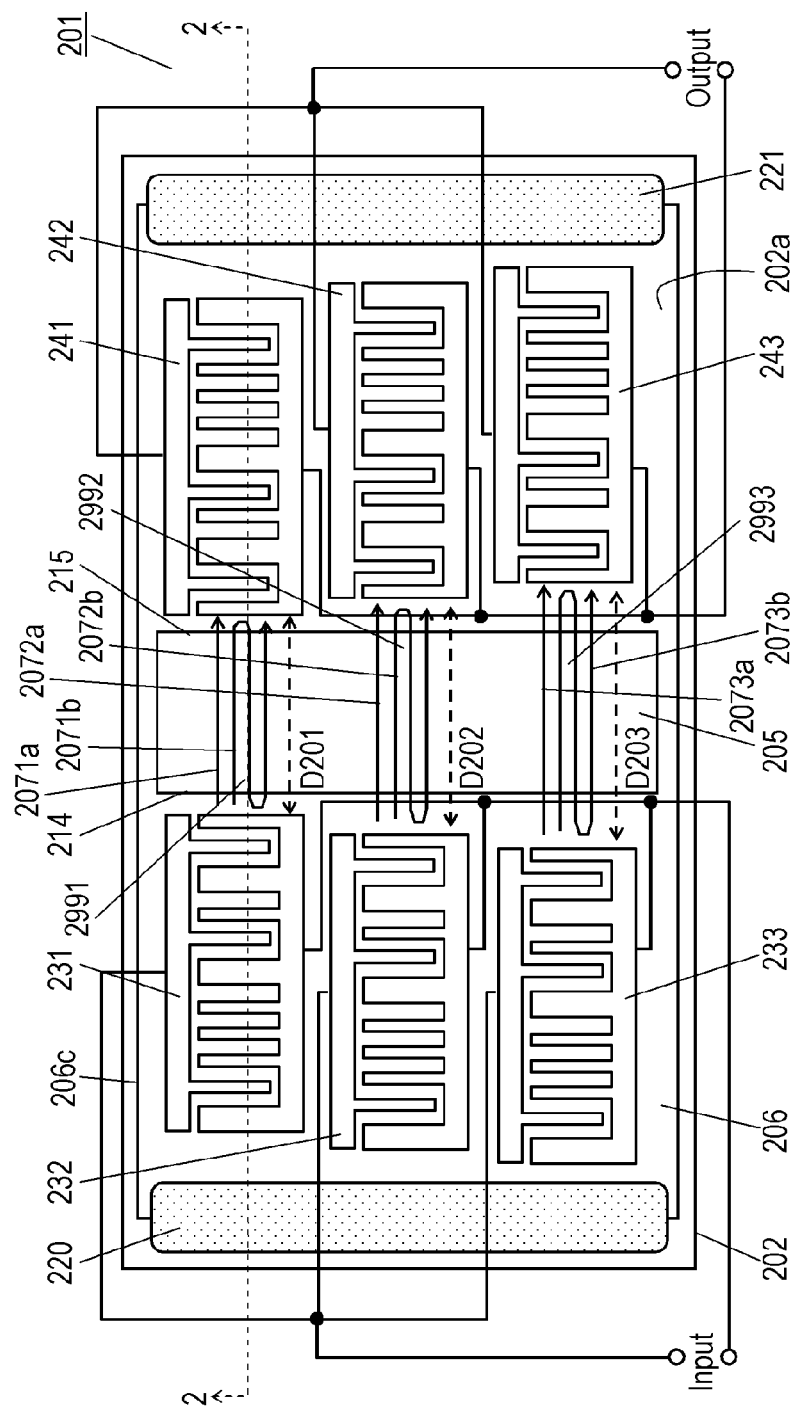
FIG. 1 is a schematic top view of an acoustic wave element according to Exemplary Embodiment 1 of the present invention.

FIG. 1 is a schematic top view of acoustic wave element 201 according to Exemplary Embodiment 1. Acoustic wave element 201 is a transversal type acoustic wave element, and is applicable to an acoustic wave sensor that senses an object substance, such as a protein, a gene, or a signal molecule, based on a biomolecule recognition mechanism.

Acoustic wave element 201 includes piezoelectric substrate 202 and excitation electrodes 231, 232, and 233 provided on upper surface 202a of piezoelectric substrate 202. Excitation electrodes 231, 232, and 233 respectively excite main acoustic waves 2071a, 2072a, and 2073a upon receiving a signal input thereto. Excitation electrodes 231, 232, and 233 are connected in parallel to each other.

Acoustic wave element 201 further includes receiving electrodes 241, 242, and 243 provided on upper surface 202a of piezoelectric substrate 202. Receiving electrodes 241, 242, and 243 receive main acoustic waves 2071a, 2072a, and 2073a output from excitation electrodes 231, 232, and 233, respectively. Receiving electrodes 241, 242, and 243 output signals in response to the received main acoustic waves 2071a, 2072a, and 2073a, respectively. Excitation electrode 231 further excites main acoustic wave 2071b to be received by receiving electrode 241 after being reflected by receiving electrode 241 and further reflected by excitation electrode 231. Excitation electrode 232 further excites main acoustic wave 2072b to be received by receiving electrode 242 after being reflected by receiving electrode 242 and further reflected by excitation electrode 232. Excitation electrode 233 further excites main acoustic wave 2073b to be received by receiving electrode 243 after being reflected by receiving electrode 243 and further reflected by excitation electrode 233. Receiving electrode 241 outputs output signals in response to main acoustic waves 2071a and 2071b output from excitation electrode 231. Receiving electrode 242 outputs output signals corresponding to main acoustic waves 2072a and 2072b output from excitation electrode 232. Receiving electrode 243 outputs output signals corresponding to main acoustic waves 2073a and 2073b output from excitation electrode 233. Receiving electrodes 241, 242, and 243 are connected in parallel to each other.

In acoustic wave element 201, propagation path 2991 along which main acoustic waves 2071a and 2071b propagate is formed between excitation electrode 231 and receiving electrode 241. Propagation path 2992 along which main acoustic waves 2072a and 2072b propagate is formed between excitation electrode 232 and receiving electrode 242. Propagation path 2993 along which main acoustic waves 2073a and 2073b propagate is formed between excitation electrode 233 and receiving electrode 243.

Excitation electrodes 231, 232, and 233 and receiving electrodes 241, 242, and 243 are disposed such that the signal in response to main acoustic wave 2071a output from excitation electrode 231 and directly input to receiving electrode 241, the signal in response to main acoustic wave 2072a output from excitation electrode 232 and directly input to receiving electrode 242, and the signal of main acoustic wave 2073a output from excitation electrode 233 and directly input to receiving electrode 243 are added so as to cancel each other.

Further, excitation electrodes 231, 232, and 233 and receiving electrodes 241, 242, and 243 are disposed such that the signal in response to main acoustic wave 2071b input to receiving electrode 241 after propagating along propagation path 2991 between excitation electrode 231 and receiving electrode 241 predetermined times, the signal in response to main acoustic wave 2072b input to receiving electrode 242 after propagating along propagation path 2992 between excitation electrode 232 and receiving electrode 242 predetermined times, and the signal in response to main acoustic wave 2073b input to receiving electrode 243 after propagating along propagation path 2993 between excitation electrode 233 and receiving electrode 243 predetermined times are added so as to strengthen each other.

Figure 2:
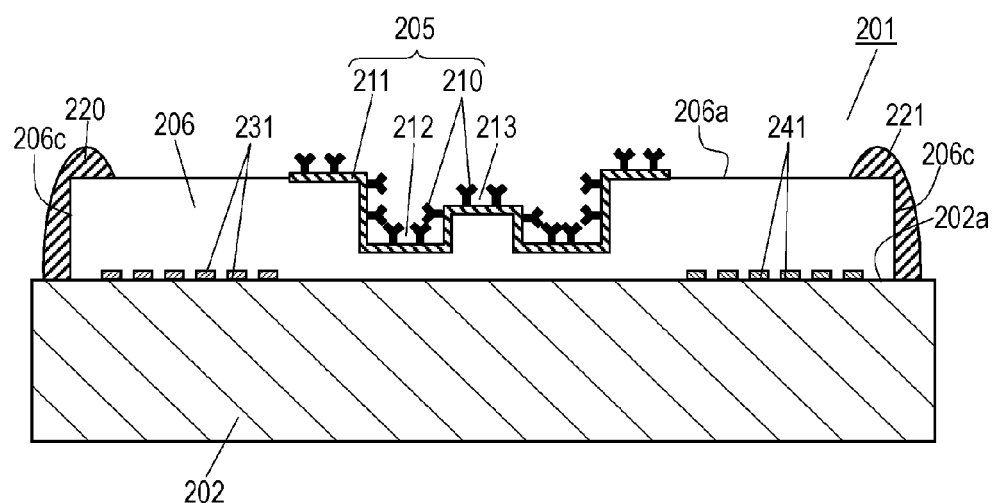
FIG. 2 is a schematic sectional view of the acoustic wave element at line 2-2 shown in FIG. 1.

FIG. 2 is a sectional view of acoustic wave element 201 at line 2-2 along propagation path 2991 illustrated in FIG. 1. Acoustic wave element 201 further includes dielectric layer 206 provided on upper surface 202a of piezoelectric substrate 202, and sensing portion 205 provided on upper surface 206a of dielectric layer 206. Sensing portion 205 is provided on upper surface 206a of dielectric layer 206 above propagation paths 2991 to 2993, and is configured to react to an object substance or a binding material to be bound with the object substance, or such that the object substance or the binding material is attached thereon.

Figure 3:
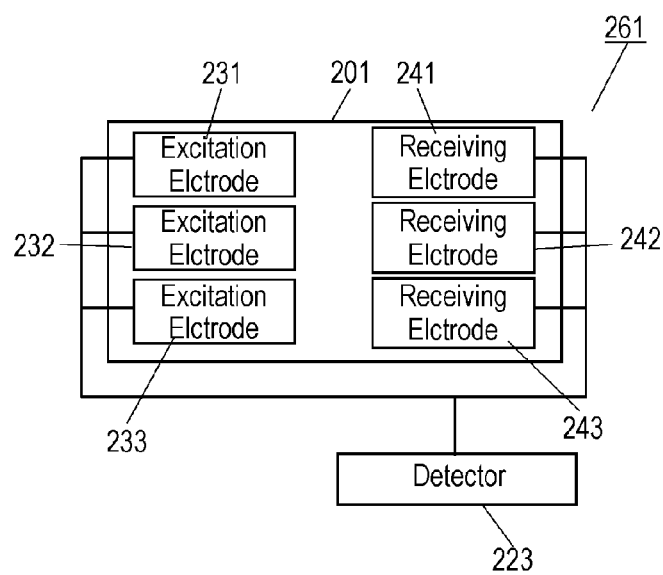
FIG. 3 is a schematic view of the acoustic wave sensor according to Embodiment 1.

FIG. 3 is a schematic view of acoustic wave sensor 261 using acoustic wave element 201. Acoustic wave sensor 261 includes acoustic wave element 201 and detector 223 that receives a combined signal obtained by adding the signals output from receiving electrodes 241, 242, and 243. Detector 223 detects characteristics, such as delay time characteristics, phase characteristics, or amplitude characteristics, of main acoustic waves 2071b, 2072b, and 2073b received by receiving electrodes 241, 242, and 243. Detector 223 is electrically connected to excitation electrodes 231, 232, and 233.

Acoustic wave element 201 is mounted on a mother board built in an electronic device, such as various medical devices. Acoustic wave element 201 may be mounted face down on the mother board, such that a surface of piezoelectric substrate 202 on which electrodes 231 to 233 and 241 to 243 faces the mother board. In this case, receiving electrodes 241 to 243 are electrically connected to detector 223 via, e.g. metal bumps. Acoustic wave element 201 may be mounted face up on the mother board such that a surface opposite to the surface on which electrodes 231 to 233 and 241 to 243 are provided is bonded to the mother board. In this case, receiving electrodes 241 to 243 are electrically connected to detector 223 via, e.g. metal wires.

Upon a test substance, such as expired air or test liquid, which possibly contains an object substance contacting sensing portion 205, the object substance is attached to sensing portion 205 changes a physical amount, such as a mass, of sensing portion 205. Detector 223 can detect a change in the characteristics of main acoustic waves 2071b, 2072b, and 2073b due to the change in the physical amount of sensing portion 205, and thus can sense a presence or a concentration of the object substance.

Figure 28:
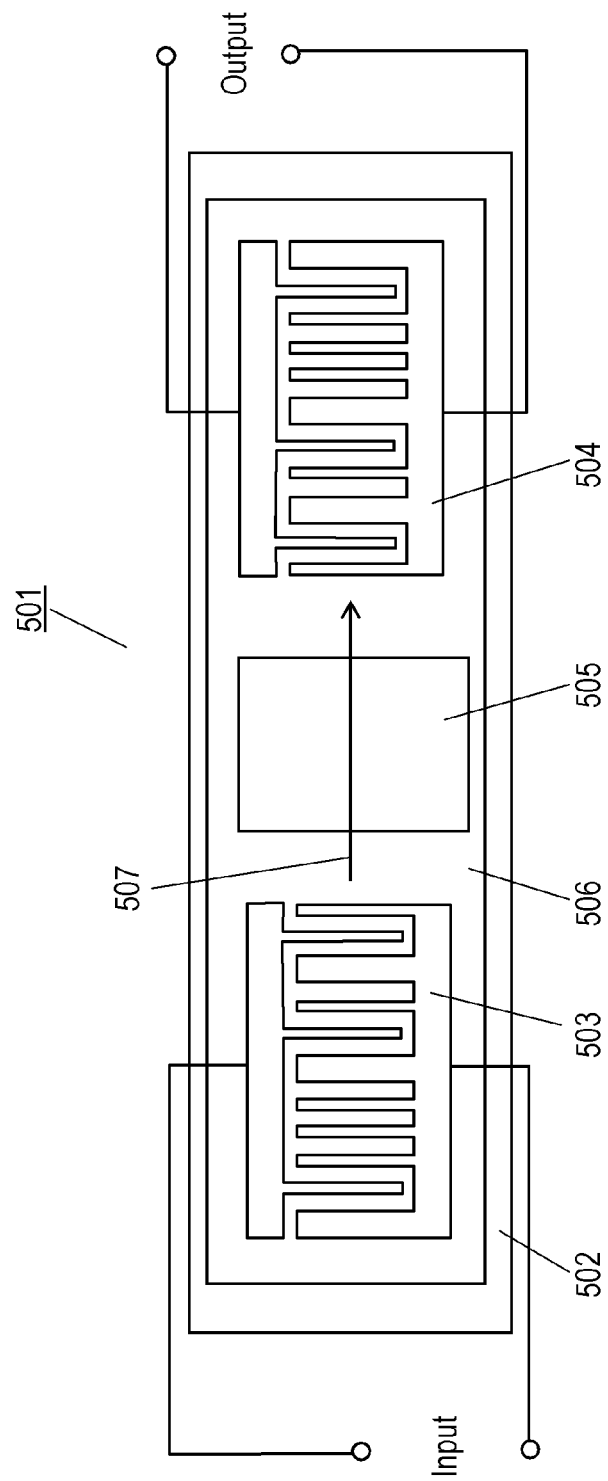
FIG. 28 is a schematic top view of a conventional acoustic wave element.

In conventional acoustic wave element 501 illustrated in FIG. 28, main acoustic wave 507 excited by excitation electrode 503 propagates across sensing portion 505 above a propagation path only once and then reaches receiving electrode 504. Therefore, a characteristic, such as a delay time characteristic or a phase characteristic, of main acoustic wave 507 may not change sufficiently even when an object substance is attached, and may not ensure a sensitivity of sensing portion 505 of acoustic wave element 501.

In acoustic wave element 201 illustrated in FIG. 1, main acoustic waves 2071b, 2072b, and 2073b output from excitation electrodes 231, 232, and 233, reflected by receiving electrodes 241, 242, and 243, reflected by excitation electrodes 231, 232, and 233, and then input back to receiving electrodes 241, 242, and 243 are added so as to strengthen each other. Main acoustic waves 2071b, 2072b, and 2073b pass through sensing portion 205 plural times along propagation paths 2991, 2992, and 2993, and then, reach receiving electrodes 241, 242, and 243, respectively. Accordingly, the characteristics of main acoustic waves 2071b, 2072b, and 2073b changes sufficiently when the object substance or the binding material to be bound with the object substance is attached to sensing portion 205, and thus, can improve a sensitivity of sensing portion 205 of acoustic wave element 201.

Dielectric layer 206 may be preferably disposed on upper surface 202a of piezoelectric substrate 202 and cover at least excitation electrodes 231, 232, and 233 and receiving electrodes 241, 242, and 243. This configuration suppresses corrosion of electrodes 231 to 233 and 241 to 243 due to a solvent containing the object substance, as well as deterioration of sensitivity of acoustic wave sensor 261 including acoustic wave element 201 subjected to the corrosion.

Sensing portion 205 has outer edges 214 and edge 215. Outer edge 214 faces excitation electrodes 231, 232, and 233 while outer edge 215 faces receiving electrodes 241, 242, and 243 viewing from above. Outer edges 214 and 215 of sensing portion 205 are positioned on propagation paths 2991 to 2993. Dielectric layer 206 may preferably further cover propagation paths 2991 to 2993 and sensing portion 205 provided on upper surface 206a of dielectric layer 206 above propagation paths 2991 to 2993. This configuration can suppress reflection of main acoustic waves 2071b, 2072b, and 2073b due to outer edges 214 and 215 of sensing portion 205 on propagation paths 2991 to 2993 between excitation electrodes 231 to 233 and receiving electrodes 241 to 243, and improves sensitivity of acoustic wave sensor 261 including acoustic wave element 201. Sensing portion 205 may be provided on piezoelectric substrate 202 above propagation paths 2991 to 2993.

Components of acoustic wave element 201 will be detailed.

Piezoelectric substrate 202 is made of a piezoelectric single crystal substrate, such as a crystal piezoelectric substrate, a langasite-based piezoelectric substrate, a lithium niobate-based piezoelectric substrate, a lithium tantalite-based piezoelectric substrate, or a potassium niobate-based piezoelectric substrate.

Each of excitation electrodes 231, 232, and 233 and receiving electrodes 241, 242, and 243 is an interdigital transducer (IDT) electrode including a pair of comb-shaped electrodes each including plural electrode fingers that interdigitate with each other, and excites or receives main acoustic waves (2071a to 2073a, and 2071b to 2073b), such as shear horizontal (SH) waves and Rayleigh waves. Electrodes 231 to 233 and 241 to 243 are made of, e.g. a single metal such as aluminum, copper, silver, gold, titanium, tungsten, platinum, molybdenum, or chromium, or an alloy composed mainly of any of these metals, or a laminated structure of these metals.

Excitation electrodes 231, 232, and 233 may have the same configuration (the same electrode finger pitch, the same electrode finger interdigitating width, and the same electrode finger width). At least the pitches of the electrode fingers of excitation electrodes 231, 232, and 233 may be preferably identical to each other.

Receiving electrodes 241, 242, and 243 may have the same configuration (the same electrode finger pitch, the same electrode finger interdigitating width, and the same electrode finger width). At least the pitches of the electrode fingers of receiving electrodes 241, 242, and 243 may be preferably identical to each other.

The configuration of excitation electrodes 231, 232, and 233 may be symmetrical to that of receiving electrodes 241, 242, and 243 (the same electrode finger pitch, the same electrode finger interdigitating width, and the same electrode finger width). At least the pitches of the electrode fingers of excitation electrodes 231, 232, and 233 may be preferably symmetrical to that of receiving electrodes 241, 242, and 243.

Excitation electrodes 231 to 233 may preferably be unidirectional electrodes that allow main acoustic waves 2071a to 2073a and 2071b to 2073b to propagate in directions toward receiving electrodes 241 to 243 more efficiently than any direction other than the directions toward receiving electrodes 241 to 243, respectively. Receiving electrodes 241 to 243 may preferably be unidirectional electrodes that receive main acoustic waves 2071a to 2073a and 2071b to 2073b in directions from excitation electrodes 231 to 233 more efficiently than any direction other than the directions from excitation electrodes 231 to 233, respectively. This configuration can improve sensitivity of acoustic wave sensor 261 including acoustic wave element 201. In addition, electrodes 231 to 233 and 241 to 243 being the unidirectional electrodes can improve reflection efficiencies of main acoustic waves 2071b to 2073b on excitation electrodes 231 to 233 and receiving electrodes 241 to 243.

The arrangement of excitation electrodes 231, 232, and 233 and receiving electrodes 241, 242, and 243 will be detailed below.

A minimal distance between an electrode finger out of the plural electrode fingers of excitation electrode 231 closest to receiving electrode 241 and an electrode finger out of the plural electrode fingers of receiving electrode 241 closest to excitation electrode 231 is defined as distance D201 between excitation electrode 231 and receiving electrode 241. Similarly, a minimal distance between an electrode finger out of the plural electrode fingers of excitation electrode 232 closest to receiving electrode 242 and an electrode finger out of the plural electrode fingers of receiving electrode 242 closest to excitation electrode 232 is defined as distance D202 between excitation electrode 232 and receiving electrode 242. A minimal distance between an electrode finger out of the plural electrode fingers of excitation electrode 233 closest to receiving electrode 243 and an electrode finger out of the plural electrode fingers of receiving electrode 243 closest to excitation electrode 233 is defined as distance D203 between excitation electrode 233 and receiving electrode 243. Main acoustic waves 2071a to 2073a and 2071b to 2073b received by receiving electrodes 241 to 243 have the same wavelength $\lambda$. A difference between distance D201 between excitation electrode 231 and receiving electrode 241 and distance D202 between excitation electrode 232 and receiving electrode 242 is $2\lambda/3 + n_1 \cdot \lambda$ (where $n_1$ is an integer). A difference between distance D202 between excitation electrode 232 and receiving electrode 242 and distance D203 between excitation electrode 233 and receiving electrode 243 is $\lambda/3 + n_2 \cdot \lambda$ (where $n_2$ is an integer). In other words, a difference between distance D201 between excitation electrode 231 and receiving electrode 241 and distance D203 between excitation electrode 233 and receiving electrode 243 is $2 \cdot \lambda/3 + (n_1 + n_2) \cdot \lambda$. The difference between the distances allows an error of maximum ±λ/36. Integers $n_1$ and $n_2$ are preferably identical to each other, but may be different from each other.

The above arrangement causes phases of main acoustic wave 2071a received by receiving electrode 241 and main acoustic wave 2072a received by receiving electrode 242 to be different from each other by $(120+360 \cdot n_1)$ degrees, and causes phases of main acoustic wave 2072a received by receiving electrode 242 and main acoustic wave 2073a received by receiving electrode 243 to be different from each other by $(120+360 \cdot n_2)$ degrees. Specifically, the phases of main acoustic wave 2071a received by receiving electrode 241 and main acoustic wave 2073a received by receiving electrode 243 are different from each other by $(240+360 \cdot (n_1+n_2))$ degrees. The above phase difference allows an error within a range of ±10 degrees. Therefore, signals in response to main acoustic waves 2071a, 2072a, and 2073a that are directly input to receiving electrodes 241, 242, and 243 after passing only once through propagation paths 2991, 2992, and 2993, respectively, are added so as to cancel each other. On the other hand, the phase difference between a signal in response to main acoustic wave 2071b input to receiving electrode 241 after being reflected by receiving electrode 241 and excitation electrode 231 and passing three times through propagation path 2991, a signal in response to main acoustic wave 2072b input to receiving electrode 242 after being reflected by receiving electrode 242 and excitation electrode 232 and passing three times through propagation path 2992, a signal in response to main acoustic wave 2073b input to receiving electrode 243 after being reflected by receiving electrode 243 and excitation electrode 233 and passing three times through propagation path 2993 ranges from −30 degrees to 30 degrees. Therefore, the signals are added so as to strengthen each other, hence increasing amplitude of a combined signal obtained by adding the signals.

Main acoustic waves 2071b to 2073b producing the signals added so as to strengthen each other propagate three times between outer edges 214 and 215 of sensing portion 205 above propagation paths 2991 to 2993, and then reach receiving electrodes 241 to 243, respectively. Accordingly, when the object substance or the binding material to be bound with the object substance attaches to sensing portion 205, changes in the characteristics due to a change in a physical amount of sensing portion 205 such as a mass change appear three times more clearly. As a result, the characteristics of main acoustic waves 2071b to 2073b, such as delay time characteristics, change sufficiently large, accordingly improving sensitivity of sensing portion 205 of acoustic wave element 201.

Sensing portion 205 includes antibodies 210 and adhesion layer 211 for bonding antibodies 210 to upper surface 202a of piezoelectric substrate 202 or upper surface 106a of dielectric layer 206. Antibodies 210 react to the object substance or the binding material to be bound with the object substance that may possibly contained in the test substance, such as expired air or test liquid. Adhesion layer 211 is made of an adhesive material, such as a metal or an organic substance. Antibody 210 may be directly attached to piezoelectric substrate 202 or dielectric layer 206 without adhesion layer 211 between antibody 210 and piezoelectric substrate 202 or between antibody 210 and dielectric layer 206.

Dielectric layer 206 is made of an inorganic dielectric material, or may be made of a medium, such as silicon oxide ($SiO_2$), having a frequency-temperature coefficient opposite to that of piezoelectric substrate 202. Dielectric layer 206 covers electrodes 231 to 233 and 241 to 243 to improve a frequency-temperature characteristic of acoustic wave element 201. Further, dielectric layer 206 may be made of another dielectric material, such as silicon nitride, silicon nitride oxide, aluminum nitride, aluminum oxide, tantalum oxide, tellurium oxide, diamond, or silicone.

Acoustic wave element 201 may further include acoustic absorbents 220 and 221 provided on upper surface 202a of piezoelectric substrate 202. Acoustic absorbent 220 covers portions of outer edge 206c of dielectric layer 206 opposite to receiving electrodes 241, 242, and 243 with respect to excitation electrodes 231, 232, and 233, respectively. Acoustic absorbent 221 covers portions of outer edge 206c of dielectric layer 206 opposite to excitation electrodes 231, 232, and 233 with respect to receiving electrodes 241, 242, and 243, respectively. Acoustic absorbents 220 and 221 are made of, for example, a resin, such as an epoxy resin, a silicone resin, an acrylic resin, or a polyimide. Excitation electrodes 231, 232, and 233 produces unnecessary acoustic waves in a direction opposite to a propagation direction in which desired acoustic waves directed from excitation electrodes 231, 232, and 233 toward receiving electrodes 241, 242, and 243 propagate. Acoustic absorbents 220 and 221 prevent sensitivity of acoustic wave sensor 261 from deteriorating due to the unnecessary acoustic waves which are reflected by outer edge 206c of dielectric layer 206, again propagate to excitation electrodes 231, 232, and 233, and are added to the desired acoustic waves. In this manner, acoustic absorbents 220 and 221 covering outer edge 206c of dielectric layer 206 can absorb the unnecessary acoustic waves and prevent the deterioration in sensitivity.

As illustrated in FIG. 2, upper surface 206a of dielectric layer 206 may preferably be uneven to have recess 212 or projection 213 at an upper surface of adhesion layer 211 that constitutes sensing portion 205. Antibodies 210 may be disposed in recess 212 having a width wider than a maximum width of antibody 210. Recess 212 or projection 213 may be formed by etching predetermined positions on dielectric layer 206 by, e.g. dry etching after dielectric layer 206 is formed on upper surface 202a of piezoelectric substrate 202 by, e.g. sputtering or vapor deposition.

Figure 4:
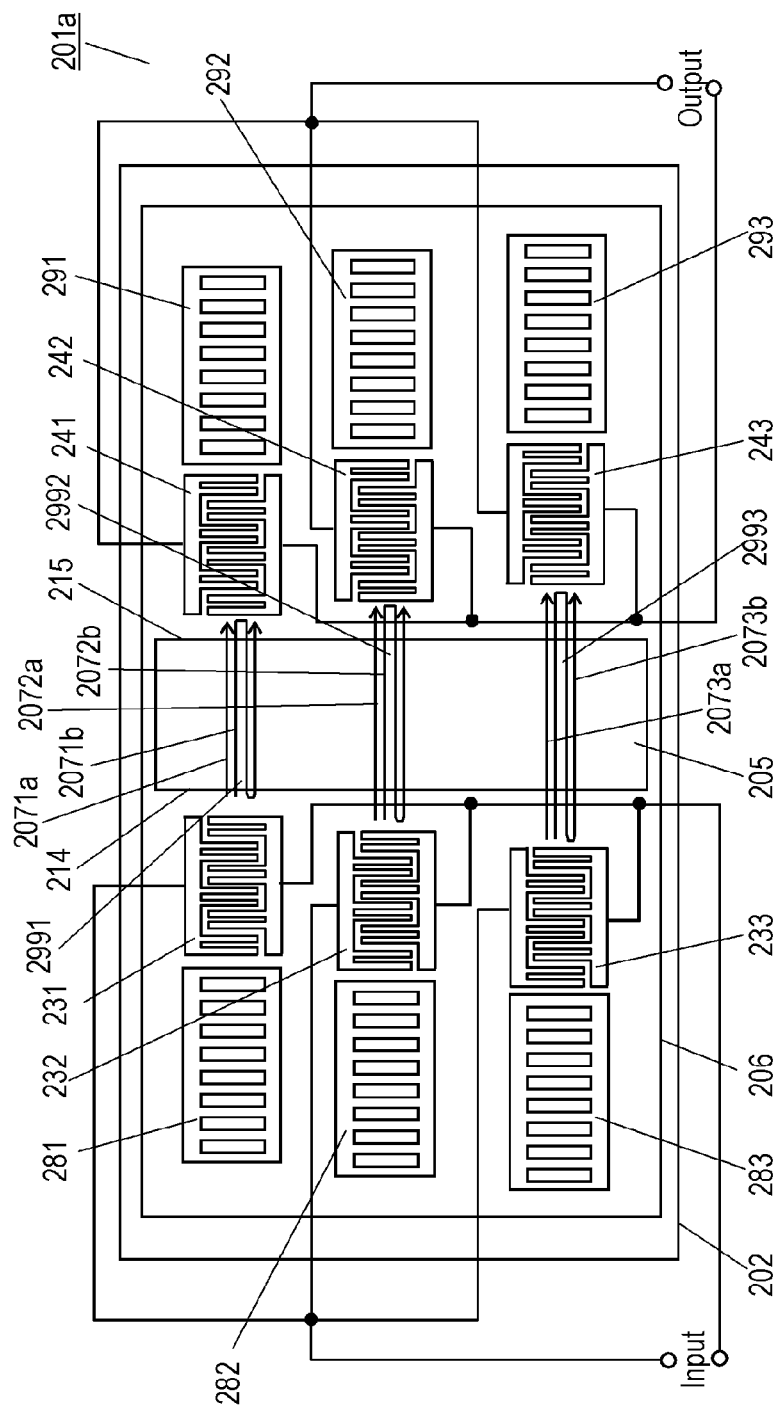
FIG. 4 is a schematic top view of another acoustic wave element according to Embodiment 1.

FIG. 4 is a schematic top view of another acoustic wave element 201a according to Embodiment 1. In FIG. 4, components identical to those of acoustic wave element 201 illustrated in FIG. 1 are denoted by the same reference numerals. Acoustic wave element 201a illustrated in FIG. 4 further includes reflectors 281 to 283 and 291 to 293 in place of acoustic absorbents 220 and 221 of acoustic wave element 201 illustrated in FIG. 1. Reflectors 281 to 283 and 291 to 293 are provided on upper surface 202a of piezoelectric substrate 202 and covered by dielectric layer 206. Reflectors 281 to 283 are positioned opposite to receiving electrodes 241 to 243 with respect to excitation electrodes 231 to 233, respectively. Reflectors 291 to 293 are positioned opposite to excitation electrodes 231 to 233 with respect to receiving electrodes 241 to 243, respectively. Reflectors 281 to 283 may allow excitation electrodes 231 to 233 to function as unidirectional electrodes. Similarly, reflectors 291 to 293 may allow receiving electrodes 241 to 243 to function as unidirectional electrodes. In this configuration, even if excitation electrodes 231 to 233 and receiving electrodes 241 to 243 are not unidirectional electrodes, reflectors 281, 282, 283, 291, 292, and 293 outside electrodes 231 to 233 and 241 to 243 allowing excitation electrodes 231 to 233 and receiving electrodes 241 to 243 to function as unidirectional electrodes improve sensitivity of acoustic wave sensor 261 including acoustic wave element 201a. Reflectors 281 to 283 and 291 to 293 may be made of, for example, a single metal selected from aluminum, copper, silver, gold, titanium, tungsten, platinum, molybdenum, or chromium, or an alloy mainly containing any of these metals, or may have a laminated structure of these metals.

Figure 5:
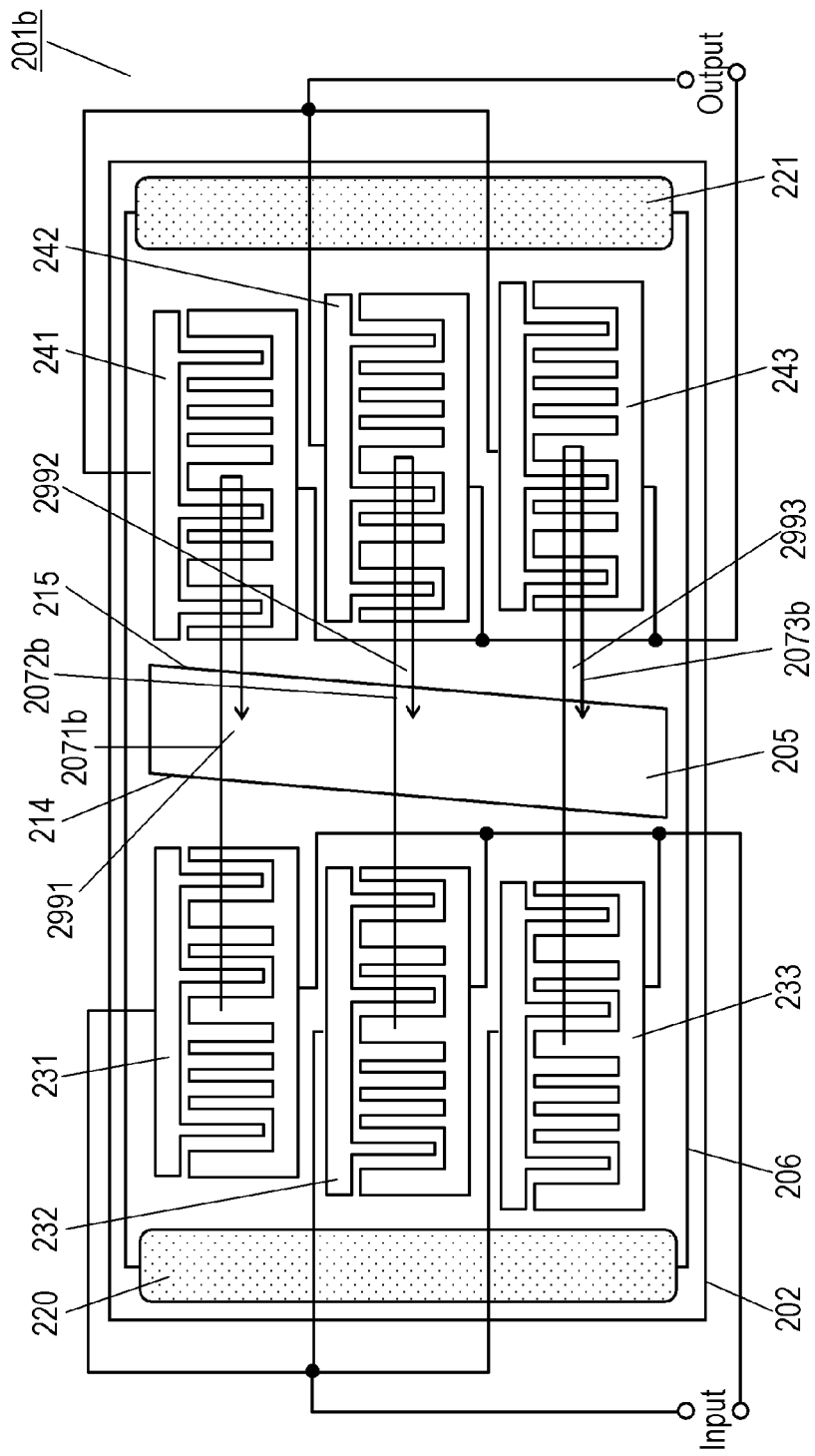
FIG. 5 is a schematic top view of still another acoustic wave element according to Embodiment 1.

FIG. 5 is a schematic top view of still another acoustic wave element 201b according to Embodiment 1. In FIG. 5, components identical to those of acoustic wave element 201 illustrated in FIG. 1 are denoted by the same reference numerals.

In acoustic wave element 201 illustrated in FIG. 1, a direction in which the electrode fingers of the IDT electrodes of excitation electrode 203 extend is identical to a direction in which outer edges 214 and 215 of sensing portion 205 between excitation electrodes 231 to 233 and receiving electrodes 241 to 243 extend. This configuration may cause a traveling wave and a reflected wave to cancel each other due to main acoustic waves 2071b to 2073b output from excitation electrodes 231 to 233 reflected by outer edge 214 or outer edge 215 of sensing portion 205 at an angle of 180 degrees.

In acoustic wave element 201b illustrated in FIG. 5, the direction in which outer edges 214 and 215 of sensing portion 205 between excitation electrodes 231 to 233 and receiving electrodes 241 to 243 extend is different from both of a direction in which the electrode fingers of excitation electrodes 231 to 233 extend and a direction in which the electrode fingers of receiving electrodes 241 to 243 extend. Specifically, the propagation directions along which main acoustic waves 2071b to 2073b propagate, i.e., propagation paths 2991 to 2993 are not perpendicular to outer edges 214 and 215 of sensing portion 205 and incline with respect to outer edges 214 and 215 of sensing portion 205. This configuration prevents a traveling wave and a reflected wave from cancelling each other due to main acoustic waves 2071b to 2073b output from excitation electrodes 231 to 233 reflecting upon outer edge 214 or outer edge 215 of sensing portion 205 at 180 degrees in a traveling direction of acoustic waves. As a result, it is possible to improve sensitivity of acoustic wave sensor 261 using acoustic wave element 201b.

Figure 6:
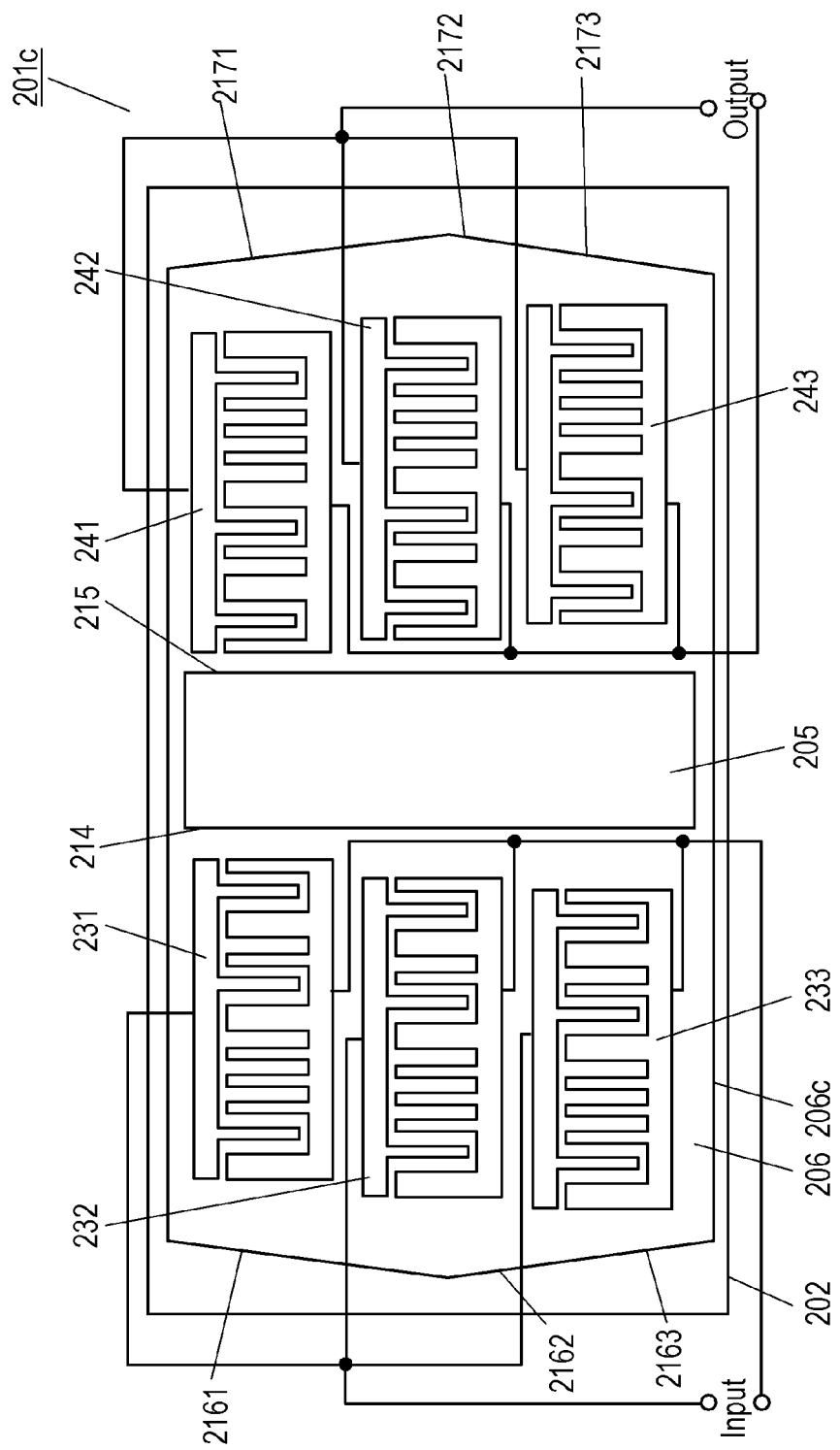
FIG. 6 is a schematic top view of further acoustic wave element according to Embodiment 1.

FIG. 6 is a schematic top view of further acoustic wave element 201c according to Embodiment 1. In FIG. 6, components identical to those of acoustic wave element 201 illustrated in FIG. 1 are denoted by the same reference numerals. Acoustic wave element 201c illustrated in FIG. 6 does not include acoustic absorbents 220 and 221 of acoustic wave element 201 illustrated in FIG. 1.

Outer edge 206c of dielectric layer 206 includes portions 2161 to 2163 positioned opposite to receiving electrodes 241 to 243 with respect to excitation electrodes 231 to 233, respectively. Directions in which portions 2161 to 2163 of outer edge 206c of dielectric layer 206 extend are preferably different from the directions in which the electrode fingers of excitation electrodes 231 to 233 extend, respectively. Specifically, a propagation direction along which unnecessary acoustic waves output from excitation electrodes 231 to 233 propagate may not preferably be perpendicular to directions in which portions 2161 to 2163 of outer edge 206c of dielectric layer 206 extend and incline with respect to the directions in which portions 2161 to 2163 of outer edge 206c extend, respectively. This configuration can prevent, without providing an acoustic absorbent, deterioration sensitivity of acoustic wave sensor 261 from decreasing due to unnecessary acoustic waves output from excitation electrodes 231 to 233, reflected by outer edge 206c of dielectric layer 206 at 180 degrees, and entering the propagation paths between excitation electrodes 231 to 233 and receiving electrodes 241 to 243.

Outer edge 206c of dielectric layer 206 includes portions 2171 to 2173 positioned opposite to excitation electrodes 231 to 233 with respect to receiving electrodes 241 to 243, respectively. Directions in which portions 2171 to 2173 of outer edge 206c of dielectric layer 206 extend are preferably different from a direction in which the electrode fingers of receiving electrodes 241 to 243 extend, respectively. Specifically, a propagation direction of acoustic waves passing through receiving electrodes 241 to 243 is not preferably perpendicular to the directions in which portions 2171 to 2173 of outer edge 206c of dielectric layer 206 extend and incline with respect to the directions in which portions 2171 to 2173 of outer edge 206c of dielectric layer 206 extend. This configuration can prevent, without providing an acoustic absorbent, sensitivity of acoustic wave sensor 261 at outer edge 206c of dielectric layer 206 from deteriorating due to acoustic waves passing through receiving electrodes 241 to 243, reflecting at 180 degrees, and entering the propagation paths between receiving electrodes 241 to 243 and excitation electrodes 231 to 233.

Figure 7:
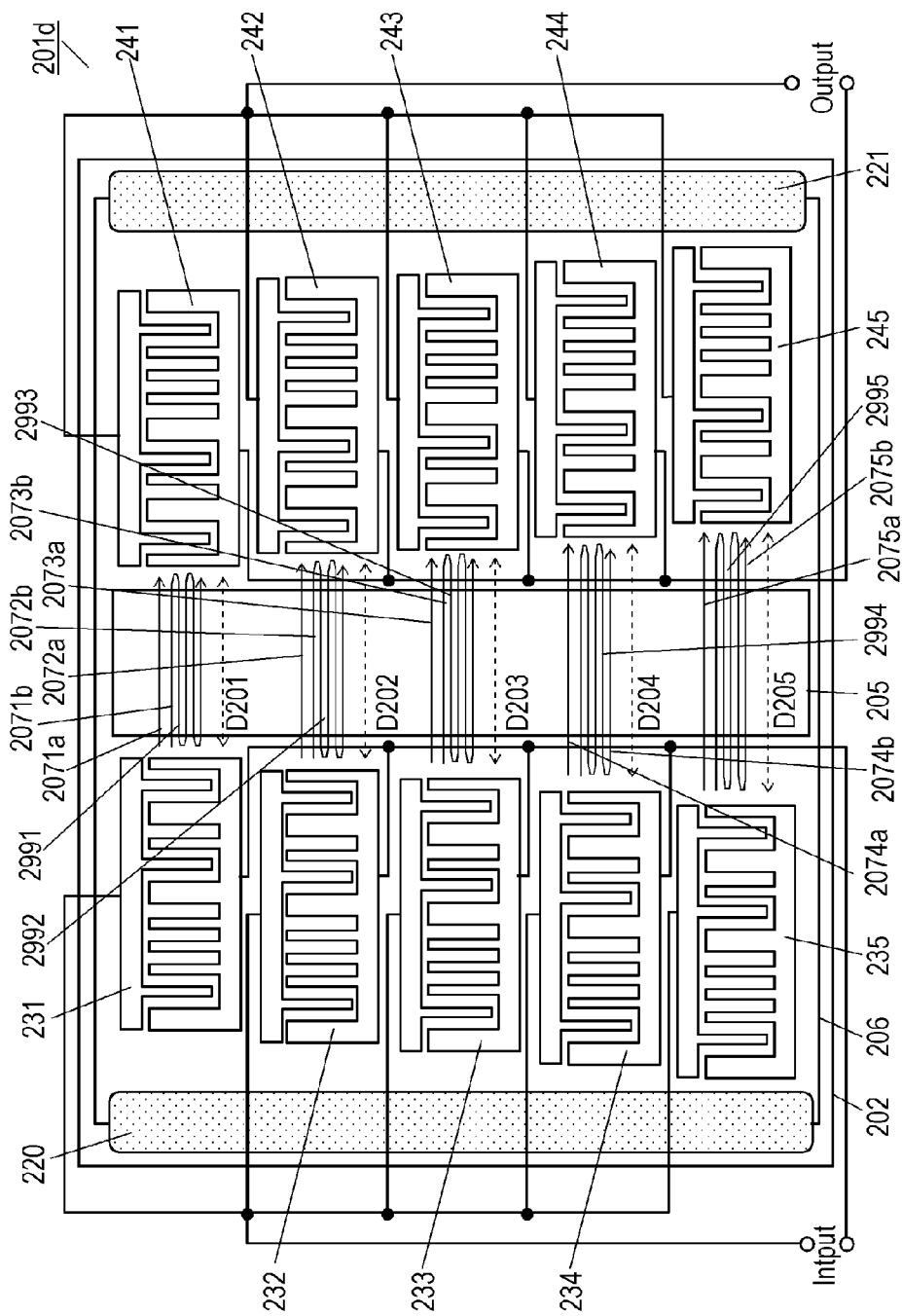
FIG. 7 is a schematic top view of further acoustic wave element according to Embodiment 1.

FIG. 7 is a schematic top view of further acoustic wave element 201d according to Embodiment 1. In FIG. 7, components identical to those of acoustic wave element 201 illustrated in FIG. 1 are denoted by the same reference numerals.

In acoustic wave element 201d according to Embodiment 1, the number of the excitation electrodes and the number of the receiving electrodes is m (m is an odd number not smaller than three). Specifically, acoustic wave element 201d includes piezoelectric substrate 202, the m excitation electrodes (m is an odd number not smaller than three) provided on upper surface 202a of piezoelectric substrate 202, the m receiving electrodes provided on upper surface 202a of piezoelectric substrate 202, plural propagation paths between the m excitation electrodes and the m receiving electrodes along which main acoustic waves propagate, and sensing portion 205 provided above the plurality of propagation paths. Each of the m receiving electrodes corresponds to respective one of the m excitation electrodes, and receives a main acoustic wave output from respective one of the m excitation electrodes. Sensing portion 205 is configured to attach or react to an object substance or a binding material to be bound with the object substance. The main acoustic waves have wavelength $\lambda$. Two of distances between the m excitation electrodes and the m receiving electrodes corresponding to the m excitation electrodes are different from each other by a difference of $\lambda/m + n\cdot\lambda$ (where n is an integer). The difference allows an error of $\lambda/18\cdot(m-1)$. Specifically, two of the distances between the m excitation electrodes and the respective m receiving electrodes corresponding to the m excitation electrodes are different from each other by a difference ranging from $\lambda/m + n\lambda - \lambda/18\cdot(m-1)$ to $\lambda/m + n\cdot\lambda + \lambda/18\cdot(m-1)$ (where n is an integer). The object substance is detected by a main acoustic wave out of plural main acoustic waves which passes through the sensing portion along the m propagation paths plural times viewing from above.

Acoustic wave element 201d illustrated in FIG. 7 has the number m of m=5. Propagation path 2991 along which a main acoustic wave propagates is formed between excitation electrode 231 and receiving electrode 241. Propagation path 2992 along which a main acoustic wave propagates is formed between excitation electrode 232 and receiving electrode 242. Propagation path 2993 along which a main acoustic wave propagates is formed between excitation electrode 233 and receiving electrode 243. Propagation path 2994 along which a main acoustic wave propagates is formed between excitation electrode 234 and receiving electrode 244. Propagation path 2995 along which a main acoustic wave propagates is formed between excitation electrode 235 and receiving electrode 245. Sensing portion 205 is provided above propagation paths 2991 to 2995. Sensing portion 205 is configured to attach or react to the object substance or the binding material to be bound with the object substance.

Main acoustic wave 2071a is output from excitation electrode 231 and directly input to receiving electrode 241, i.e. input to receiving electrode 241 after passing through sensing portion 205 along propagation path 2991 only once viewing from above. Main acoustic wave 2072a is output from excitation electrode 232 and directly input to receiving electrode 242, that is, input to receiving electrode 242 after passing through sensing portion 205 along propagation path 2992 only once viewing from above. Main acoustic wave 2073a is output from excitation electrode 233 and directly input to receiving electrode 243, that is, input to receiving electrode 243 after passing through sensing portion 205 along propagation path 2993 only once viewing from above. Main acoustic wave 2074a is output from excitation electrode 234 and directly input to receiving electrode 244, that is, input to receiving electrode 244 after passing through sensing portion 205 along propagation path 2994 only once viewing from above. Main acoustic wave 2075a is output from excitation electrode 235 and directly input to receiving electrode 245, that is, input to receiving electrode 245 after passing through sensing portion 205 along propagation path 2995 only once viewing from above. Excitation electrodes 231 to 235 and receiving electrodes 241 to 245 are disposed such that signals output from receiving electrodes 241 to 245 in response to main acoustic waves 2071a to 2075a are added so as to cancel each other.

Further, main acoustic wave 2071b is input to receiving electrode 241 after propagating along propagation path 2991 between excitation electrode 231 and receiving electrode 241 plural predetermined times, that is, input to receiving electrode 241 after passing through sensing portion 205 five times along propagation path 2991 viewing from above. Main acoustic wave 2072b is input to receiving electrode 242 after propagating along propagation path 2992 between excitation electrode 232 and receiving electrode 242 plural predetermined times, that is, input to receiving electrode 242 after passing through sensing portion 205 five times along propagation path 2992 viewing from above. Main acoustic wave 2073b is input to receiving electrode 243 after propagating along propagation path between excitation electrode 233 and receiving electrode 243 plural predetermined times, that is, input to receiving electrode 243 after passing through sensing portion 205 five times along propagation path 2993 viewing from above. Main acoustic wave 2074b is input to receiving electrode 244 after propagating along propagation path between excitation electrode 234 and receiving electrode 244 plural predetermined times, that is, input to receiving electrode 244 after passing through sensing portion 205 five times along propagation path 2994 viewing from above. Main acoustic wave 2075b is input to receiving electrode 245 after propagating along propagation path between excitation electrode 235 and receiving electrode 245 plural predetermined times, that is, input to receiving electrode 245 after passing through sensing portion 205 five times along propagation path 2995 viewing from above. Excitation electrodes 231 to 235 and receiving electrodes 241 to 245 are disposed such that signals of output from receiving electrodes 241 to 245 in response to main acoustic waves 2071b to 2075b are added so as to strengthen each other.

In acoustic wave element 201d according to Embodiment 1, signals produced by receiving electrodes 241 to 245 in response to the main acoustic waves passing through sensing portion 205 along propagation paths 2991 to 2995 one or more times, such as three times, other than the plural predetermined times are added so as to cancel each other. Therefore, in acoustic wave element 201d according to Embodiment 1, the signals produced by receiving electrodes 241 to 245 in response to the main acoustic waves passing through sensing portion 205 along propagation paths 2991 to 2995 the plural predetermined times are added so as to strengthen each other.

A minimal distance between an electrode finger out of plural electrode fingers of excitation electrode 234 closest to receiving electrode 244 and an electrode finger out of the plural electrode fingers of receiving electrode 244 closest to excitation electrode 234 is defined as distance D204 between excitation electrode 234 and receiving electrode 244. Similarly, a minimal distance between an electrode finger out of the plural electrode fingers of excitation electrode 235 closest to receiving electrode 245 and an electrode finger out of the plural electrode fingers of receiving electrode 245 closest to excitation electrode 235 is defined as distance D205 between excitation electrode 235 and receiving electrode 245. Main acoustic waves 2071a to 2075a and 2071b to 2075b received by receiving electrodes 241 to 245 have wavelength $\lambda$. A difference between distance D201 between excitation electrode 231 and receiving electrode 241 and distance D202 between excitation electrode 232 and receiving electrode 242 is $\lambda/5+n_1 \cdot \lambda$ (where $n_1$ is an integer). A difference between distance D202 between excitation electrode 232 and receiving electrode 242 and distance D203 between excitation electrode 233 and receiving electrode 243 is $\lambda/5+n_2 \cdot \lambda$ (where $n_2$ is an integer). A difference between distance D203 between excitation electrode 233 and receiving electrode 243 and distance D204 between excitation electrode 234 and receiving electrode 244 is $\lambda/5+n_3 \cdot \lambda$ (where $n_3$ is an integer). A difference between distance D204 between excitation electrode 234 and receiving electrode 244 and distance D205 between excitation electrode 235 and receiving electrode 245 is $\lambda/5+n_4 \cdot \lambda$ (where $n_4$ is an integer). Each of the differences allows an error of $\lambda/72$. Integers $n_1$, $n_2$, $n_3$, and $n_4$ are preferably identical to each other, but may be different from each other.

In other words, the difference between distance D201 between excitation electrode 231 and receiving electrode 241 and distance D203 between excitation electrode 233 and receiving electrode 243 is $2 \cdot \lambda/5+(n_1+n_2) \cdot \lambda$. A difference between distance D201 between excitation electrode 231 and receiving electrode 241 and distance D204 between excitation electrode 234 and receiving electrode 244 is $3 \cdot \lambda/5+(n_1+n_2+n_3) \cdot \lambda$. A difference between distance D201 between excitation electrode 231 and receiving electrode 241 and distance D205 between excitation electrode 235 and receiving electrode 245 is $4 \cdot \lambda/5+(n_1+n_2+n_3+n_4) \cdot \lambda$.

In the above arrangement of the electrode, phases of main acoustic waves 2071a and 2072a received by receiving electrodes 241 and 242 are different from each other by a difference of $(72+360 \cdot n_1)$ degrees. Phases of main acoustic waves 2072a and 2073a received by receiving electrodes 242 and 243 are different from each other by a difference of $(72+360 \cdot n_2)$ degrees. Phases of main acoustic waves 2073a and 2074a received by receiving electrodes 243 and 244 are different from each other by a difference of (72+360·$n_3$) degrees. Phases of main acoustic waves 2074a and 2075a received by receiving electrodes 244 and 245 are different from each other by a difference of (72+360·$n_4$) degrees. Each of the above phase differences allows an error within a range of ±5 degrees. Specifically, the phases of main acoustic waves 2071a and 2073a received by receiving electrodes 241 and 243 are different from each other by a difference of (144+360·($n_1$+$n_2$)) degrees. The phases of main acoustic waves 2071a and 2074a received by receiving electrodes 241 and 244 are different from each other by a difference of (216+360·($n_1$+$n_2$+$n_3$)) degrees. The phases of main acoustic waves 2071a and 2075a received by receiving electrodes 241 and 245 are different from each other by a difference of (288+360·($n_1$+$n_2$+$n_3$+$n_4$)) degrees. In this configuration, signals response to main acoustic waves 2071a to 2075a that are directly input to receiving electrodes 241 to 245, respectively, after passing through sensing portion 205 only once viewing from above are added so as to cancel each other. Main acoustic wave 2071b is reflected by receiving electrode 241 and excitation electrode 231, and input to receiving electrode 241 after passing through sensing portion 205 along propagation path 2991 five times viewing from above. Main acoustic wave 2072b is reflected by receiving electrode 242 and excitation electrode 232, and input to receiving electrode 242 after passing through sensing portion 205 along propagation path 2992 five times viewing from above. Main acoustic wave 2073b is reflected by receiving electrode 243 and excitation electrode 233, and input to receiving electrode 243 after passing through sensing portion 205 along propagation path 2993 five times viewing from above. Main acoustic wave 2074b is reflected by receiving electrode 244 and excitation electrode 234, and input to receiving electrode 244 after passing through sensing portion 205 along propagation path 2994 five times viewing from above. Main acoustic wave 2075b is reflected by receiving electrode 245 and excitation electrode 235, and input to receiving electrode 245 after passing through sensing portion 205 along propagation path 2995 five times viewing from above. The difference between phases of any two of the signals response to main acoustic waves 2071b to 2075b output from receiving electrodes 241 to 245 ranges from −25 degrees to 25 degrees. The signals are added so as to strengthen each other, provide a combined signal with large amplitude.

That is, the first to m-th excitation electrodes (231 to 235) are configured to excite and output the first to m-th main acoustic waves (2071b to 2075b) on upper surface 202a of piezoelectric substrate 202, respectively. The first to m-th receiving electrodes (241 to 245) are configured to receive the first to m-th main acoustic waves (2071b to 2075b) output from the first to m-th excitation electrodes (231 to 235), respectively. The first to m-th propagation paths (2991 to 2995) are provided from the first to m-th excitation electrodes (231 to 235) to the first to m-th receiving electrodes (241 to 245), and are configured to allow the first to m-th main acoustic waves (2071b to 2075b) to propagate, respectively. Sensing portion 205 is provided above the first to m-th propagation paths (2991 to 2995). The first to m-th main acoustic waves (2071b to 2075b) have wavelength λ. Considering the errors described above, two of the first to m-th distances (D201 to D205) from the first to m-th excitation electrodes (231 to 235) to the first to m-th receiving electrodes (241 to 245), respectively, are different from each other by a difference ranging from λ/m+n·λ−λ/18·(m−1) to λ/m+n·λ+λ/18·(m−1) (where n is an integer). The first to m-th main acoustic waves (2071b to 2075b) are configured to pass through sensing portion 205 plural predetermined times (five times according to Embodiment 1) along the first to m-th propagation paths (2991 to 2995), respectively.

In the case that the m excitation electrodes and the m receiving electrodes are provided on piezoelectric substrate 202 (where m is an odd number not smaller than three), considering the errors described above, the distances from the excitation electrodes (231 to 235) to the receiving electrodes (241 to 245) corresponding to the excitation electrodes (231 to 235) are different from each other by a difference ranging from λ/m+n·λ−λ/18·(m−1) to λ/m+n·λ+λ/18·(m−1). In this configuration, the phases of the main acoustic waves (2071a to 2075a) received by the respective receiving electrodes (241 to 245) are different from each other by a difference ranging from 360/m+360·n−20/(m−1) degrees to 360/m+360·n+20/(m−1) degrees (where n is an integer).

In this configuration, the main acoustic waves (2071b to 2075b) that are added so as to strengthen each other pass through sensing portion 205 above the propagation paths (2991 to 2995) m times (five times according to Embodiment 1) and reach the receiving electrodes (241 to 245). The difference between phases of two of the main acoustic waves (2071b to 2075b) reaching the receiving electrodes (241 to 245) ranges from −20·m/(m−1) degrees to 20·m/(m−1) degrees. Therefore, signals response to the acoustic waves are added so as to strengthen each other, and provide a combined signal with large amplitude. The signals produced by the receiving electrodes (241 to 245) in response to the main acoustic waves reaching the receiving electrodes (241 to 245) after passing through the sensing portion (205) plural times other than m times are added so as to cancel each other. Therefore, when the object substance or the binding material to be bound with the object substance is attached to sensing portion 205, sensing portion 205 clearly exhibits changes in characteristics, such as a mass or other physical amounts of sensing portion 205. As a result, the characteristics of the main acoustic waves (2071b to 2075b) further change, and further improve sensing sensitivity of sensing portion 205 of acoustic wave element 201.

Exemplary Embodiment 2

Figure 8A:
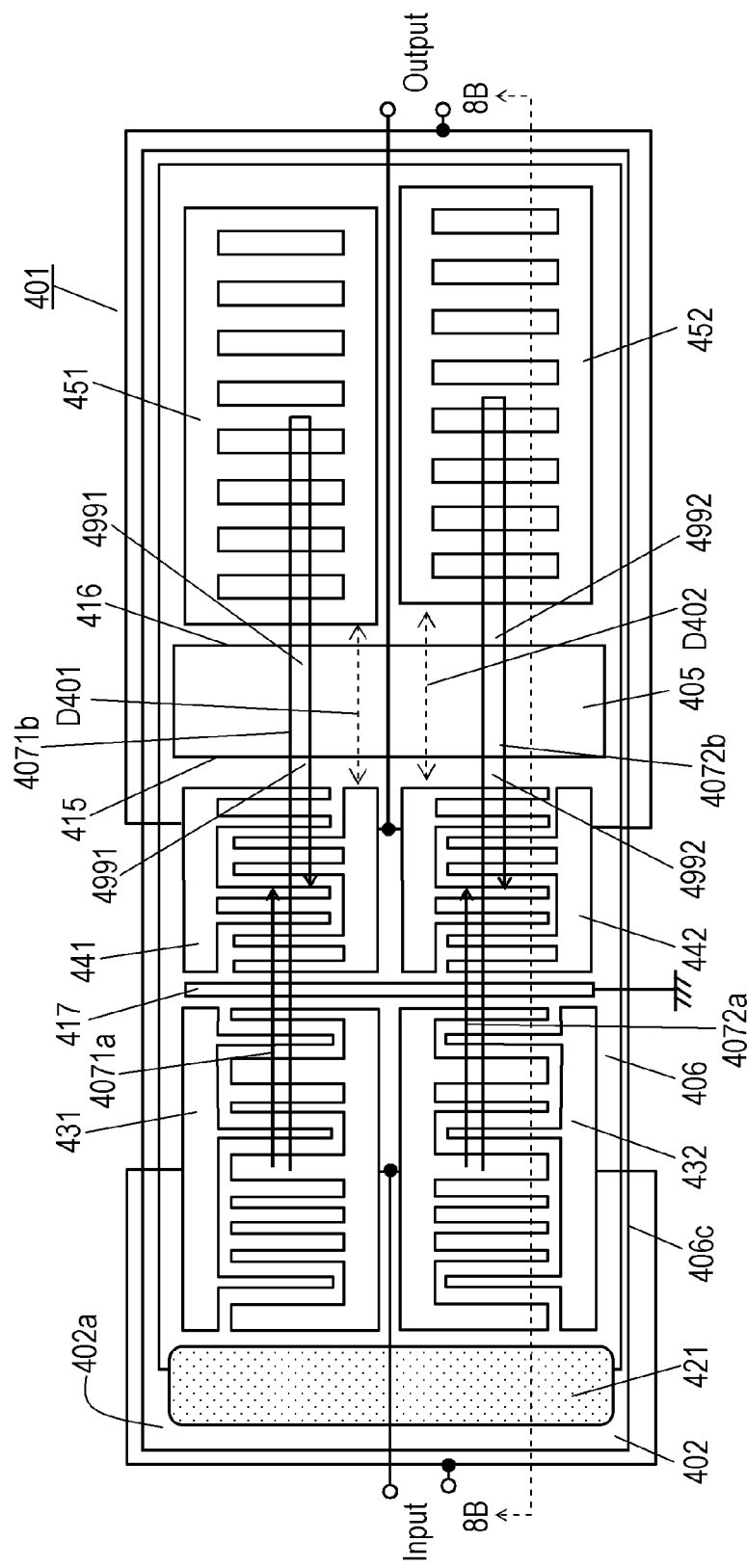
FIG. 8A is a schematic top view of an acoustic wave element according to Exemplary Embodiment 2 of the present invention.
Figure 8B:
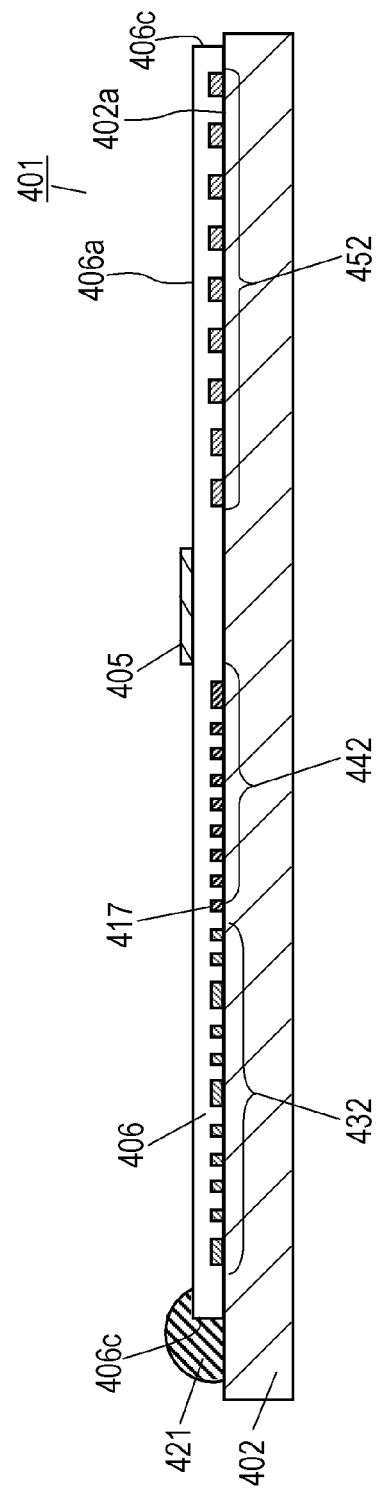
FIG. 8B is a schematic sectional view of the acoustic wave element at line 8B-8B shown in FIG. 8A.

FIG. 8A is a schematic top view of acoustic wave element 401 according to Exemplary Embodiment 2. FIG. 8B is a schematic sectional view of acoustic wave element 401 at line 8B-8B illustrated in FIG. 8A. Acoustic wave element 401 is a transversal type acoustic wave element, and is applicable to an acoustic wave sensor that senses an object substance, such as a protein, a gene, or a signal molecule, based on a biomolecule recognition mechanism.

Acoustic wave element 401 includes piezoelectric substrate 402, and excitation electrodes 431 and 432 provided on upper surface 402a of piezoelectric substrate 402. Excitation electrode 431 excites main acoustic waves 4071a and 4071b upon receiving a signal input thereto. Excitation electrode 432 excites main acoustic waves 4072a and 4072b upon receiving the signal input thereto. Excitation electrode 431 and excitation electrode 432 are connected in parallel to each other.

Acoustic wave element 401 further includes receiving electrodes 441 and 442 provided on upper surface 402a of piezoelectric substrate 402. Receiving electrode 441 is configured to receive main acoustic waves 4071a and 4071b output from excitation electrode 431, and output signals in response to main acoustic waves 4071a and 4071b that have been received. Receiving electrode 442 is configured to receive main acoustic waves 4072a and 4072b output from excitation electrode 432, and output signals of received main acoustic waves 4072a and 4072b. Receiving electrode 441 and receiving electrode 442 are connected in parallel to each other.

Acoustic wave element 401 further includes reflectors 451 and 452 provided on upper surface 402a of piezoelectric substrate 402. Reflector 451 is positioned opposite to excitation electrode 431 with respect to receiving electrode 441. Reflector 452 is positioned opposite to excitation electrode 432 with respect to receiving electrode 442. Specifically, receiving electrode 441 is positioned between excitation electrode 431 and reflector 451 while and receiving electrode 442 is positioned between excitation electrode 432 and reflector 452. Acoustic wave element 401 includes propagation path 4991 and propagation path 4992. Propagation path 4991 along which a main acoustic wave propagates is provided between receiving electrode 441 and reflector 451. Propagation path 4992 along which a main acoustic wave propagates is provided between receiving electrode 442 and reflector 452.

Excitation electrodes 431 and 432 and receiving electrodes 441 and 442 are disposed such that a phase of main acoustic wave 2071a that is output from excitation electrode 431 and directly reaches receiving electrode 441 is opposite to a phase of main acoustic wave 2072a that is output from excitation electrode 432 and reaches receiving electrode 442.

Main acoustic wave 4071b is output from excitation electrode 431, passes through receiving electrode 441, and then, is reflected by reflector 451 to propagate along propagation path 4991 twice and be input to receiving electrode 441. Main acoustic wave 4072b is output from excitation electrode 432, passes through receiving electrode 442, and then, is reflected by reflector 452 to propagate along propagation path 4992 twice and be input to receiving electrode 442. Excitation electrodes 431 and 432, receiving electrodes 441 and 442, and reflectors 451 and 452 are disposed such that the signals response to main acoustic waves 4071b and 4072b are added so as to strengthen each other.

Acoustic wave element 401 further includes dielectric layer 406 provided on upper surface 402a of piezoelectric substrate 402, and sensing portion 405 provided on upper surface 406a of dielectric layer 406. Sensing portion 405 is positioned above propagation paths 4991 and 4992, and reacts or is attached to the object substance or the binding material to be bound with the object substance. Sensing portion 405 has outer edges 415 416. Outer edge 415 faces receiving electrodes 441 and 442. Outer edge 416 faces reflectors 451 and 452.

Figure 9:
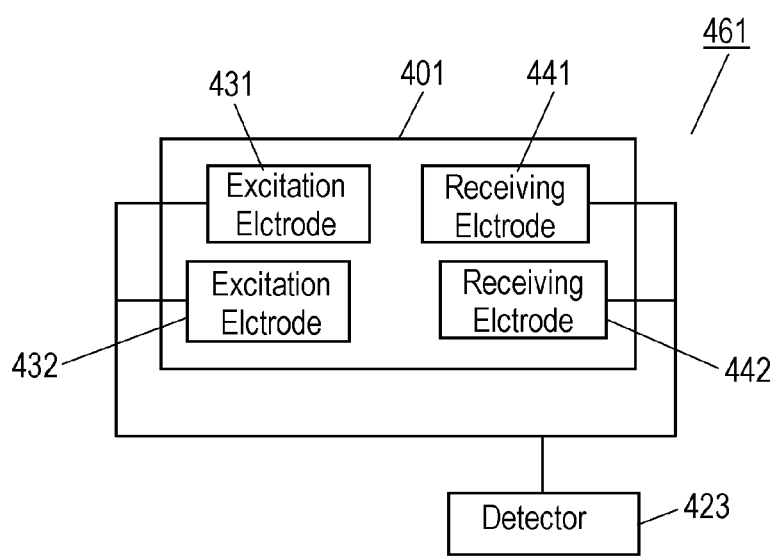
FIG. 9 is a schematic view of the acoustic wave sensor according to Embodiment 2.

FIG. 9 is a schematic view of acoustic wave sensor 461 including acoustic wave element 401. Acoustic wave sensor 461 includes acoustic wave element 401 and detector 423. Detector 423 is configured to detect characteristics (e.g. delay time characteristics, phase characteristics, or amplitude characteristics) of main acoustic waves in response to an electric signal resulting from a combined signal including a signal output from receiving electrode 441 and a signal output from receiving electrode 442. Detector 423 is electrically connected to excitation electrodes 431 and 432.

Acoustic wave element 401 is mounted onto a mother board built in an electronic device, such as a medical device. Acoustic wave element 401 may be mounted face down on the mother board such that a surface of piezoelectric substrate 402 having electrodes 431, 432, 441, and 442 formed thereon faces the mother board. In this case, receiving electrodes 441 and 442 are electrically connected to detector 423 via, e.g. metal bumps. Acoustic wave element 401 may be mounted face up on the mother board such that a surface opposite to the surface having electrodes 431, 432, 441, and 442 formed thereon is bonded to the mother board. In this case, receiving electrodes 441 and 442 are electrically connected to detector 423 via, e.g. metal wires.

A test substance, such as expired air or test liquid, possibly containing an object substance contacts sensing portion 405, and changes a physical amount of sensing portion 405 such as a mass due to attachment of the object substance. Detector 423 can detect changes in the characteristics of the main acoustic waves due to such a change, and thus sense a presence or a concentration of the object substance, for example.

Piezoelectric substrate 402 is made of a piezoelectric single crystal substrate, such as a crystal, a langasite-based piezoelectric substrate, a lithium niobate-based piezoelectric substrate, a lithium tantalite-based piezoelectric substrate, or a potassium niobate-based piezoelectric substrate.

Each of excitation electrodes 431 and 432 and receiving electrodes 441 and 442 is an interdigital transducer (IDT) electrode including a pair of comb-shaped electrodes each including plural electrode fingers that interdigitate with each other, and excites or receives main acoustic waves (4071a, 4072a, 4071b, 4072b), such as shear-horizontal (SH) waves or Rayleigh waves. Electrodes 431, 432, 441, and 442 are made of, for example, single metal, such as aluminum, copper, silver, gold, titanium, tungsten, platinum, molybdenum, or chromium, or an alloy mainly containing any of these metals, or may have a laminated structure of these metals.

Each of reflectors 451 and 452 is a grating reflector including plural electrode fingers extend in parallel to each other, and reflect main acoustic waves 4071b and 4072b excited by excitation electrodes 431 and 432 and passing through receiving electrodes 441 and 442, respectively. Reflectors 451 and 452 are made of, for example, a single metal, such as aluminum, copper, silver, gold, titanium, tungsten, platinum, molybdenum, or chromium, or an alloy mainly containing any of these metals, or may have a laminated structure of these metals.

An operation of acoustic wave element 401 will be detailed below.

A distance between excitation electrode 431 and receiving electrode 441 is equal to a distance between excitation electrode 432 and receiving electrode 442. Each of excitation electrodes 431 and 432 includes comb-shaped electrodes with the same configuration (the same electrode finger pitches, the same electrode finger interdigitating width, and the same electrode finger width). Each of receiving electrodes 441 and 442 includes comb-shaped electrodes with the same configuration (the same electrode finger pitches, the same electrode finger interdigitating width, and the same electrode finger width). The comb-shaped electrodes of receiving electrodes 441 and 442 are connected to an output perpendicularly to the propagation direction of the main acoustic waves and inverted to each other with respect to a direction of potential such that phases are inverted.

Therefore, the signal of main acoustic wave 4071a that is output from excitation electrode 431 and directly reaches receiving electrode 441, and the signal of main acoustic wave 4072a that is output from excitation electrode 432 and directly reaches receiving electrode 442 are added so as to cancel each other.

Main acoustic waves 4071a, 4071b, 4072a, and 4072b have wavelength 2. In acoustic wave element 401, distance D401 between receiving electrode 441 and reflector 451 and distance D402 between receiving electrode 442 and reflector 452 are different from each other by a difference of $\lambda/4+n\cdot\lambda/2$ (where n is an integer). The difference between distance D401 and distance D402 allows an error within $\pm\lambda/36$ with respect to the above value. Main acoustic wave 4071b is output from excitation electrode 431 and reaches receiving electrode 441 after passing through receiving electrode 441 and reflector 451. Main acoustic wave 4072b is output from excitation electrode 432 and reaches receiving electrode 442 after passing through receiving electrode 442 and reflector 452. Considering the errors described above, since the distances along propagation paths 4991 and 4992 are different from each other by a difference ranging from $\lambda/2+n\cdot\lambda-\lambda/18$ to $\lambda/2+n\cdot\lambda+\lambda/18$, the signal output from receiving electrode 441 in response to main acoustic wave 4071b and the signal output from receiving electrode 442 in response to of main acoustic wave 4072b are added so as to strengthen each other, and provide a combined signal with large amplitude. As described above, in acoustic wave element 401, receiving electrodes 441 and 442 effectively receive main acoustic waves 4071b and 4072b that propagate twice along propagation paths 4991 and 4992. Specifically, viewing from above, main acoustic waves 4071b and 4072b added so as to strengthen each other pass through sensing portion 405 positioned above propagation paths 4991 and 4992 plural times, and reach receiving electrodes 441 and 442, respectively. Therefore, when an object substance or a binding material to be bound with the object substance is attached to sensing portion 405, the characteristics, such as delay time characteristics, of main acoustic waves 4071b and 4072b change sufficiently large, and accordingly improve sensitivity of sensing portion 405 of acoustic wave element 401.

In conventional acoustic wave element 501 illustrated in FIG. 28, main acoustic wave 507 excited by excitation electrode 503 propagates on sensing portion 505 along a propagation path only once and then reaches receiving electrode 504. Therefore, characteristics, such as delay time characteristics and phase characteristics, of main acoustic wave 507 may not change sufficiently even when the object substance is attached. This may not ensure sensitivity of sensing portion 505 of acoustic wave element 501.

Excitation electrodes 431 and 432 may have, but not limited to, the same configuration. However, at least the pitches of the electrode fingers of excitation electrodes 431 and 432 are preferably identical to each other.

Receiving electrodes 441 and 442 may have, but not limited to, the same configuration. However, at least the pitches of the electrode fingers of receiving electrodes 441 and 442 may be preferably identical to each other.

Reflectors 451 and 452 may have, but not limited to, the same configuration (the same electrode finger pitches, the same electrode finger length, and the same electrode finger width). However, at least the pitches of the electrode fingers of reflectors 451 and 452 may be identical to each other.

Dielectric layer 406 provided on upper surface 402a of piezoelectric substrate 402 preferably cover at least excitation electrodes 431 and 432 and receiving electrodes 441 and 442. This configuration suppresses corrosion of electrodes 431, 432, 441, and 442 due to a solvent containing the object substance as well as deterioration of sensing sensitivity of acoustic wave sensor 461 using acoustic wave element 401 subjected to the corrosion. Dielectric layer 406 preferably covers propagation paths 4991 and 4992, and sensing portion 405 is preferably provided on upper surface 406a of dielectric layer 406 above propagation paths 4991 and 4992. This configuration suppresses reflection of the main acoustic waves by outer edges 415 and 416 of sensing portion 405 across propagation paths 4991 and 4992 between excitation electrodes 431 and 432 and receiving electrodes 441 and 442, hence improving sensitivity of acoustic wave sensor 461 including acoustic wave element 401.

Figure 10:
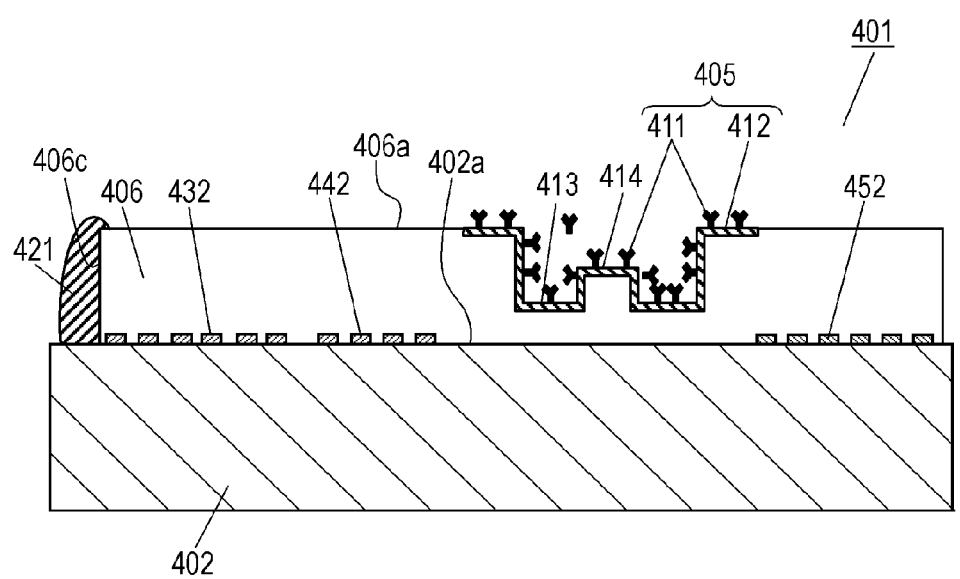
FIG. 10 is a schematic sectional view of the acoustic wave element according to Embodiment 2.

Components of acoustic wave element 401 will be detailed below. FIG. 10 is an enlarged schematic view of acoustic wave element 401 illustrated in FIG. 8B for showing a section of acoustic wave element 401 in a propagation direction of the main acoustic waves between excitation electrode 432 and reflector 452.

Excitation electrode 431 is preferably a unidirectional electrode that allows main acoustic waves 4071a and 4071b to propagate in a direction toward receiving electrode 441 more efficiently than any direction other than the direction toward receiving electrode 441. Excitation electrode 432 is preferably a unidirectional electrode that allows main acoustic waves 4072a and 4072b to propagate in a direction toward receiving electrode 442 more efficiently than any direction other than the direction toward receiving electrode 442. Receiving electrodes 441 and 442 are preferably bidirectional electrodes. This configuration can improve sensitivity of acoustic wave sensor 461 including acoustic wave element 401.

Sensing portion 405 includes antibodies 411 and adhesion layer 412 bonding antibodies 411 to a surface of piezoelectric substrate 402 or a surface of dielectric layer 406. Antibody 411 reacts to an object substance or a binding material to be bound with the object substance that may possibly contained in a test substance, such as expired air. Adhesion layer 412 is made of an adhesive material, such as a metal or an organic substance. Antibodies 411 may be directly attached to piezoelectric substrate 402 or dielectric layer 406 without adhesion layer 412 between antibodies 411 and piezoelectric substrate 402 or dielectric layer 406.

Dielectric layer 406 is made of an inorganic dielectric material, or may be made of a medium, such as silicon oxide ($SiO_2$), having a frequency-temperature coefficient opposite to that of piezoelectric substrate 402. Dielectric layer 406 covering electrodes 431, 432, 441, and 442 can improve a frequency-temperature characteristic of acoustic wave element 401. Further, dielectric layer 406 may be made of another dielectric material, such as silicon nitride, silicon nitride oxide, aluminum nitride, aluminum oxide, tantalum oxide, tellurium oxide, diamond, or silicone.

As illustrated in FIG. 10, the upper surface of dielectric layer 406 is preferably uneven to have recess 413 and projection 414 on an upper surface of adhesion layer 412. The width of recess 413 wider than a maximum width of antibody 411 allows antibodies 411 provided within recess 413. Recess 413 and projection 414 may be formed by etching predetermined positions of dielectric layer 406 by, e.g. dry etching after dielectric layer 406 is formed on upper surface 402a of piezoelectric substrate 402 by, e.g. sputtering or vapor deposition.

Acoustic wave element 401 may further include acoustic absorbent 421 provided on upper surface 402a of piezoelectric substrate 402 so as to cover outer edge 406c of dielectric layer 406. Acoustic absorbent 421 is disposed opposite to receiving electrodes 441 and 442 with respect to excitation electrodes 431 and 432. Acoustic absorbent 421 is made pf, for example, a resin, such as an epoxy resin, a silicone resin, an acrylic resin, or a polyimide. Unnecessary acoustic waves are output from excitation electrodes 431 and 432 in a direction opposite to a desired propagation direction. Acoustic absorbent 421 prevents sensitivity of acoustic wave sensor 461 from deteriorating due to the unnecessary acoustic waves reflected on outer edge 406c of dielectric layer 406, again propagating to excitation electrodes 431 and 432, and added to a desired acoustic wave. Acoustic absorbent 421 covering outer edge 406c of dielectric layer 406 improves an effect of absorbing unnecessary acoustic waves and the effect of preventing deterioration in sensitivity.

Acoustic wave element 401 may further include shield electrode 417 provided between excitation electrode 431 and receiving electrode 441 and between excitation electrode 432 and receiving electrode 442. Shield electrode 417 may preferably be grounded. Shield electrode 417 reduces direct waves due to electromagnetic field coupling excitation electrode 431 to receiving electrode 441 and electromagnetic field coupling excitation electrode 432 to receiving electrode 442, as well as to improve sensitivity of acoustic wave sensor 461.

Figure 11:
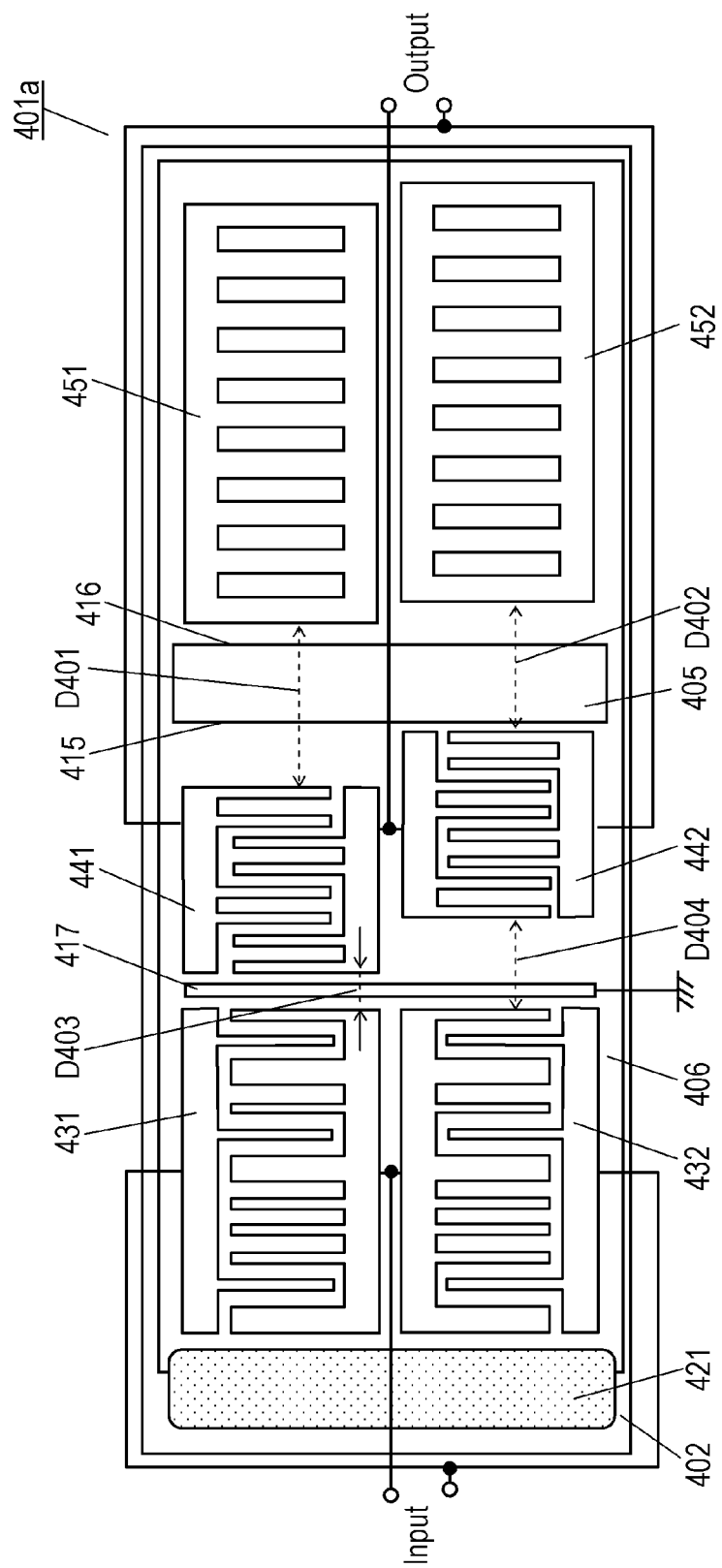
FIG. 11 is a schematic top view of another acoustic wave element according to Embodiment 2.

FIG. 11 is a schematic top view of another acoustic wave element 401a according to Embodiment 2. In FIG. 11, components identical to those of acoustic wave element 401 illustrated in FIG. 8A are denoted by the same reference numerals. In acoustic wave element 401a illustrated in FIG. 11, distance D403 between excitation electrode 431 and receiving electrode 441 and distance D404 between excitation electrode 432 and receiving electrode 442 are different from each other by a difference ranging from $\lambda/2+n\cdot\lambda-\lambda/54$ to $\lambda/2+n\cdot\lambda+\lambda/54$. Further, distance D401 between receiving electrode 441 and reflector 451 and distance D402 between receiving electrode 442 and reflector 452 are different from each other by a difference ranging from $n\cdot\lambda/2+\lambda/4-\lambda/54$ to $n\cdot\lambda/2+\lambda/4+\lambda/54$. In acoustic wave element 401a, receiving electrode 441 and receiving electrode 442 are connected to an output without inverting their comb-shaped electrode structure. Distance D403 between excitation electrode 431 and receiving electrode 441 and distance D404 between excitation electrode 432 and receiving electrode 442 are different from each other by a difference ranging from $\lambda/2+n\cdot\lambda-\lambda/54$ to $\lambda/2+n\cdot\lambda+\lambda/54$. This configuration allows a signal response to main acoustic wave 4071a that is output from excitation electrode 431 and directly reaches receiving electrode 441 and a signal response to main acoustic wave 4072a that is output from excitation electrode 432 and directly reaches receiving electrode 442 to be added so as to cancel each other. Further, distances along the propagation paths of main acoustic wave 4071b output from excitation electrode 431, passing through receiving electrode 441, reflected by reflector 451, and then, reaching receiving electrode 441 and main acoustic wave 4072b output from excitation electrode 432, passing through receiving electrode 442, reflected by reflector 452 and then reaching receiving electrode 442 are different from each other by a difference ranging from $-\lambda/2+2n\cdot\lambda-\lambda/18$ to $-\lambda/2+2n\cdot\lambda+\lambda/18$ or ranging from $-\lambda/2+(2n+1)\cdot\lambda-\lambda/18$ to $-\lambda/2+(2n+1)\cdot\lambda+\lambda/18$. Therefore, a signal response to main acoustic wave 4071b and a signal response to main acoustic wave 4072b are added so as to strengthen each other, and provides a combined signal with large amplitude. As described above, in acoustic wave element 401a, receiving electrodes 441 and 442 is configured to effectively receive main acoustic waves 4071b and 4072b that propagate twice along propagation paths 4991 and 4992, respectively. Specifically, main acoustic waves 4071b and 4072b added so as to strengthen each other pass through sensing portion 405 positioned above propagation paths 4991 and 4992 plural times, and reach receiving electrodes 441 and 442, respectively, viewing from above. Therefore, when an object substance or a binding material bound with the object substance is attached to sensing portion 405, the characteristics, such as delay time characteristics, of main acoustic waves 4071b and 4072b change sufficiently, and can improve sensitivity of sensing portion 405 of acoustic wave element 401a.

Figure 12:
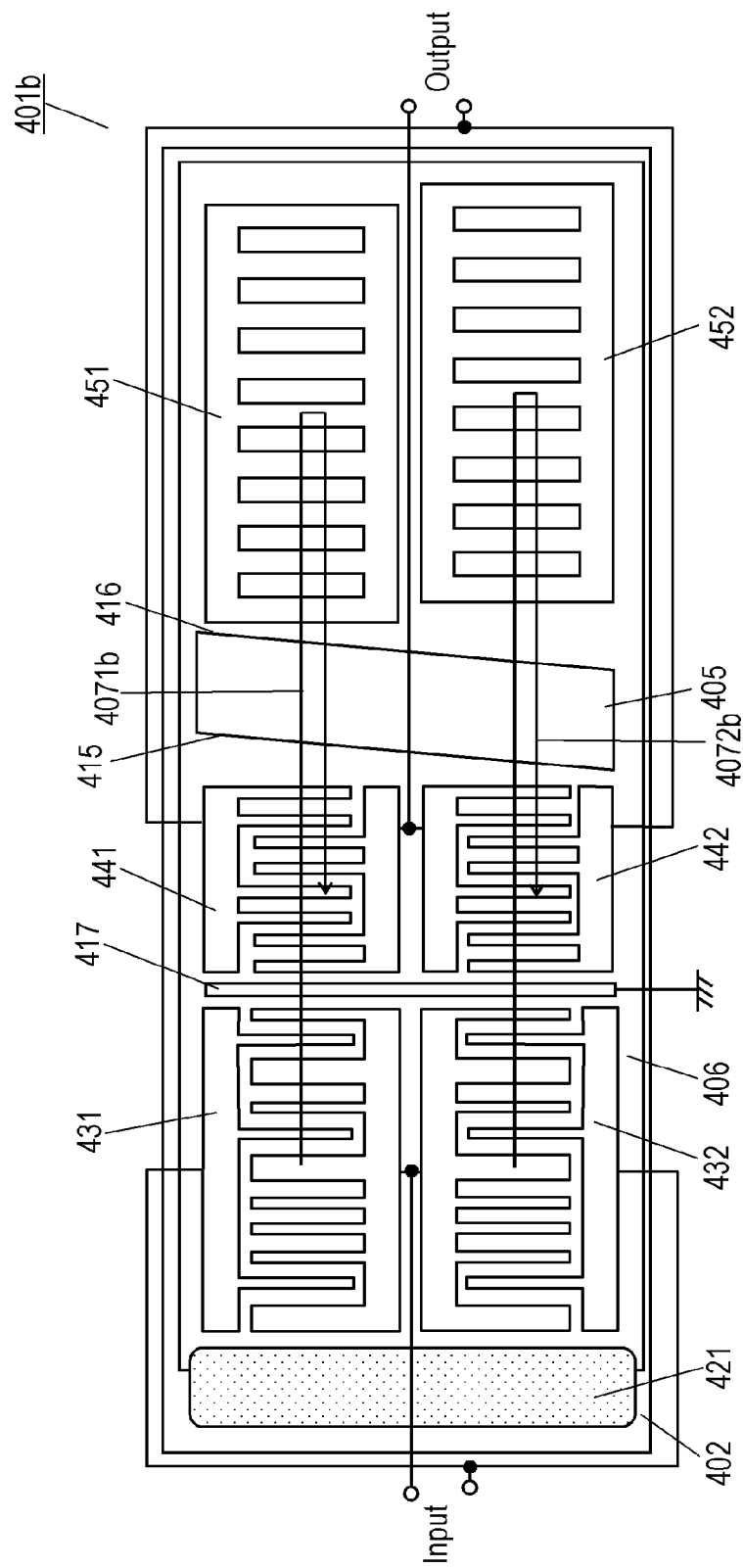
FIG. 12 is a schematic top view of further acoustic wave element according to Embodiment 2.

FIG. 12 is a schematic top view of another acoustic wave element 401b according to Embodiment 2. In FIG. 12, components identical to those of acoustic wave element 401 illustrated in FIG. 8A are denoted by the same reference numerals. In acoustic wave element 401b illustrated in FIG. 12, a direction in which outer edges 415 and 416 of sensing portion 405 between receiving electrode 441 and reflector 451 extend is different from both of a direction in which the electrode fingers of receiving electrode 441 extend and a direction in which the electrode fingers of reflector 451 extend. Further, a direction in which outer edges 415 and 416 of sensing portion 405 between receiving electrode 442 and reflector 452 extend is different from both of a direction in which the electrode fingers of receiving electrode 442 extend and a direction in which the electrode fingers of reflector 452 extend. Specifically, a propagation direction of main acoustic waves 4071b and 4072b passing through receiving electrodes 441 and 442 is not perpendicular to the direction in which outer edges 415 and 416 of sensing portion 405 extend and inclines with respect to the direction in which outer edges 415 and 416 of sensing portion 405 extend. This configuration can prevent a traveling wave and a reflected wave from cancelling each other due to main acoustic waves 4071b and 4072b that have passed thorough receiving electrodes 441 and 442 and reflected by outer edge 415 or outer edge 416 of sensing portion 405 at 180 degrees in a traveling direction of acoustic waves. As a result, it is possible to improve sensitivity of acoustic wave sensor 461 using acoustic wave element 401b.

Figure 13:
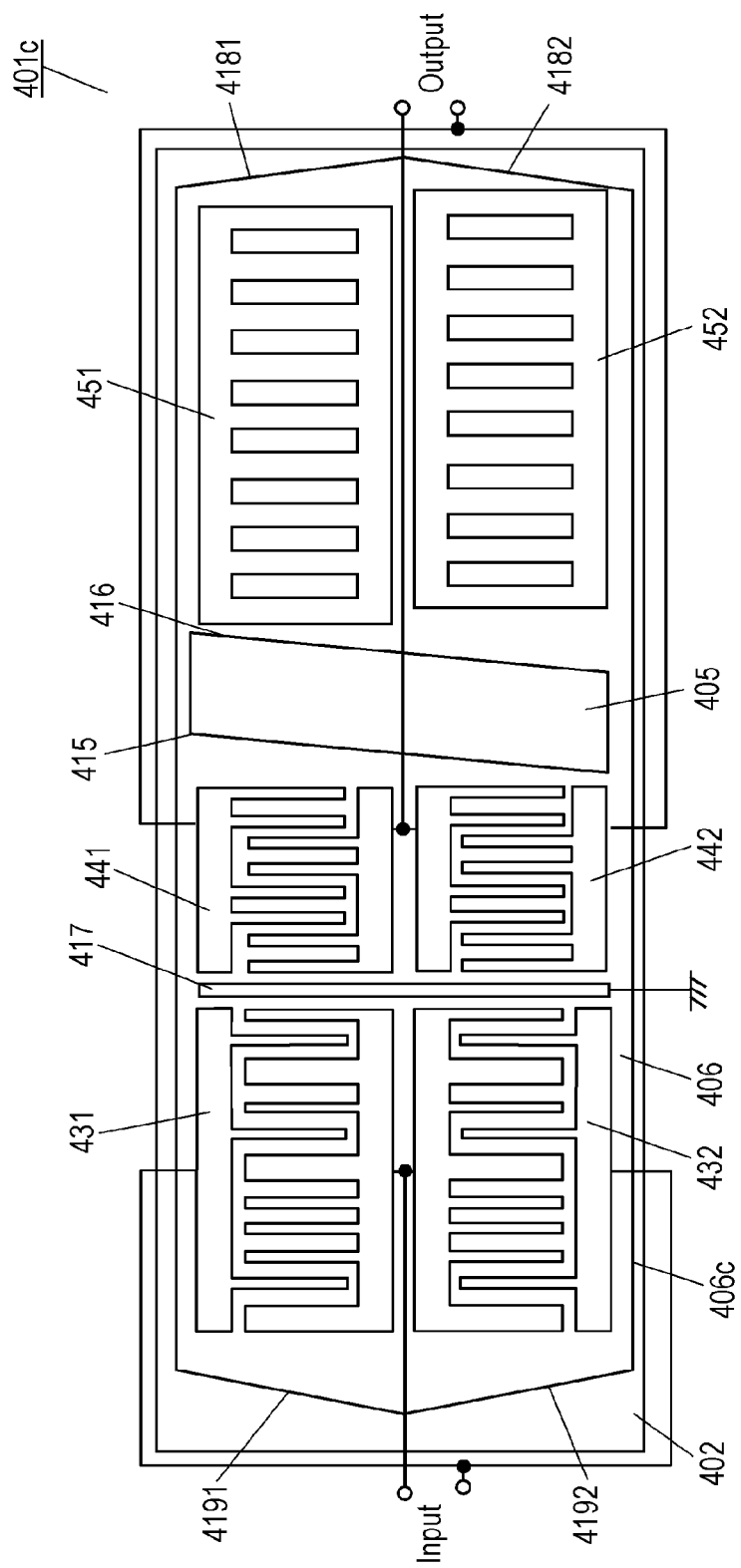
FIG. 13 is a schematic top view of further acoustic wave element according to Embodiment 2.

FIG. 13 is a schematic top view of further acoustic wave element 401c according to Embodiment 2. In FIG. 13, components identical to those of acoustic wave element 401b illustrated in FIG. 12 are denoted by the same reference numerals. Acoustic wave element 401c illustrated in FIG. 13 does not include acoustic absorbent 421. Outer edge 406c of dielectric layer 406 includes portions 4191 and 4192 positioned opposite to receiving electrodes 441 and 442 with respect to excitation electrodes 431 and 432, respectively. A direction in which portion 4191 of outer edge 406c of dielectric layer 406 extends is different from a direction in which the electrode fingers of excitation electrode 431 extend while a direction in which portion 4192 of outer edge 406c of dielectric layer 406 extends is different from a direction in which the electrode fingers of excitation electrode 432 extend. Specifically, a propagation direction of unnecessary acoustic waves output from excitation electrode 431 is perpendicular to the direction in which portion 4191 of outer edge 406c of dielectric layer 406 extends and inclines with respect to the direction in which portion 4191 of outer edge 406c of dielectric layer 406 extends. A propagation direction of unnecessary acoustic waves output from excitation electrode 432 is not perpendicular to the direction in which portion 4192 of outer edge 406c of dielectric layer 406 extends and inclines with respect to the direction in which portion 4192 of outer edge 406c of dielectric layer 406 extends. This configuration can prevent, without providing an acoustic absorbent, unnecessary acoustic waves output by excitation electrodes 431 and 432 from being reflected at 180 degrees by portions 4191 and 4192 of outer edge 406c of dielectric layer 406 and entering in propagation paths 4991 and 4992 between receiving electrodes 441 and 442 and reflectors 451 and 452. This configuration prevents sensitivity of acoustic wave sensor 461 from deteriorating due to unnecessary acoustic waves entering propagation paths 4991 and 4992.

Further, in acoustic wave element 401*c* illustrated in FIG. 13, outer edge 406*c* of dielectric layer 406 includes portions 4181 and 4182 positioned opposite to receiving electrodes 441 and 442 with respect to reflectors 451 and 452, respectively. A direction in which portion 4181 of outer edge 406*c* of dielectric layer 406 extends may preferably be different from a direction in which the electrode fingers of reflector 451 extend while a direction in which portion 4182 of outer edge 406*c* of dielectric layer 406 extends may preferably be different from a direction in which the electrode fingers of reflector 452 extend. Specifically, a propagation direction of unnecessary acoustic waves passing through reflector 451 is not perpendicular to the direction in which portion 4181 of outer edge 406*c* of dielectric layer 406 extends and inclines with respect to the direction in which portion 4181 of outer edge 406*c* of dielectric layer 406 extends while a propagation direction of unnecessary acoustic waves passing through reflector 452 is not perpendicular to the direction in which portion 4182 of outer edge 406*c* of dielectric layer 406 extends and inclines with respect to the direction in which portion 4182 of outer edge 406*c* of dielectric layer 406 extends. This configuration can prevent, without providing an acoustic absorbent, unnecessary acoustic waves passing through reflectors 451 and 452 from being reflected at 180 degrees by portions 4181 and 4182 of outer edge 406*c* of dielectric layer 406 and entering in propagation paths 4991 and 4992 between receiving electrodes 441 and 442 and reflectors 451 and 452. This configuration can prevent sensitivity of acoustic wave sensor 461 from deteriorating due to unnecessary acoustic waves entering in propagation paths 4991 and 4992.

Exemplary Embodiment 3

Figure 14A:
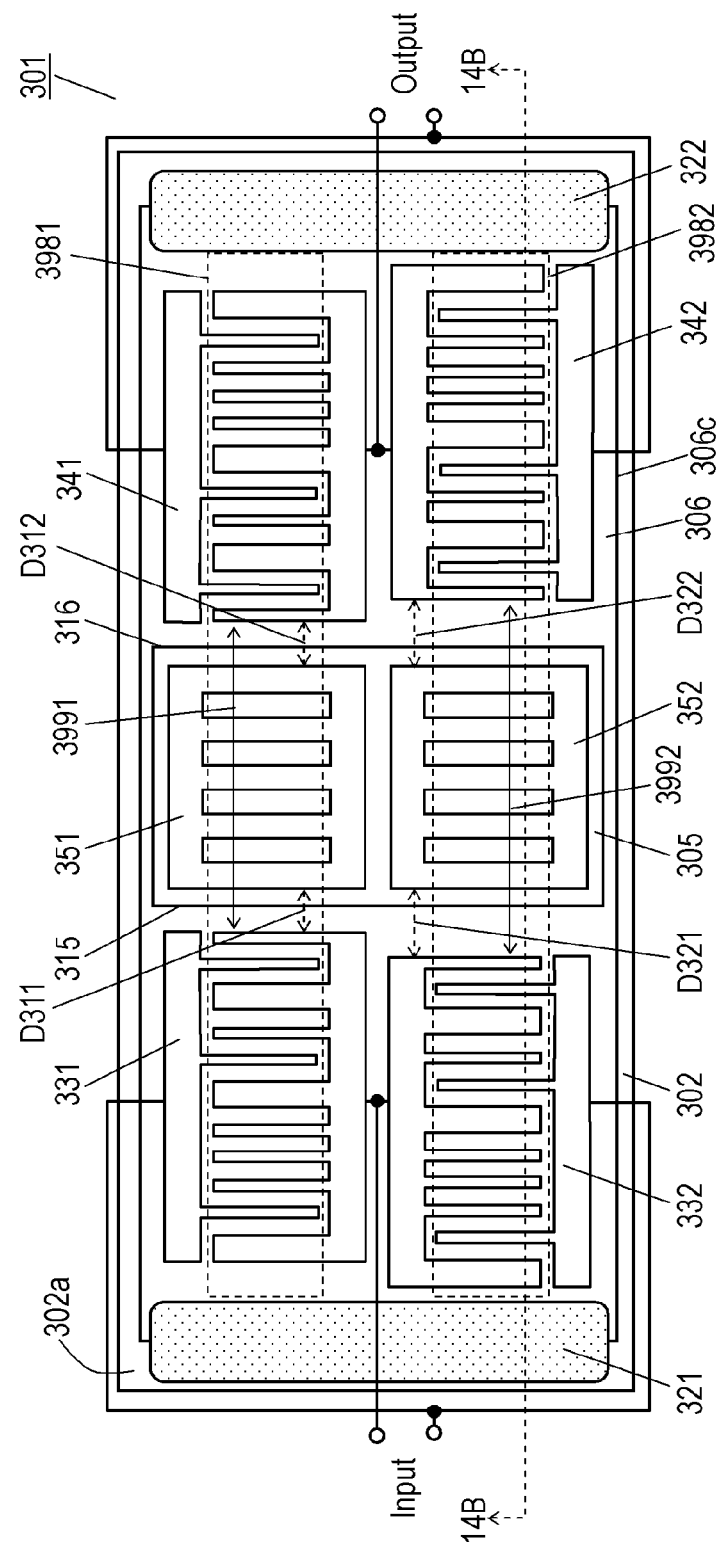
FIG. 14A is a schematic top view of an acoustic wave element according to Exemplary Embodiment 3 of the present invention.
Figure 14B:
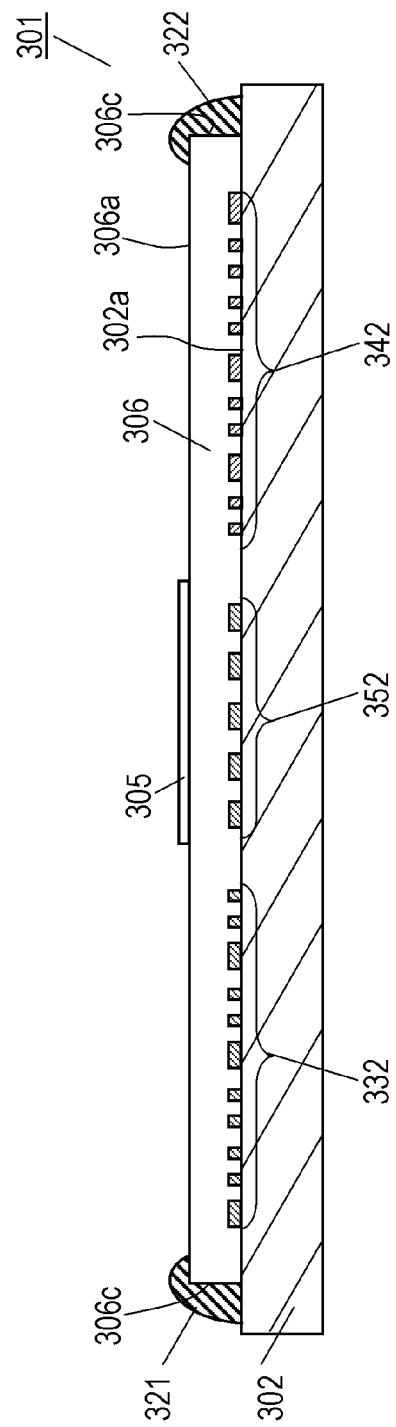
FIG. 14B is a schematic sectional view of the acoustic wave element at line 14B-14B shown in FIG. 14A.

FIG. 14A is a schematic top view of an acoustic wave element 301 according to Exemplary Embodiment 3. FIG. 14B is a schematic sectional view of acoustic wave element 301 at line 14B-14B illustrated in FIG. 14A. Acoustic wave element 301 is a transversal type acoustic wave element, and is applicable to an acoustic wave sensor that senses an object substance, such as a protein, a gene, or a signal molecule, based on a biomolecule recognition mechanism.

Acoustic wave element 301 includes piezoelectric substrate 302 and excitation electrodes 331 and 332 provided on upper surface 302*a* of piezoelectric substrate 302. Excitation electrodes 331 and 332 excite main acoustic waves on upper surface 302*a* of piezoelectric substrate 302 upon receiving a signal input thereto. Excitation electrodes 331 and 332 are connected in parallel to each other.

Acoustic wave element 301 further includes receiving electrodes 341 and 342 provided on upper surface 302*a* of piezoelectric substrate 302. Receiving electrodes 341 and 342 receive the main acoustic waves output from excitation electrodes 331 and 332, and output signals in response to the received main acoustic waves. Receiving electrodes 341 and 342 are connected in parallel to each other.

In acoustic wave element 301, propagation path 3991 along which a main acoustic wave propagates is formed between excitation electrode 331 and receiving electrode 341, and propagation path 3992 along which a main acoustic wave propagates is formed between excitation electrode 332 and receiving electrode 342.

Acoustic wave element 301 further includes reflectors 351 and 352 provided on propagation paths 3991 and 3992, respectively. Reflector 351 is positioned between excitation electrode 331 and receiving electrode 341. Reflector 352 is positioned between excitation electrode 332 and receiving electrode 342. Excitation electrode 331, receiving electrode 341, and reflector 351 constitute acoustic track 3981. Excitation electrode 332, receiving electrode 342, and reflector 352 constitute acoustic track 3982.

In acoustic wave element 301, excitation electrodes 331 and 332, receiving electrodes 341 and 342, and reflectors 351 and 352 are disposed such that the signal response to the main acoustic wave input to receiving electrode 341 after propagating along propagation path 3991 plural times and the signal response to the main acoustic wave input to receiving electrode 342 after propagating along propagation path 3992 plural times are added so as to strengthen each other.

Acoustic wave element 301 further includes dielectric layer 306 provided on upper surface 302*a* of piezoelectric substrate 302 and sensing portion 305 provided on upper surface 306*a* of dielectric layer 306. Sensing portion 305 is positioned above propagation paths 3991 and 3992, in particular, above reflectors 351 and 352, and reacts or is attached to an object substance or a binding material bound with the object substance.

Figure 15:
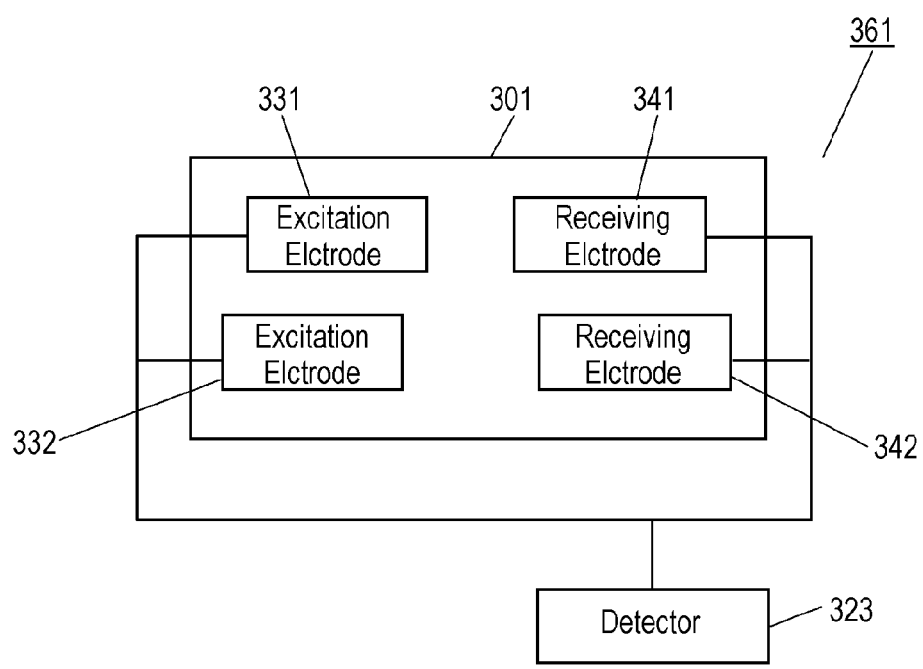
FIG. 15 is a schematic view of the acoustic wave sensor according to Embodiment 3.

FIG. 15 is a schematic view of acoustic wave sensor 361 including acoustic wave element 301. Acoustic wave sensor 361 includes acoustic wave element 301 and detector 323. Detector 323 detects characteristics (e.g. delay time characteristics, phase characteristics, or amplitude characteristics) of main acoustic waves in response to an electric signal resulting from a combined signal including the signal output from receiving electrode 341 and the signal output from receiving electrode 342. Detector 323 is electrically connected to excitation electrodes 331 and 332. While detector 323 detects a frequency change or a delay time change of the main acoustic waves received by receiving electrodes 341 and 342, detector 323 may detect other changes in the characteristics, such as a phase, speed, amplitude, or a wavelength, of the main acoustic waves.

Acoustic wave element 301 is mounted on a mother board built in an electronic device, such as a medical device. Acoustic wave element 301 may be mounted face down on the mother board such that a surface of piezoelectric substrate 302 having electrodes 331, 332, 341, and 342 formed thereon faces the mother board. In this case, receiving electrodes 341 and 342 are electrically connected to detector 323 via, e.g. metal bumps. Acoustic wave element 301 may be mounted face up on the mother board such that a surface opposite to the surface having electrodes 331, 332, 341, and 342 formed thereon is bonded to the mother board. In this case, receiving electrodes 341 and 342 are electrically connected to detector 323 via, e.g. metal wires.

While a test substance, such as expired air or test liquid, possibly containing an object substance contacts sensing portion 305, detector 323 can detect changes in the characteristics of the main acoustic waves due to a change in a physical amount of sensing portion 305 such as a mass by attachment of the object substance, and thus sense a presence or a concentration of the object substance, for example.

Each of excitation electrodes 331 and 332 and receiving electrodes 341 and 342 is an interdigital transducer (IDT) electrode including a pair of comb-shaped electrodes each including plural electrode fingers that interdigitate with each other, and excites or receives main acoustic waves, such as shear-horizontal (SH) waves or Rayleigh waves, for example. Electrodes 331, 332, 341, and 342 are made of, for example, a single metal, such as aluminum, copper, silver, gold, titanium, tungsten, platinum, molybdenum, or chromium, or an alloy mainly containing any of these metals, or may have a laminated structure of these metals.

Each of reflectors 351 and 352 is a grating reflector including plural electrode fingers extending in parallel to each other. Reflectors 351 and 352 are made of, for example, a single metal, such as aluminum, copper, silver, gold, titanium, tungsten, platinum, molybdenum, or chromium, or an alloy mainly containing any of these metals, or may have s laminated structure of these metals.

Excitation electrodes 331 and 332 may have, but not limited to, the same configuration (the same electrode finger pitch, the same electrode finger interdigitating width, and the same electrode finger width). At least the pitches of the electrode fingers of excitation electrodes 331 and 332 may preferably be identical to each other.

Receiving electrodes 341 and 342 may have, but not limited to, the same configuration (the same electrode finger pitch, the same electrode finger interdigitating width, and the same electrode finger width). However, at least the pitches of the electrode fingers of receiving electrodes 341 and 342 may preferably be identical to each other.

Further, the configuration of excitation electrodes 331 and 332 is, but not limited to, symmetrical to that of receiving electrodes 341 and 342 (the same electrode finger pitch, the same electrode finger interdigitating width, and the same electrode finger width). However, at least the pitches of the electrode fingers of excitation electrodes 331 and 332 may preferably be identical to and symmetrical to that of receiving electrodes 341 and 342.

Reflectors 351 and 352 may have, but not limited to, the same configuration (the same electrode finger pitch, the same electrode finger length, and the same electrode finger width). However, at least the pitches of the electrode fingers of reflectors 351 and 352 may preferably be identical to each other.

Figure 16:
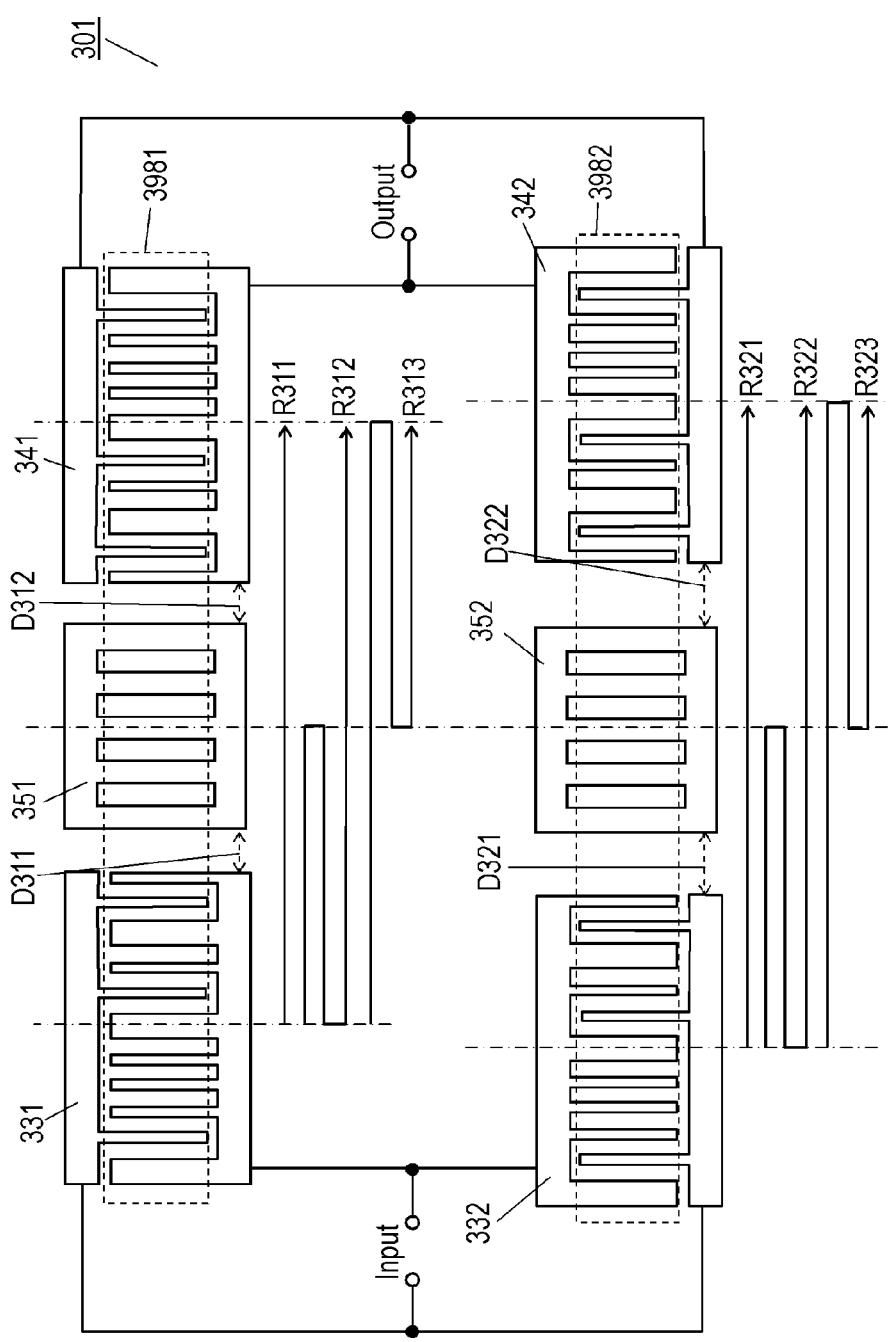
FIG. 16 is a schematic view of the acoustic wave element according to Embodiment 3 for illustrating an operation of the acoustic wave element.

An operation of acoustic wave element 301 will be detailed below. FIG. 16 is a schematic top view of acoustic wave element 301, particularly showing acoustic tracks 3981 and 3982 constituted by excitation electrodes 331 and 332, receiving electrodes 341 and 342, reflectors 351 and 352, respectively, illustrated in FIG. 14A. A minimal distance between an electrode finger out of the plural electrode fingers of excitation electrode 331 closest to reflector 351 and an electrode finger out of the plural electrode fingers of reflector 351 closest to excitation electrode 331 is defined as distance D311 between excitation electrode 331 and reflector 351. Similarly, a minimal distance between an electrode finger out of the plural of electrode fingers of excitation electrode 332 closest to reflector 352 and an electrode finger out of the plural electrode fingers of reflector 352 closest to excitation electrode 332 is defined as distance D321 between excitation electrode 332 and reflector 352. Similarly, a minimal distance between an electrode finger out of the plural of electrode fingers of receiving electrode 341 closest to reflector 351 and an electrode finger out of the plural electrode fingers of reflector 351 closest to receiving electrode 341 is defined as distance D312 between receiving electrode 341 and reflector 351. Similarly, a minimal distance between an electrode finger out of the plural electrode fingers of receiving electrode 342 closest to reflector 352 and an electrode finger out of the plural of electrode fingers of reflector 352 closest to receiving electrode 342 is defined as distance D322 between receiving electrode 342 and reflector 352. The main acoustic waves have wavelength $\lambda$. Excitation electrode 331, receiving electrode 341, and reflector 351 are disposed such that distance D321 is larger than distance D311 by a difference of $\lambda/4+n\cdot\lambda2$ (where n is an integer). The difference between distances D321 and D311 allows an error of $\pm\lambda/36$ with respect to the above values. Excitation electrode 332, receiving electrode 342, and reflector 352 are disposed such that distance D322 is larger than distance D312 by a difference of $\lambda/4+m\cdot\lambda/2$ (where m is an integer). The difference between distances D322 and D312 allows an error of $\pm\lambda/36$ with respect to the above value. Integer m is an even number I the case that integer n is an even number. Integer m is an odd number in the case that integer n is an odd number.

Excitation electrode 331 outputs main acoustic wave R311 that directly reaches receiving electrode 341 after passing through reflector 351. Excitation electrode 332 outputs main acoustic wave R321 that directly reaches receiving electrode 342 after passing through reflector 352. Considering the above errors, distances along which main acoustic waves R311 and R321 propagate are different from each other by a distance ranging from $\lambda/2+(n+m)\cdot\lambda/2-\lambda9$ to $\lambda/2+(n+m)\cdot\lambda/2+\lambda/9$. Therefore, the signals output from receiving electrodes 341 and 342 in response to main acoustic waves R311 and R321 received by receiving electrodes 341 and 342 are added so as to cancel each other.

Excitation electrode 331 further outputs main acoustic wave R312 that passes through reflector 351 and reaches receiving electrode 341 after being reflected by reflector 351 and again reflected by excitation electrode 331. Excitation electrode 332 further outputs main acoustic wave R322 that passes through reflector 352 and reaches receiving electrode 342 after being reflected by reflector 352 and again reflected by excitation electrode 332. Considering the above errors, distances along which main acoustic waves R312 and R322 propagate are different from each other by a difference ranging from $\lambda+(3n+m)\cdot\lambda/2-\lambda/9$ to $\lambda+(3n+m)\cdot\lambda/2+\lambda/9$. Therefore, the signals output from receiving electrodes 341 and 342 in response to main acoustic waves R312 and R322 received by receiving electrodes 341 and 342 are added so as to strengthen each other, and provide a combined signal with large amplitude.

Excitation electrode 331 further outputs main acoustic wave R313 that reaches receiving electrode 341 after passing through reflector 351 and being reflected by receiving electrode 341, and again being reflected by reflector 351. Excitation electrode 332 further outputs main acoustic wave R323 that reaches receiving electrode 342 after passing through reflector 352 and being reflected by receiving electrode 342, and again being reflected by reflector 352. Considering the above errors, distances along which main acoustic waves R313 and R323 propagate are different from each other by a difference ranging from $\lambda+(n+3m)\cdot\lambda/2-\lambda/18$ to $\lambda+(n+3m)\cdot\lambda/2+\lambda/18$. Therefore, the signals output from receiving electrodes 341 and 342 in response to main acoustic waves R313 and R323 received by receiving electrodes 341 and 342 are added so as to strengthen each other, and provide a combined signal with large amplitude.

As described above, in acoustic wave element 301, receiving electrodes 341 and 342 is configures to effectively receive main acoustic waves R312, R322, R313, and R323 that propagate plural times along propagation paths 3991 and 3992. Specifically, main acoustic waves R312, R322, R313, and R323 added so as to strengthen each other pass sensing portion 305 positioned above propagation paths 3991 and 3992 plural times, and reach the receiving electrodes (341, 342). Therefore, when an object substance or a binding material bound with the object substance is attached to sensing portion 305, the characteristics, such as delay time characteristics, of main acoustic waves R312, R322, R313, and R323 change sufficiently, and can improve sensitivity of sensing portion 305.

In conventional acoustic wave element 501 illustrated in FIG. 28, main acoustic wave 507 excited by excitation electrode 503 propagates across sensing portion 505 above a propagation path only once and then reaches receiving electrode 504. Therefore, characteristics, such as delay time characteristics or phase characteristics, of main acoustic wave 507 may no change sufficiently even when an object substance is attached, thus not ensuring sensitivity of sensing portion 505 of acoustic wave element 501.

Dielectric layer 306 provided on upper surface 302a of piezoelectric substrate 302 preferably covers at least excitation electrodes 331 and 332 and receiving electrodes 341 and 342. This configuration can suppress corrosion of electrodes 331, 332, 341, and 342 due to a solvent containing the object substance, as well as deterioration of sensitivity of acoustic wave sensor 361 including acoustic wave element 301 subjected to the corrosion. Sensing portion 305 has outer edges 315 and 316. Outer edge 315 faces excitation electrodes 331 and 332. Outer edge 316 faces receiving electrodes 341 and 342. Dielectric layer 306 preferably covers propagation paths 3991 and 3992. Sensing portion 305 is preferably provided above propagation paths 3991 and 3992. This configuration can suppress reflection of the main acoustic waves at outer edges 315 and 316 of dielectric layer 306 across propagation paths 3991 and 3992 between excitation electrodes 331 and 332 and receiving electrodes 341 and 342, and improves sensitivity of acoustic wave sensor 361 including acoustic wave element 301.

Figure 17:
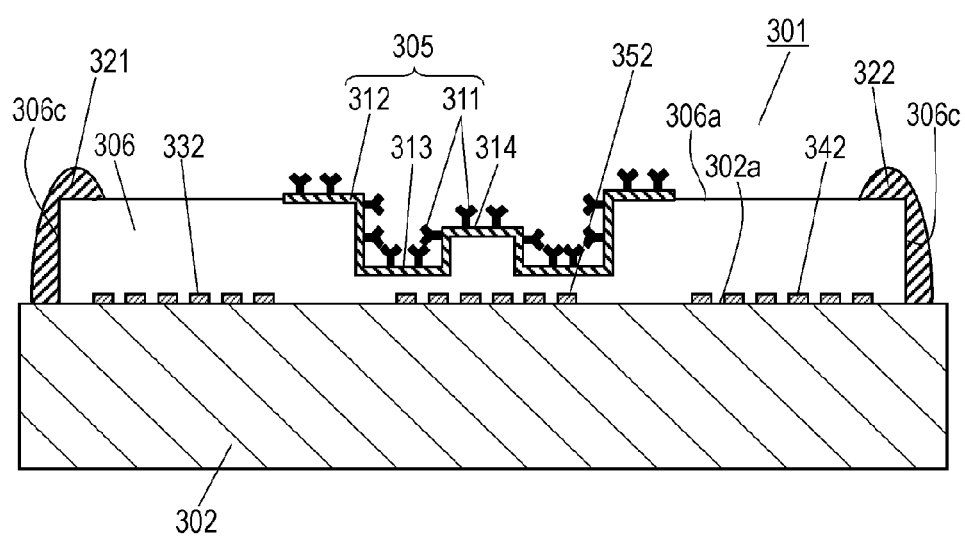
FIG. 17 is a schematic sectional view of the acoustic wave element according to Embodiment 3.

Acoustic wave element 301 will be detailed below. FIG. 17 is an enlarged sectional view of acoustic wave element 301 illustrated in FIG. 14B, showing a sectional of acoustic wave element 301 in a propagation direction of the main acoustic waves between excitation electrode 331 and receiving electrode 341.

Piezoelectric substrate 302 is made of a piezoelectric single crystal substrate, such as a crystal, a langasite-based piezoelectric substrate, a lithium niobate-based piezoelectric substrate, a lithium tantalite-based piezoelectric substrate, or a potassium niobate-based piezoelectric substrate.

Sensing portion 305 includes antibodies 311 and adhesion layer 312 bonding antibodies 311 to upper surface 302a of piezoelectric substrate 302 or upper surface 306a of dielectric layer 306. Antibodies 311 react to an object substance or a binding material to be bound with the object substance that possibly contained in a test substance, such as expired air or test liquid Adhesion layer 312 is made of an adhesive material, such as a metal or an organic substance. Antibodies 311 may be directly attached to piezoelectric substrate 302 or dielectric layer 306 without adhesion layer 312 between antibody 311 and piezoelectric substrate 302 or dielectric layer 306.

As illustrated in FIG. 17, upper surface 306a of dielectric layer 306 is uneven having recess 313 or projection 314 provided on an upper surface of adhesion layer 312 that constitutes sensing portion 305. The width of recess 313 is wider than a maximum width of antibody 311. This configuration allows antibodies 311 to be provided within recess 313. Recess 313 or projection 314 may be formed by etching predetermined positions of dielectric layer 306 by, e.g. dry etching after dielectric layer 306 is formed on upper surface 302a of piezoelectric substrate 302 by, e.g. sputtering or vapor deposition.

Dielectric layer 306 is made of an inorganic dielectric material, or may be made of a medium, such as silicon oxide (SiO$_2$), having a frequency-temperature coefficient opposite to that of piezoelectric substrate 302. Dielectric layer 306 covering electrodes 331, 332, 341, and 342 can improve a frequency-temperature characteristic of acoustic wave element 301. Further, dielectric layer 306 may be made of another dielectric material, such as silicon nitride, silicon nitride oxide, aluminum nitride, aluminum oxide, tantalum oxide, tellurium oxide, diamond, or silicone.

Acoustic wave element 301 may further include acoustic absorbents 321 and 322 provided on upper surface 302a of piezoelectric substrate 302. Acoustic absorbent 321 covers portions of outer edge 306c of dielectric layer 306 opposite to receiving electrodes 341 and 342 with respect to excitation electrodes 331 and 332, respectively. Acoustic absorbent 322 covers portions of outer edge 306c of dielectric layer 306 opposite to excitation electrodes 331 and 332 with respect to receiving electrodes 341 and 342, respectively. Acoustic absorbents 321 and 322 are made pf, for example, a resin, such as an epoxy resin, a silicone resin, an acrylic resin, or a polyimide. Acoustic absorbents 321 and 322 prevent sensitivity of acoustic wave sensor 361 from deteriorating due to unnecessary acoustic waves output from excitation electrodes 331 and 332 in a direction opposite to a desired propagation direction being reflected by outer edge 306c of dielectric layer 306, again propagating to excitation electrodes 331 and 332, and being added to the desired acoustic waves. Acoustic absorbents 321 and 322 covering outer edge 306c of dielectric layer 306 can absorb the unnecessary acoustic wave and prevent deterioration in sensitivity.

Excitation electrode 331 may preferably be a unidirectional electrode that allows main acoustic waves R311, R312, and R313 to propagate in a direction toward receiving electrode 341 more efficiently than any direction other than the direction toward receiving electrode 341. Excitation electrode 332 may preferably be a unidirectional electrode that allows main acoustic waves R321, R322, and R323 to propagate in a direction toward receiving electrode 342 more efficiently than in any direction other than the direction toward receiving electrode 342. Receiving electrode 341 may preferably be a unidirectional electrode that receives main acoustic waves R311, R312, and R313 in a direction from excitation electrode 331 more efficiently than any direction other than the direction from excitation electrode 331. Receiving electrode 342 may preferably be a unidirectional electrode that receives main acoustic waves R321, R322, and R323 in a direction from excitation electrode 332 more efficiently than any direction other than the direction from excitation electrode 332. This configuration can improve sensitivity of acoustic wave sensor 361 using acoustic wave element 301. In addition, electrodes 331, 332, 341, and 342 implemented by unidirectional electrodes can improve reflection efficiencies of the main acoustic waves by excitation electrodes 331 and 332 and receiving electrodes 341 and 342.

The number of the electrode fingers and a duty of each of reflectors 351 and 352 are determined such that a half of the main acoustic wave is reflected and the remaining half of the main acoustic wave is transmitted. This configuration allows the main acoustic waves that propagate plural times along propagation paths 3991 and 3992 to be added so as to strengthen each other and to be efficiently received by receiving electrodes 341 and 342. Thus, it is possible to improve sensitivity of acoustic wave element 301.

Figure 18:
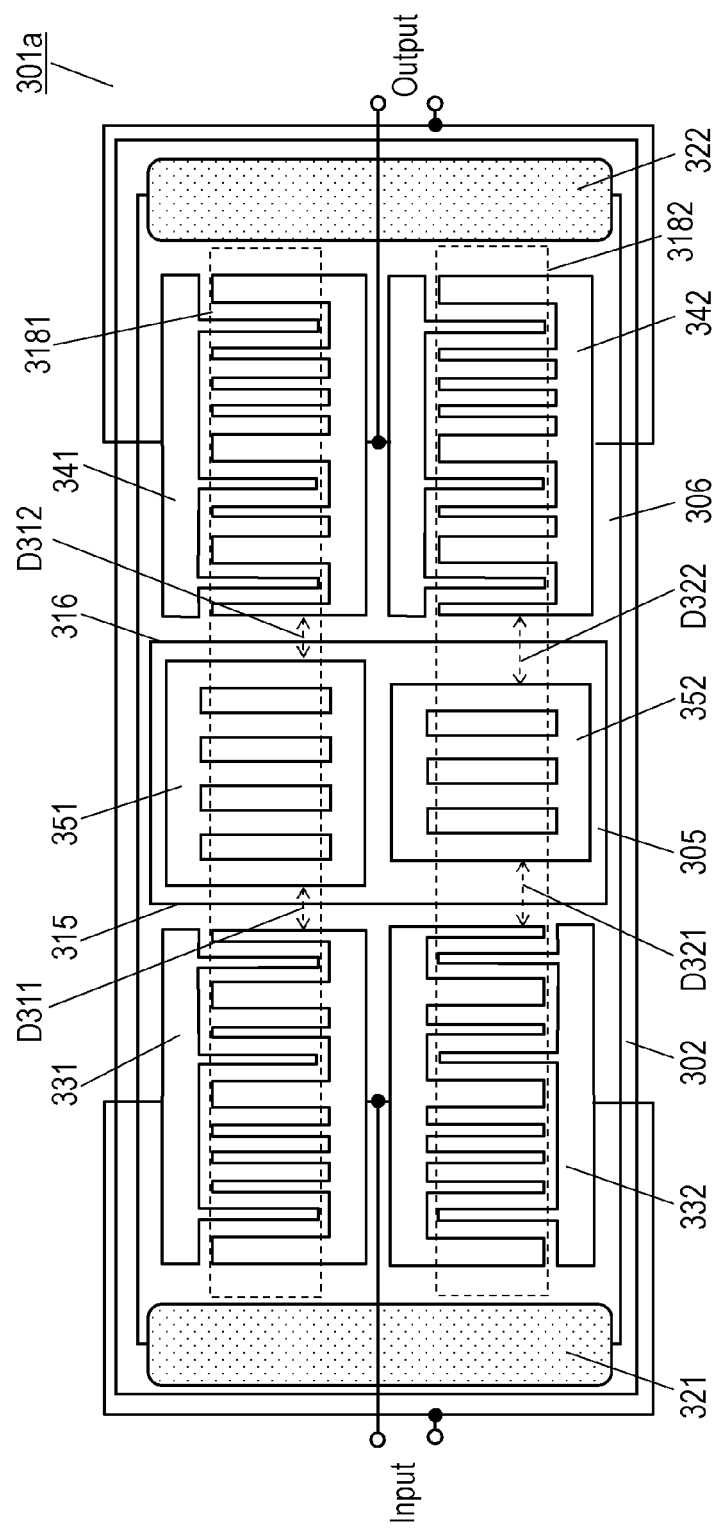
FIG. 18 is a schematic top view of another acoustic wave element according to Embodiment 3.

FIG. 18 is a schematic top view of another acoustic wave element 301a according to Embodiment 3. In FIG. 18, components identical to those of acoustic wave element 301 illustrated in FIG. 14A are denoted by the same reference numerals. In the acoustic wave element illustrated in FIG. 18, the number of the electrode fingers of reflector 351 and the number of the electrode fingers of reflector 352 are different from each other by an odd number. In acoustic wave element 301a, a propagation direction in which main acoustic waves propagate along propagation paths 3991 and 3992, a distance between a center of excitation electrode 331 and a center of receiving electrode 341 is equal to a distance between a center of excitation electrode 332 and a center of receiving electrode 342. Receiving electrode 341 and receiving electrode 342 are disposed such that a polarity of the electrode fingers of the comb-shaped electrode of receiving electrode 341 is inverted to a polarity of the electrode fingers of the comb-shaped electrode of receiving electrode 342. This configuration allows main acoustic wave R311 that propagates once along propagation path 3991 from excitation electrode 331 and directly reaches receiving electrode 341 and main acoustic wave R321 that propagates once along propagation path 3992 from excitation electrode 332 and directly reaches receiving electrode 342 to be received by receiving electrode 341 and receiving electrode 342 with phases of main acoustic waves R311 and R321 opposite to each other. Since the number of the electrode fingers of reflector 352 is smaller than the number of the electrode fingers of reflector 351 by the odd number (one shown in FIG. 18), distance D321 between excitation electrode 332 and reflector 352 is longer than distance D311 between excitation electrode 331 and reflector 351 by a difference ranging from $\lambda/4n\cdot\lambda/2-\lambda 36$ to $\lambda/4+n\cdot\lambda/2+\lambda 36$. Further, distance D322 between reflector 352 and receiving electrode 342 is longer than distance D312 between reflector 351 and receiving electrode 341 by a difference ranging from $\lambda 4+m\cdot\lambda/2-\lambda/36$ to $\lambda/4+m\cdot\lambda/2+\lambda/36$. Integer m is an even number in the case that integer n is an even number. Integer m is an odd number in the case that integer n is an odd number.

Figure 19:
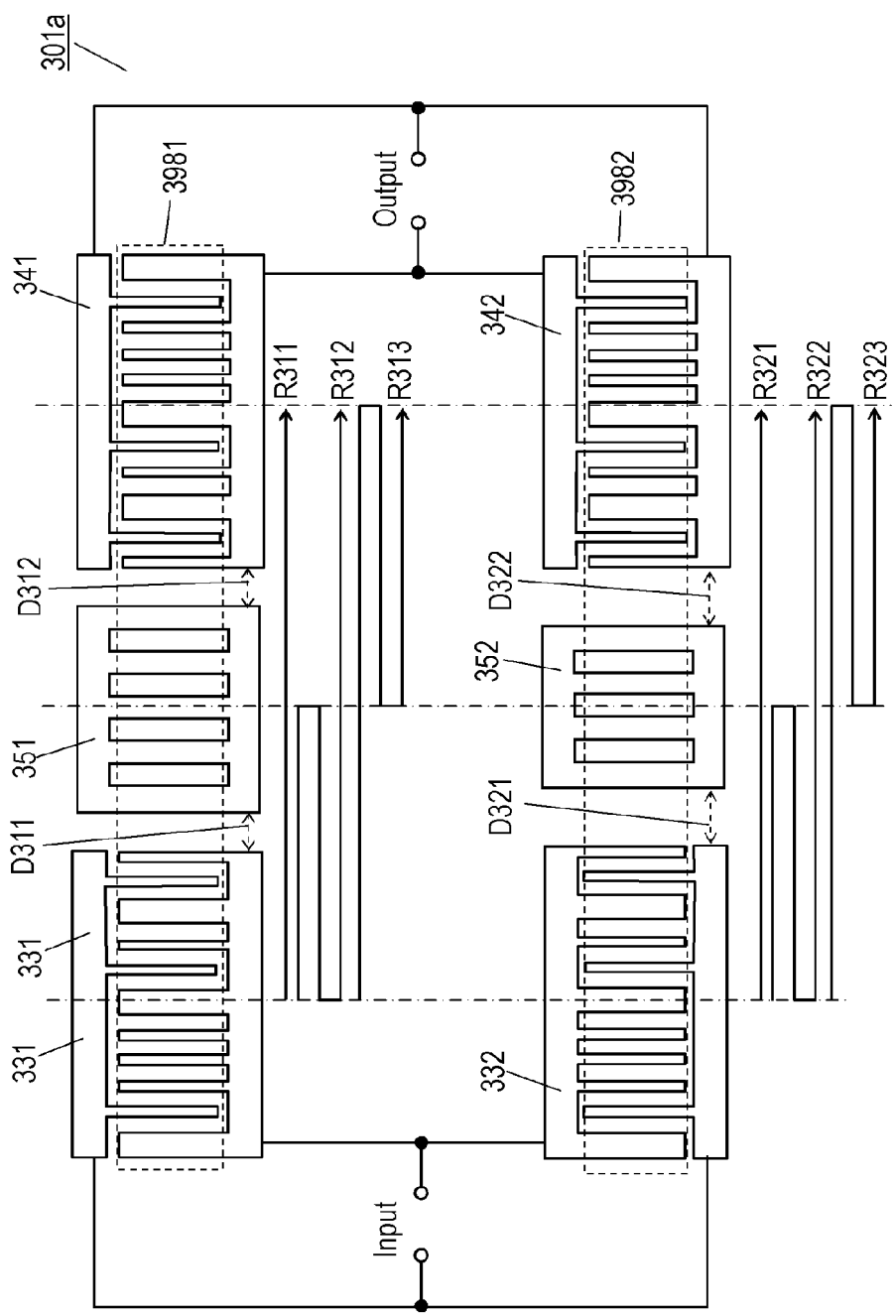
FIG. 19 is a schematic view of the acoustic wave element shown in FIG. 18 for illustrating an operation of the acoustic wave element.

An operation of acoustic wave element 301a will be described below. FIG. 19 is a schematic top view of acoustic wave element 301a shown in FIG. 18 for illustrating the operation of acoustic wave element 301a, and shows acoustic tracks 3981 and 3982. Acoustic track 3981 is constituted by excitation electrode 331, receiving electrode 341, and reflector 351 that are illustrated in FIG. 18. Acoustic track 3982 is constituted by excitation electrode 332, receiving electrode 342, and reflector 352 that are illustrated in FIG. 18. The number of the electrode fingers of reflector 352 is smaller than the number of the electrode fingers of reflector 351 by one. The distance between excitation electrode 331 and receiving electrode 341 of acoustic track 3981 is equal to the distance between excitation electrode 332 and receiving electrode 342 of acoustic track 3982 along the propagation direction of the main acoustic waves. Further, receiving electrode 341 and receiving electrode 342 are disposed such that a polarity of the comb-shaped electrode of receiving electrode 341 and a polarity of the comb-shaped electrode of receiving electrode 342 are inverted from each other with respect to a direction of potential, so that phase of the signal received by receiving electrode 341 is opposite to the phase of the signal received by receiving electrode 342. Therefore, the signal of main acoustic wave R311 output from receiving electrode 341 and the signal of main acoustic wave R321 output from receiving electrode 342 are added so as to cancel each other.

In acoustic wave element 301a, since the distances along which main acoustic waves R312 and R322 propagate are different from each other by $\lambda/2$, the signal of main acoustic wave R312 output from receiving electrode 341 and the signal of main acoustic wave R322 output from receiving electrode 342 are added so as to strengthen each other, and provide a combined signal with large amplitude. Similarly, since the distances along which main acoustic waves R313 and 323 propagate are different from each other by $\lambda/2$, the signal of main acoustic wave R313 output from receiving electrode 341 and the signal of main acoustic wave R323 output from receiving electrode 342 are added so as to strengthen each other, provide a combined signal with large amplitude. As described above, in acoustic wave element 301a, receiving electrodes 341 and 342 is configured to effectively receive main acoustic waves R312, R322, R313, and R323 that propagate plural times along propagation paths 3991 and 3992. Specifically, main acoustic waves R312, R322, R313, and R323 added so as to strengthen each other pass through sensing portion 305 positioned above propagation paths 3991 and 3992 plural times, and reach receiving electrodes 341 and 342 viewing from above. Therefore, when an object substance or a binding material to be bound with the object substance is attached to sensing portion 305, the characteristics, such as delay time characteristics, of main acoustic waves R312, R322, R313, and R323 change sufficiently, thereby improving sensitivity of sensing portion 305.

Figure 20:
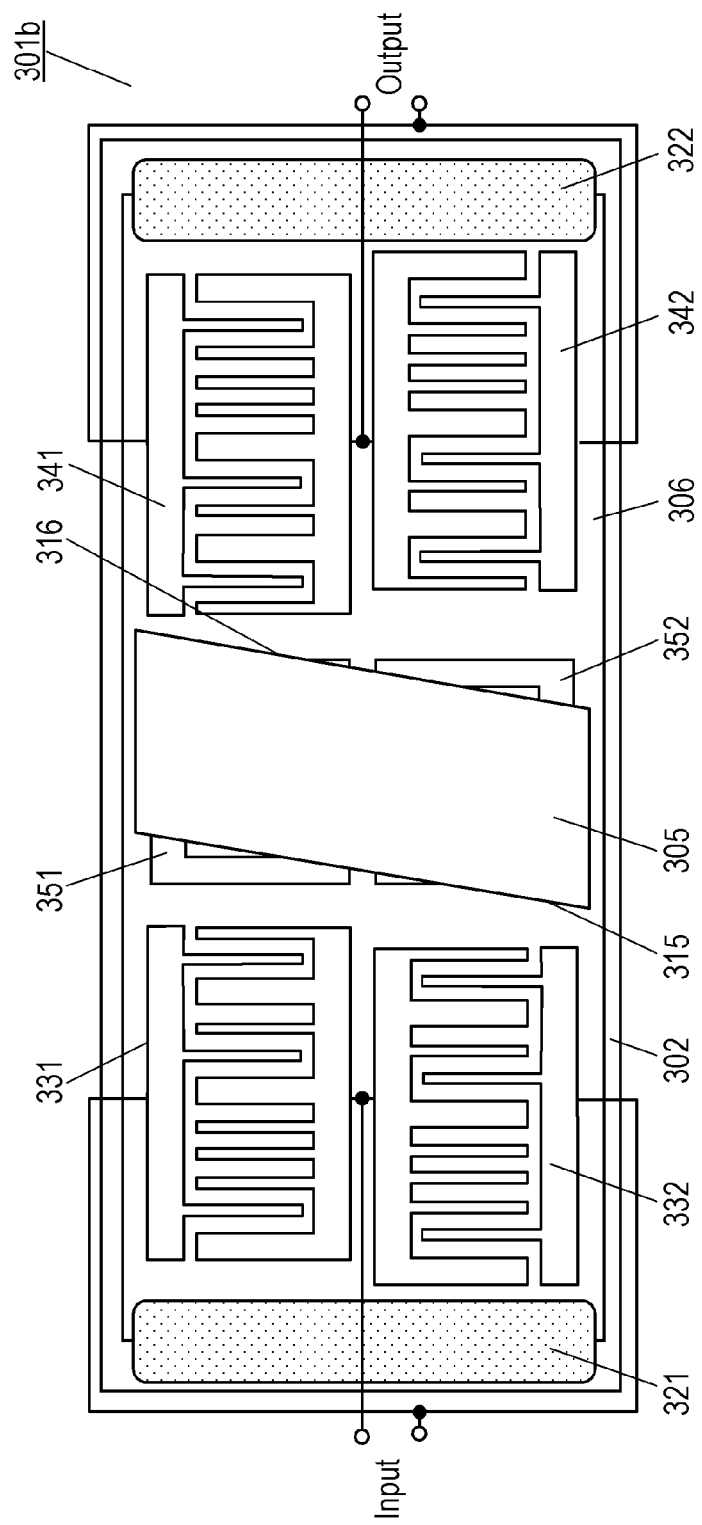
FIG. 20 is a schematic top view of still another acoustic wave element according to Embodiment 3.

FIG. 20 is a schematic top view of still another acoustic wave element 301b according to Embodiment 3. In FIG. 20, components identical to those of acoustic wave element 301 illustrated in FIG. 14A are denoted by the same reference numerals. In acoustic wave elements 301, 301a, and 301b, sensing portion 305 has outer edge 315 facing excitation electrodes 331 and 332 and outer edge 316 facing receiving electrodes 341 and 342. Outer edge 315 of sensing portion 305 is positioned between excitation electrode 331 and receiving electrode 341 while outer edge 316 of sensing portion 305 is positioned between excitation electrode 332 and receiving electrode 342. In acoustic wave element 301b illustrated in FIG. 20, a direction in which outer edges 315 and 316 of sensing portion 305 extend is different from both of a direction in which the electrode fingers of excitation electrodes 331 and 332 extend and a direction in which the electrode fingers of receiving electrodes 341 and 342 extend. A propagation direction along which main acoustic waves output from excitation electrodes 331 and 332 propagate is not perpendicular to the direction in which outer edges 315 and 316 of sensing portion 305 extend and inclines with respect to the direction in which outer edges 315 and 316 of sensing portion 305 extend. This configuration prevents a traveling wave and a reflected wave from cancelling each other due to the main acoustic waves output from excitation electrodes 331 and 332 reflected by outer edge 315 or 316 of sensing portion 305 at 180 degrees in a traveling direction of acoustic waves. As a result, it is possible to improve sensitivity of acoustic wave sensor 361 using acoustic wave element 301b.

Figure 21:
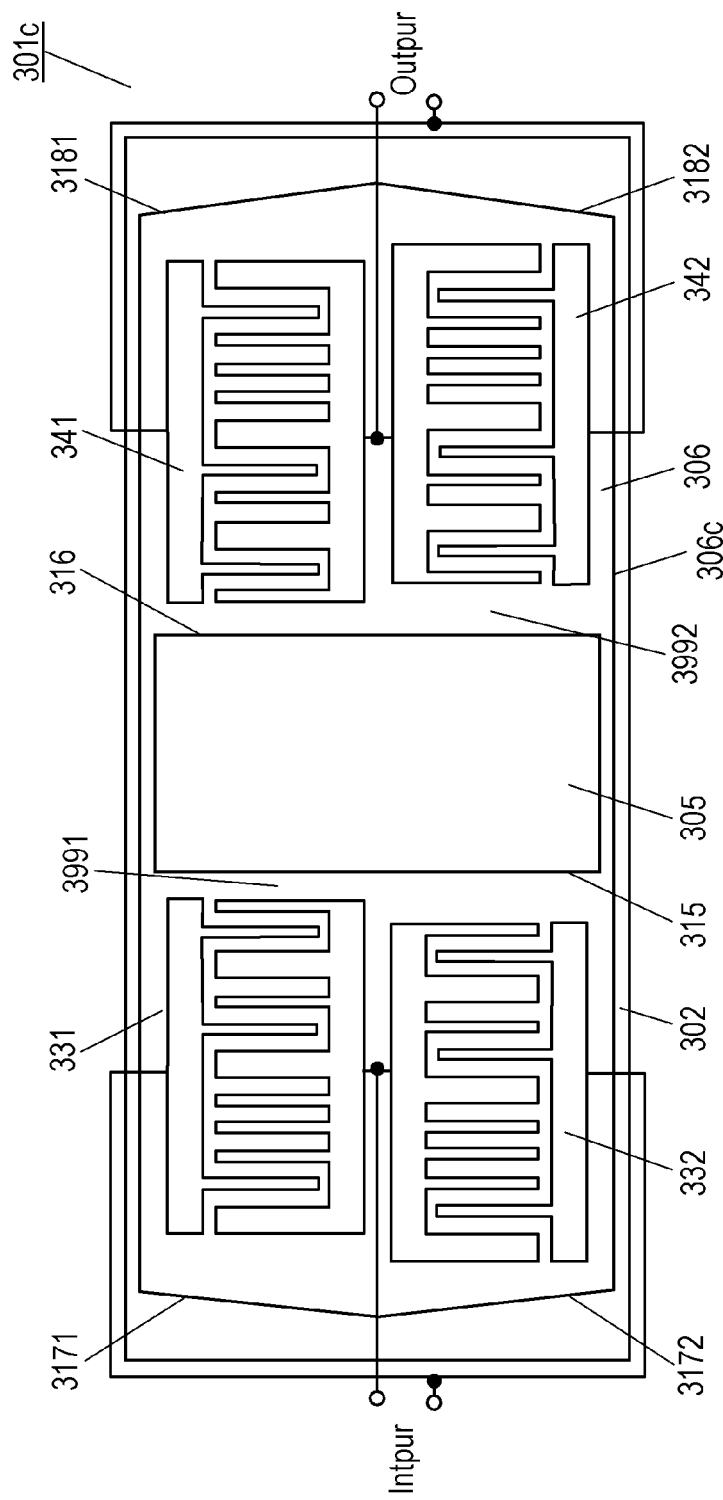
FIG. 21 is a schematic top view of further acoustic wave element according to Embodiment 3.

FIG. 21 is a schematic top view of further acoustic wave element 301c according to Embodiment 3. In FIG. 21, components identical to those of acoustic wave element 301 illustrated in FIG. 14A are denoted by the same reference numerals. Acoustic wave element 301c illustrated in FIG. 21 does not include acoustic absorbents 321 and 322 provided to acoustic wave element 301 illustrated in FIG. 14A. In acoustic wave element 301c illustrated in FIG. 21, outer edge 306c of dielectric layer 306 includes portions 3171, 3172, 3181, and 3182. Portions 3171 and 3172 are positioned opposite to receiving electrodes 341 and 342 with respect to excitation electrodes 331 and 332, respectively. Portions 3181 and 3182 are positioned opposite to excitation electrodes 331 and 332 with respect to receiving electrodes 341 and 342, respectively. Directions in which portions 3171 and 3172 of outer edge 306c of dielectric layer 306 extend are different from the directions in which the electrode fingers of excitation electrodes 331 and 332 extend. Specifically, a propagation direction of unnecessary acoustic waves output from excitation electrodes 331 and 332 is not perpendicular to the directions in which portions 3171 and 3172 of outer edge 306c of dielectric layer 306 extend and inclines with respect to the directions in which portions 3171 and 3172 of outer edge 306c of dielectric layer 306 extend. This configuration can prevent, without providing an acoustic absorbent, unnecessary acoustic waves output by excitation electrodes 331 and 332 from being reflected at 180 degrees by portions 3171 and 3172 of outer edge 306c of dielectric layer 306, and from entering in propagation paths 3991 and 3992 between excitation electrodes 331 and 332 and receiving electrodes 341 and 342. This configuration thus prevents sensitivity of acoustic wave sensor 361 from deteriorating due to unnecessary acoustic waves entering in propagation paths 3991 and 3992.

Further, in acoustic wave element 301c illustrated in FIG. 21, directions in which portions 3181 and 3182 of outer edge 306c of dielectric layer 306 extend may preferably be different from a direction in which the electrode fingers of receiving electrodes 341 and 342 extend, respectively. Specifically, a propagation direction of the acoustic waves that have passed through receiving electrodes 341 and 342 is not perpendicular to the directions in which portions 3181 and 3182 of outer edge 306c of dielectric layer 306 extend and inclines with respect to the directions in which portions 3181 and 3182 of outer edge 306c of dielectric layer 306 extend. This configuration can prevent, without providing an acoustic absorbent, the acoustic waves that have passed through receiving electrodes 341 and 342 from being reflected at 180 degrees by portions 3181 and 3182 of outer edge 306c of dielectric layer 306, and from entering in propagation paths 3991 and 3992 between receiving electrodes 341 and 342 and excitation electrodes 331 and 332. This configuration thus prevents sensitivity of acoustic wave sensor 361 from deteriorating due to unnecessary acoustic waves entering propagation paths 3991 and 3992.

Exemplary Embodiment 4

Figure 22:
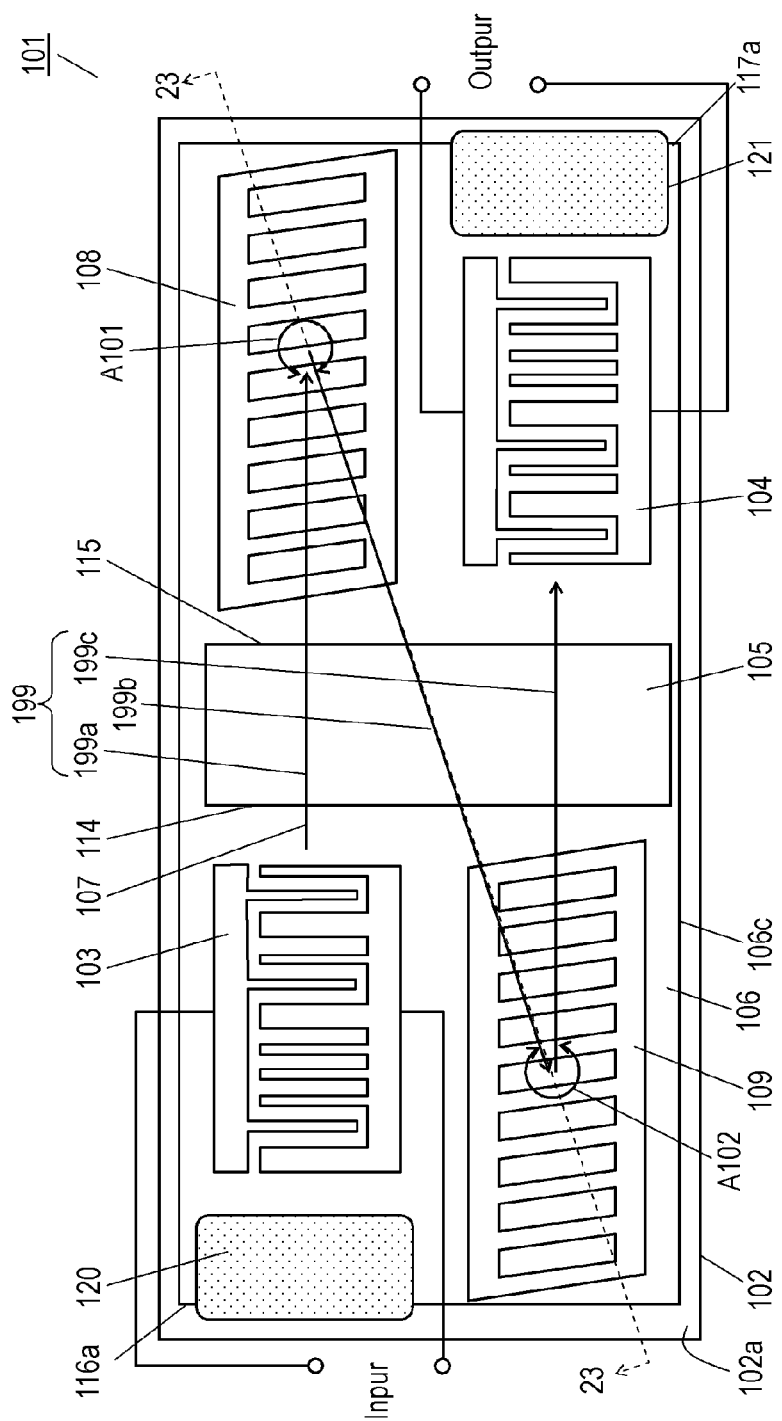
FIG. 22 is a schematic top view of an acoustic wave element according to Exemplary Embodiment 4 of the present invention.

FIG. 22 is a schematic top view of acoustic wave element 101 according to Exemplary Embodiment 4. Acoustic wave element 101 is a transversal type acoustic wave element, and is applicable to a biosensor that senses an object substance, such as a protein, a gene, or a signal molecule, based on a biomolecule recognition mechanism.

Acoustic wave element 101 includes piezoelectric substrate 102, excitation electrode 103 formed on upper surface 102a of piezoelectric substrate 102, reflector 108 formed on upper surface 102a of piezoelectric substrate 102, reflector 109 formed on upper surface 102a of piezoelectric substrate 102, and receiving electrode 104 formed on upper surface 102a of piezoelectric substrate 102. Excitation electrode 103 excites main acoustic wave 107 on upper surface 102a of piezoelectric substrate 102 upon receiving a signal input thereto. Reflector 108 reflects main acoustic wave 107 excited by excitation electrode 103. Reflector 109 reflects main acoustic wave 107 reflected by reflector 108. Receiving electrode 104 receives main acoustic wave 107 reflected by reflector 109, and outputs a signal in response to the received main acoustic wave 107. Upper surface 102a of piezoelectric substrate 102 has thereon propagation path 199 for propagating main acoustic wave 107 from excitation electrode 103 to receiving electrode 104. Propagation path 199 has portion 199a from excitation electrode 103 to reflector 108, portion 199b from reflector 108 to reflector 109, and portion 199c from reflector 109 to receiving electrode 104.

Figure 23:
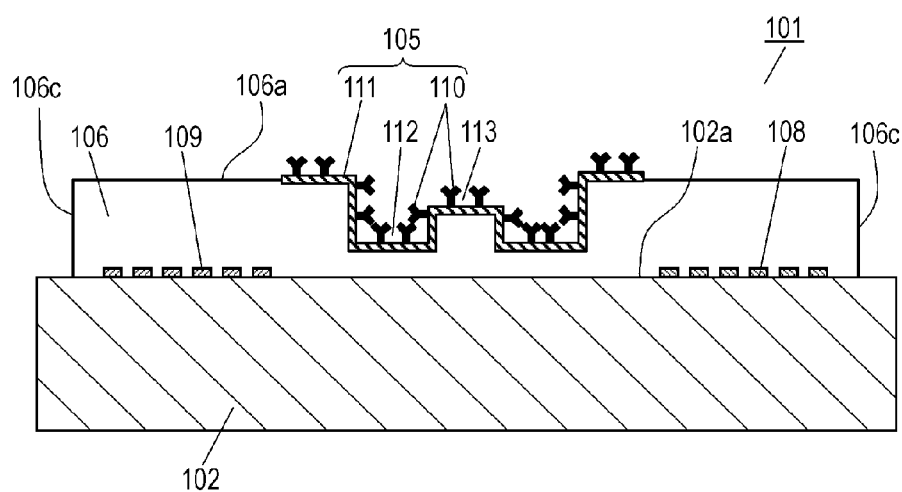
FIG. 23 is a schematic sectional view of the acoustic wave element at line 23-23 shown in FIG. 22.

FIG. 23 is a sectional view of acoustic wave element 101 at line 23-23 along portion 199b of propagation path 199 illustrated in FIG. 22. Acoustic wave element 101 further includes dielectric layer 106 provided on upper surface 102a of piezoelectric substrate 102, and sensing portion 105 provided on upper surface 106a of dielectric layer 106. Dielectric layer 106 covers excitation electrode 103, reflectors 108 and 109, receiving electrode 104, and propagation path 199. Sensing portion 105 is provided on upper surface 106a of dielectric layer 106 above propagation path 199, and reacts to an object substance or a binding material to be bound with the object substance, or allows the object substance or the binding material to be attached thereto.

Acoustic wave element 101 further includes acoustic absorbents 120 and 121 provided on upper surface 102a of piezoelectric substrate 102 and covers outer edge 106c of dielectric layer 106. Acoustic absorbent 120 covers portion 116a of outer edge 106c of dielectric layer 106 opposite to reflector 108 with respect to excitation electrode 103. Acoustic absorbent 121 covers portion 117a of outer edge 106c of dielectric layer 106 opposite to reflector 109 with respect to receiving electrode 104. Acoustic absorbents 120 and 121 are made of a resin, such as an epoxy resin, a silicone resin, an acrylic resin, or a polyimide. Main acoustic wave 107 propagates along propagation path 199 in a propagation direction from excitation electrode 103 to receiving electrode 104 via reflectors 108 and 109 in this order. Unnecessary acoustic waves that propagate from excitation electrode 103 toward a direction opposite to the propagation direction may be produced. Acoustic absorbents 120 and 121 prevent sensitivity of acoustic wave element 101 from deteriorating due to the unnecessary acoustic waves reflected by outer edge 106c of dielectric layer 106 and propagating to excitation electrode 103, and being added to the main acoustic waves. Acoustic absorbents 120 and 121 covering outer edge 106c of dielectric layer 106 absorb the unnecessary acoustic waves and prevent deterioration in sensitivity.

Figure 24:
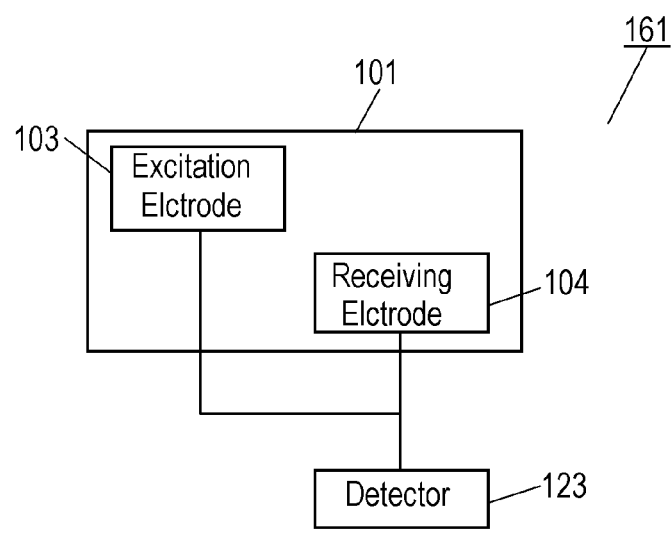
FIG. 24 is a schematic view of the acoustic wave sensor according to Embodiment 4.

FIG. 24 is a schematic view of acoustic wave sensor 161 using acoustic wave element 101. Acoustic wave sensor 161 includes acoustic wave element 101 and detector 123 configured to detect characteristics, such as phase characteristics and frequency characteristics, of main acoustic wave 107 received by receiving electrode 104 based on a signal output from receiving electrode 104 of acoustic wave element 101. Detector 123 is electrically connected to excitation electrode 103.

Acoustic wave element 101 is mounted on a mother board built in an electronic device, such as a medical device. Acoustic wave element 101 may be mounted face down on the mother board such that a surface of piezoelectric substrate 102 having electrodes 103 and 104 are provided thereon faces the mother board. In this case, receiving electrode 104 is electrically connected to detector 123 via, e.g. metal bumps. Alternatively, acoustic wave element 101 may be mounted face up on the mother board such that a surface opposite to the surface having electrodes 103 and 104 provided thereon is bonded to the mother board. In this case, receiving electrode 104 is electrically connected to detector 123 via, e.g. metal wires.

Detector 123 detects a frequency change or a phase change of main acoustic wave 107 received by receiving electrode 104. Detector 123 may detect other changes in the characteristics, such as speed, amplitude, or a wavelength, of main acoustic wave 107.

When a test substance, such as expired air or test liquid, possibly containing an object substance contacts sensing portion 105, detector 123 can detect changes in the characteristics of main acoustic wave 107 due to a change in a physical amount, such as a mass, of sensing portion 105 by attachment of the object substance, and thus sense a presence or a concentration of the object substance, for example.

In conventional acoustic wave element 501 illustrated in FIG. 28, main acoustic wave 507 excited by excitation electrode 503 propagates across sensing portion 505 above a propagation path only once and then reaches receiving electrode 504. Therefore, characteristics, such as delay time characteristics or phase characteristics, of main acoustic wave 507 may not change sufficiently even when an object substance is attached, not ensuring sensitivity of sensing portion 505 of acoustic wave element 501.

In acoustic wave element 101 according to Embodiment 4, main acoustic wave 107 excited by excitation electrode 103 reaches receiving electrode 104 after being reflected by reflectors 108 and 109 and propagating across sensing portion 105 three times along portions 199a to 199c of propagation path 199. Therefore, when the object substance or the binding material to be bound with the object substance is attached to sensing portion 105, the characteristics of main acoustic wave 107 change sufficiently, hence improving sensitivity to the object substance of sensing portion 105 of acoustic wave element 101.

Dielectric layer 106 may preferably be disposed on piezoelectric substrate 102 and cover at least excitation electrode 103, receiving electrode 104, and reflectors 108 and 109. This configuration suppresses corrosion of electrodes 103 and 104 or reflectors 108 and 109 due to a solvent containing the object substance, as well as deterioration of sensitivity of acoustic wave sensor 161 using acoustic wave element 101 subjected to the corrosion. Dielectric layer 106 may preferably cover propagation path 199. Sensing portion 105 may preferably be formed on dielectric layer 106 above propagation path 199. This configuration suppresses reflection of main acoustic wave 107 by outer edges 114 and 115 of sensing portion 105 above propagation path 199 between excitation electrode 103 and reflector 108, between reflector 108 and reflector 109, or between reflector 109 and receiving electrode 104, and improves sensitivity of acoustic wave sensor 161 using acoustic wave element 101.

Components of acoustic wave element 101 will be detailed below.

Piezoelectric substrate 102 is made of a piezoelectric single crystal substrate, such as a crystal, a langasite-based piezoelectric substrate, a lithium niobate-based piezoelectric substrate, a lithium tantalite-based piezoelectric substrate, or a potassium niobate-based piezoelectric substrate.

Each of excitation electrode 103 and receiving electrode 104 is an interdigital transducer (IDT) electrode including a pair of comb-shaped electrodes each including plural electrode fingers that interdigitate with each other, and excites and receives main acoustic wave 107, such as shear-horizontal (SH) waves or Rayleigh waves. Electrodes 103 and 104 are made of, for example, a single metal, such as aluminum, copper, silver, gold, titanium, tungsten, platinum, molybdenum, or chromium, or an alloy mainly containing any of these metals, or may have a laminated structure of these metals.

Excitation electrode 103 may preferably be a unidirectional electrode that allows main acoustic wave 107 to propagate in a direction toward reflector 108 more efficiently than any direction other than the direction toward reflector 108. Receiving electrode 104 may preferably be a unidirectional electrode that receive main acoustic wave 107 in a direction from reflector 109 more efficiently than any direction other then the direction from reflector 109. This configuration can improve sensitivity of acoustic wave sensor 161 using acoustic wave element 101.

Each of reflectors 108 and 109 is a grating reflector including plural electrode fingers extending in parallel to each other, and reflects main acoustic wave 107 excited by excitation electrode 103. Reflectors 108 and 109 are made of, for example, a single metal, such as aluminum, copper, silver, gold, titanium, tungsten, platinum, molybdenum, or chromium, or an alloy mainly containing these metals, or may have a laminated structure of these metals.

Main acoustic wave 107 is output from excitation electrode 103 and propagates along portion 199a of propagation path 199 to reflector 108. Main acoustic wave 107 reflected by reflector 108 propagates along portion 199b of propagation path 199. The electrode fingers of reflector 108 are disposed such that angle A101 between a propagation direction of main acoustic wave 107 output from excitation electrode 103 and input to reflector 108 and a propagation direction of main acoustic wave 107 reflected by reflector 108 is larger than 155 degrees and smaller than 180 degrees. Specifically, an angle between a direction in which the electrode fingers of excitation electrode 103 extend and a direction in which the electrode fingers of reflector 108 extend is larger than 0 degrees and smaller than 12.5 degrees.

The electrode fingers of reflector 109 are disposed such that angle A102 between a propagation direction of main acoustic wave 107 output from reflector 108 and input to reflector 109 and a propagation direction of main acoustic wave 107 reflected by reflector 109 and input to receiving electrode 104 is larger than 155 degrees and smaller than 180 degrees. Specifically, an angle between a direction in which the electrode fingers of receiving electrode 104 extend and a direction in which the electrode fingers of reflector 109 extend is larger than 0 degrees and smaller than 12.5 degrees.

As described above, propagation path 199 of main acoustic wave 107 output from excitation electrode 103 and input to receiving electrode 104 via reflectors 108 and 109 has a zigzag shape having a "Z"-shape. Portion 199a of propagation path 199 between excitation electrode 103 and reflector 108 is substantially parallel with portion 199c of propagation path 199 between reflector 109 and receiving electrode 104. Main acoustic wave 107 propagates through portions 199a and 199c of propagation path 199 in directions parallel to each other and opposite from each other.

Sensing portion 105 includes antibodies 110 and adhesion layer 111 bonding antibodies 110 to a surface of piezoelectric substrate 102 or a surface of dielectric layer 106. Antibodies 110 react to an object substance or a binding material to be bound with the object substance that may possibly contained in a test substance, such as expired air. Adhesion layer 111 is made of an adhesive material, such as a metal or an organic substance. Antibodies 110 may be directly attached to piezoelectric substrate 102 or dielectric layer 106 without adhesion layer 111 between antibody 110 and piezoelectric substrate 102 or dielectric layer 106.

Dielectric layer 106 is made of an inorganic dielectric material, or may be made of a medium, such as silicon oxide (SiO$_2$), having a frequency-temperature coefficient opposite to that of piezoelectric substrate 102. Dielectric layer 106 may cover electrodes 103 and 104 to improve a frequency-temperature characteristic of acoustic wave element 101. Further, dielectric layer 106 may be made of another dielectric material, such as silicon nitride, silicon nitride oxide, aluminum nitride, aluminum oxide, tantalum oxide, tellurium oxide, diamond, or silicone.

As illustrated in FIG. 23, the upper surface of dielectric layer 106 may preferably be uneven having recess 112 and projection 113 provided on an upper surface of adhesion layer 111. The width of recess 112 is wider than a maximum width of antibody 110 to allow antibodies 110 to be provided within recess 112. Recess 112 and projection 113 may be formed by etching predetermined positions of dielectric layer 106 by, e.g. dry etching after dielectric layer 106 is formed on upper surface 102a of piezoelectric substrate 102 by, e.g. sputtering or vapor deposition.

Figure 25:
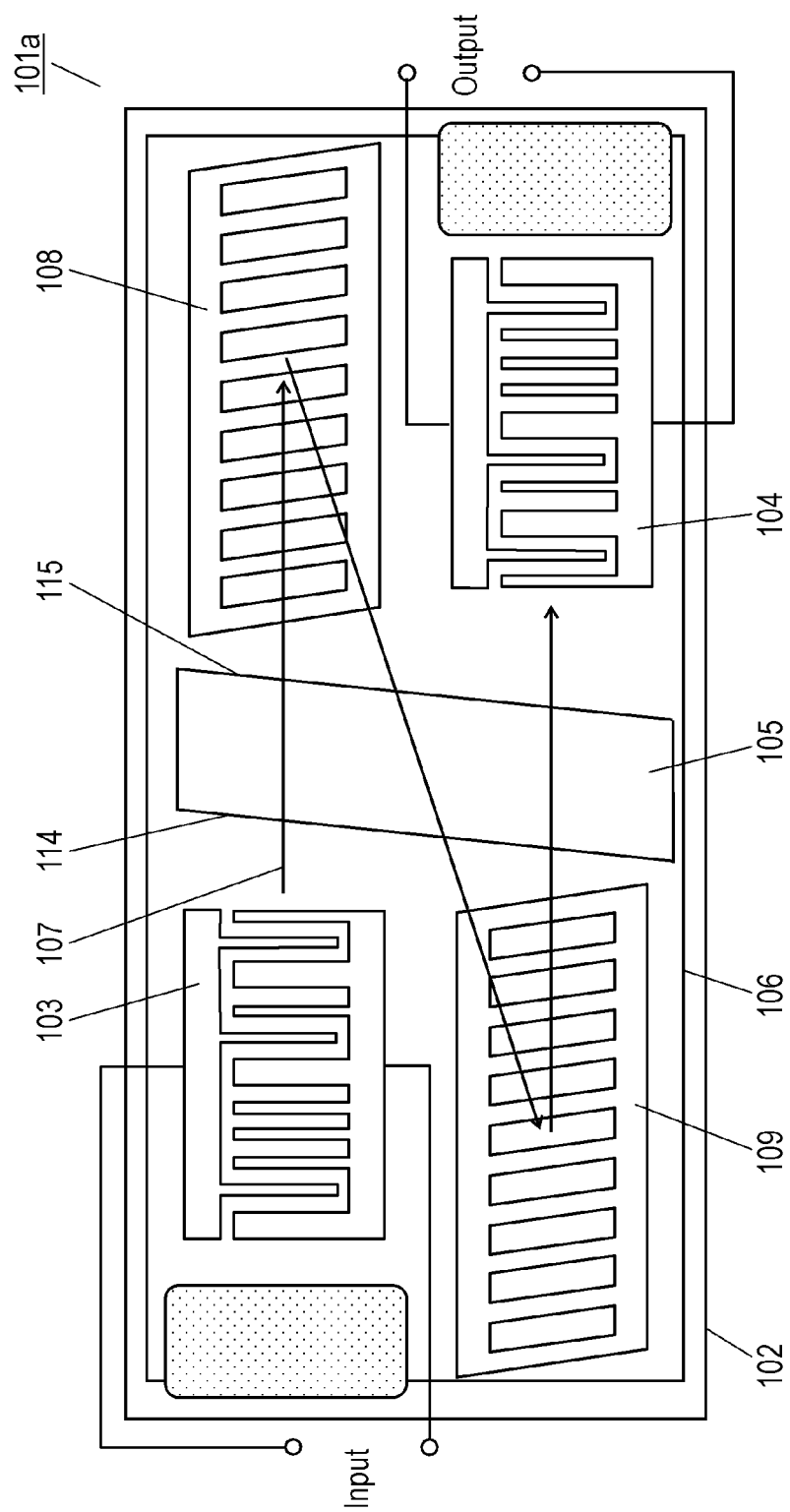
FIG. 25 is a schematic top view of another acoustic wave element according to Embodiment 4.

FIG. 25 is a schematic top view of another acoustic wave element 101a according to Embodiment 4. In FIG. 25, components identical to those of acoustic wave element 101 illustrated in FIG. 22 are denoted by the same reference numerals.

In acoustic wave element 101 illustrated in FIG. 22, a direction in which the electrode fingers of the IDT electrodes of excitation electrode 103 extend is identical to a direction in which outer edges 114 and 115 of sensing portion 105 between excitation electrode 103 and reflector 108 extend. This configuration may cause a traveling wave and a reflected wave to cancel each other due to main acoustic wave 107 output from excitation electrode 103 reflected by outer edge 114 or outer edge 115 of sensing portion 105 at 180 degrees.

In acoustic wave element 101a illustrated in FIG. 25, the direction in which outer edges 114 and 115 of sensing portion 105 between excitation electrode 103 and reflector 108 extend may preferably be different from both of a direction in which the electrode fingers of excitation electrode 103 extend and a direction in which the electrode fingers of reflector 108 extend. Specifically, the direction along which main acoustic wave 107 output from excitation electrode 103 and reflector 108 propagates may not preferably be perpendicular to the direction in which outer edges 114 and 115 of sensing portion 105 extend and may incline with respect to the direction in which outer edges 114 and 115 of sensing portion 105 extend. This configuration prevents a traveling wave and a reflected wave from cancelling each other due to main acoustic wave 107 output from excitation electrode 103 and reflector 108 reflecting upon outer edge 114 or 115 of sensing portion 105 at 180 degrees in a traveling direction of acoustic waves. As a result, it is possible to further improve sensitivity of acoustic wave sensor 161 using acoustic wave element 101a.

Further, in acoustic wave element 101a illustrated in FIG. 25, the direction in which outer edges 114 and 115 of sensing portion 105 between reflector 108 and reflector 109 extend may preferably be different from both of the direction in which the electrode fingers of reflector 108 extend and a direction in which the electrode fingers of reflector 109 extend. Specifically, the propagation direction along which main acoustic wave 107 reflected by reflector 108 propagates may preferably be not perpendicular to the direction in which outer edges 114 and 115 of sensing portion 105 extend and may incline with respect to the direction in which outer edges 114 and 115 of sensing portion 105 extend. This configuration prevents a traveling wave and a reflected wave from cancelling each other due to main acoustic wave 107 reflected by reflector 108 reflecting upon outer edge 114 or 115 of sensing portion 105 at 180 degrees in a traveling direction of acoustic waves. As a result, it is possible to further improve sensing sensitivity of acoustic wave sensor 161 using acoustic wave element 101a.

Moreover, in acoustic wave element 101a illustrated in FIG. 25, it is desirable that the direction in which outer edges 114 and 115 of sensing portion 105 between reflector 109 and receiving electrode 104 extend be different from both of the direction in which the electrode fingers of reflector 109 extend and a direction in which the electrode fingers of receiving electrode 104 extend. Specifically, the propagation direction along which main acoustic wave 107 reflected by reflector 109 propagates be not at a right angle and be inclined with respect to the direction in which the electrode fingers of reflector 109 extend. With this, it is possible to prevent a traveling wave and a reflected wave from cancelling each other due to main acoustic wave 107 reflected by reflector 109 reflecting upon outer edge 114 or 115 of sensing portion 105 at 180 degrees in a traveling direction of acoustic waves. As a result, it is possible to improve sensing sensitivity of acoustic wave sensor 161 using acoustic wave element 101.

Figure 26:
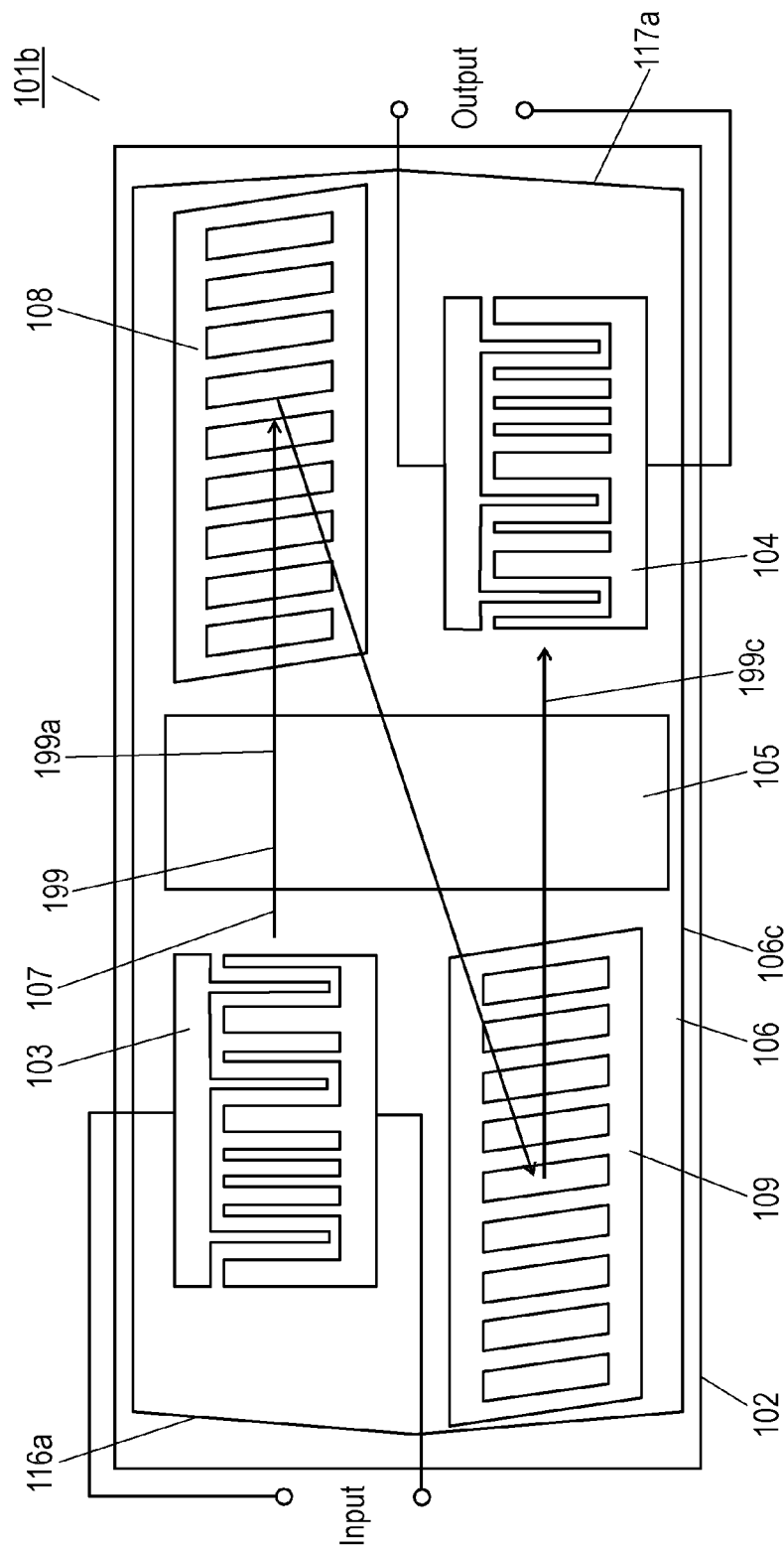
FIG. 26 is a schematic top view of still another acoustic wave element according to Embodiment 4.

FIG. 26 is a schematic top view of still another acoustic wave element 101b according to Embodiment 4. In FIG. 26, components identical to those of acoustic wave element 101 illustrated in FIG. 22 are denoted by the same reference numerals. Acoustic wave element 101b illustrated in FIG. 26 does not include acoustic absorbents 120 and 121 of acoustic wave element 101 illustrated in FIG. 22.

In acoustic wave element 101b illustrated in FIG. 26, a direction in which portion 116a of outer edge 106c of dielectric layer 106 opposite to reflector 108 with respect to excitation electrode 103 extends may preferably be different from the direction in which the electrode fingers of excitation electrode 103 extend. Specifically, a direction along which unnecessary acoustic waves output from excitation electrode 103 propagate may preferably be not perpendicular to the direction in which portion 116a of outer edge 106c of dielectric layer 106 extends and may incline with respect to the direction in which portion 116a of outer edge 106c of dielectric layer 106 extends. In acoustic wave element 101 illustrated in FIG. 22, in the case that acoustic absorbent 120 is not provided, unnecessary acoustic waves output from excitation electrode 103 may be reflected by outer edge 106c of dielectric layer 106 at 180 degrees to enter portion 199a of propagation path 199 between excitation electrode 103 and reflector 108, thus deteriorating sensitivity of acoustic wave sensor 161 using acoustic wave element 101. In acoustic wave element 101b illustrated in FIG. 26, in the case that acoustic absorbent 120 is not provided, unnecessary acoustic waves output from excitation electrode 103 may not enter in portion 199a of propagation path 199 even if being reflected by portion 116a of outer edge 106c of dielectric layer 106 at 180 degrees. Therefore, it is possible to prevent deterioration of sensitivity of acoustic wave sensor 161 using acoustic wave element 101b.

Further, in acoustic wave element 101b illustrated in FIG. 26, a direction in which portion 117a of outer edge 106c of dielectric layer 106 opposite to reflector 109 with respect to receiving electrode 104 extends may preferably be different from the direction in which the electrode fingers of receiving electrode 104 extend. Specifically, a direction along which unnecessary acoustic waves that have passed through receiving electrode 104 propagate may preferably be not perpendicular to the direction in which the electrode fingers of receiving electrode 104 extend and may incline with respect to the direction in which the electrode fingers of receiving electrode 104 extend. In acoustic wave element 101 illustrated in FIG. 22, in the case that acoustic absorbent 121 is not provided, unnecessary acoustic waves that have passed through receiving electrode 104 may be reflected by portion 117a of outer edge 106c of dielectric layer 106 at 180 degrees to enter in portion 199c of propagation path 199 between receiving electrode 104 and reflector 109, and deteriorates sensitivity of acoustic wave sensor 161 using acoustic wave element 101. In acoustic wave element 101b illustrated in FIG. 26, in the case that acoustic absorbent 121 is not provided, acoustic waves that have passed through receiving electrode 104 may neither be reflected by portion 117a of outer edge 106c of dielectric layer 106 at 180 degrees nor enter in portion 199c of propagation path 199. Therefore, it is possible to prevent deterioration of sensitivity of acoustic wave sensor 161 using acoustic wave element 101b.

Figure 27:
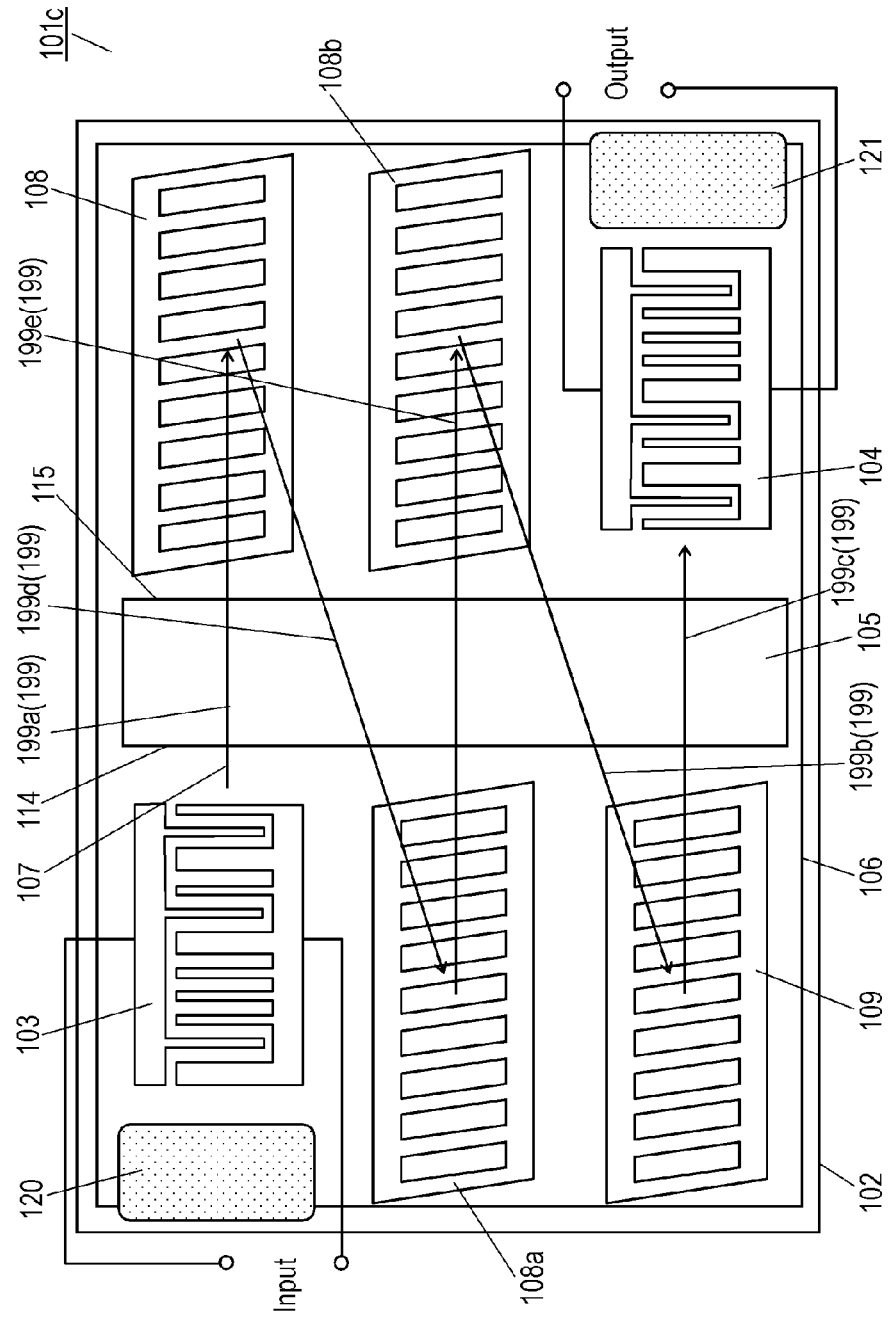
FIG. 27 is a schematic top view of further acoustic wave element according to Embodiment 4.

FIG. 27 is a schematic top view of further acoustic wave element 101c according to Embodiment 4. In FIG. 27, components identical to those of acoustic wave element 101 illustrated in FIG. 22 are denoted by the same reference numerals. Acoustic wave element 101c illustrated in FIG. 27 includes components of acoustic wave element 101 illustrated in FIG. 22, and further includes reflector 108a provided between excitation electrode 103 and reflector 109, and reflector 108b provided between receiving electrode 104 and reflector 108. Viewing from above, reflectors 108a and 108b are disposed such that sensing portion 105 is positioned between reflectors 108a and 108b.

In acoustic wave element 101b illustrated in FIG. 27, propagation path 199 along which main acoustic wave 107 propagates further includes portion 199d from reflector 108 to reflector 108a, and portion 199e from reflector 108a to reflector 108b. Main acoustic wave 107 reflected by reflector 108 propagates along portion 199d of propagation path 199. Main acoustic wave 107 that propagates along portion 199d of propagation path 199 is reflected by reflector 108a. Main acoustic wave 107 reflected by reflector 108a propagates along portion 199e of propagation path 199. Main acoustic wave 107 that propagates along portion 199e of propagation path 199 is reflected by reflector 108b. Main acoustic wave 107 reflected by reflector 108b propagates along portion 199b of propagation path 199. Main acoustic wave 107 that propagates along portion 199b of propagation path 199 is reflected by reflector 109. Main acoustic wave 107 reflected by reflector 109 propagates along portion 199c of propagation path 199. Main acoustic wave 107 that propagates along portion 199c of propagation path 199 is received by receiving electrode 104. Therefore, main acoustic wave 107 propagates between outer edges 114 and 115 of sensing portion 105 five times while propagating along propagation path 199. As a result, when an object substance or a binding material to be bound with the object substance is attached to sensing portion 105, the characteristics of main acoustic wave 107 further change, and can improve sensitivity of sensing portion 105 of acoustic wave element 101. More reflectors may be provided along a path between reflector 108 and reflector 109. The more the number of the reflectors is, the more the number of times main acoustic wave 107 propagating along propagation path 199 propagates between outer edges 114 and 115 of sensing portion 105 increases. As a result, when the object substance or the binding material to be bound with the object substance is attached to sensing portion 105, the characteristics of the main acoustic wave 107 further change, and further improve sensitivity of sensing portion 105 of acoustic wave element 101.

In the embodiments, terms, such as "upper surface" and "above", indicating directions merely indicate relative directions depending on relative positional relations between components, such as the piezoelectric substrate and the electrodes, of the acoustic wave element, and do not indicate absolute directions, such as a vertical direction.

INDUSTRIAL APPLICABILITY

An acoustic wave element according to the present invention and an acoustic wave sensor using the acoustic wave element can improve sensitivity, and is applicable to various electronic devices, such as medical devices.

REFERENCE MARKS IN THE DRAWINGS 101 acoustic wave element
102 piezoelectric substrate
103 excitation electrode (first excitation electrode)
104 receiving electrode (first receiving electrode)
105 sensing portion
106 dielectric layer
108 reflector (first reflector)
109 reflector (second reflector)
111 adhesion layer
201 acoustic wave element
202 piezoelectric substrate
205 sensing portion
206 dielectric layer
211 adhesion layer
231 excitation electrode (first excitation electrode)
232 excitation electrode (second excitation electrode)
233 excitation electrode (third excitation electrode)
241 receiving electrode (first receiving electrode)
242 receiving electrode (second receiving electrode)
243 receiving electrode (third receiving electrode)
301 acoustic wave element
302 piezoelectric substrate
306 dielectric layer
312 adhesion layer
331 excitation electrode (first excitation electrode)
332 excitation electrode (second excitation electrode)
341 receiving electrode (first receiving electrode)
342 receiving electrode (second receiving electrode)
351 reflector (first reflector)
352 reflector (second reflector)
401 acoustic wave element
402 piezoelectric substrate
406 dielectric layer
412 adhesion layer
431 excitation electrode (first excitation electrode)
432 excitation electrode (second excitation electrode)
441 receiving electrode (first receiving electrode)
442 receiving electrode (second receiving electrode)
451 reflector (first reflector)
452 reflector (second reflector)

The invention claimed is:
1. An acoustic wave element comprising:
a piezoelectric substrate having an upper surface;
a first excitation electrode configured to excite and output a first main acoustic wave on the upper surface of the piezoelectric substrate;
a first receiving electrode configured to receive the first main acoustic wave;
a first propagation path configured to allow the first main acoustic wave to propagate along the upper surface of the piezoelectric substrate from the first excitation electrode to the first receiving electrode;
a second excitation electrode configured to excite and output a second main acoustic wave on the upper surface of the piezoelectric substrate;
a second receiving electrode configured to receive the second main acoustic wave;
a second propagation path configured to allow the second main acoustic wave to propagate along the upper surface of the piezoelectric substrate from the second excitation electrode to the second receiving electrode; and
a sensing portion provided above the first propagation path and the second propagation path, and configured to react to an object substance,
wherein the first propagation path is configured such that the first main acoustic wave passes through the sensing portion a plurality of predetermined times along the first propagation path,
wherein the second propagation path is configured such that the second main acoustic wave passes through the sensing portion a plurality of predetermined times along the second propagation path,
wherein the first receiving electrode is configured to output a first signal in response to the received first main acoustic wave,
wherein the second receiving electrode is configured to output a second signal in response to the received second main acoustic wave, and
wherein the first excitation electrode, the second excitation electrode, the first receiving electrode, and the second receiving electrode are disposed such that the first signal and the second signal are added so as to strengthen each other.

2. The acoustic wave element according to claim 1, wherein the sensing portion includes a first outer and a second outer edge, the first outer edge facing the first excitation electrode, the second outer edge facing the first receiving electrode, and
wherein the first propagation path is configured to allow the first main acoustic wave to pass a plurality of times through a region from the first outer edge to the second outer edge of the sensing portion.

3. The acoustic wave element according to claim 1, further comprising:
a third excitation electrode configured to excite and output a third main acoustic wave on the upper surface of the piezoelectric substrate;
a third receiving electrode configured to receive the third main acoustic wave, and output a third signal in response to the received third main acoustic wave; and
a third propagation path configured to allow the third main acoustic wave to propagate along the upper surface of the piezoelectric substrate from the third excitation electrode to the third receiving electrode,
wherein the sensing portion is provided above the first propagation path, the second propagation path, and the third propagation path,
wherein the third propagation path is configured such that the third main acoustic wave passes through the sensing portion a plurality of times along the third propagation path,
wherein the first excitation electrode is configured to excite and output a fourth main acoustic wave on the upper surface of the piezoelectric substrate, the fourth main acoustic wave passing through the sensing portion only once along the first propagation path,
wherein the first receiving electrode is configured to receive the fourth main acoustic wave and output a fourth signal in response to the received fourth main acoustic wave,
wherein the second excitation electrode is configured to excite and output a fifth main acoustic wave on the upper surface of the piezoelectric substrate, the fifth main acoustic wave passing through the sensing portion only once along the second propagation path,
wherein the second receiving electrode is configured to receive the fifth main acoustic wave and output a fifth signal in response to the received fifth main acoustic wave,
wherein the third excitation electrode is configured to excite a sixth main acoustic wave on the upper surface of the piezoelectric substrate, the sixth main acoustic wave passing through the sensing portion only once along the third propagation path,
wherein the third receiving electrode is configured to receive the sixth main acoustic wave and output a sixth signal in response to the received sixth main acoustic wave, and
wherein the first excitation electrode, the second excitation electrode, the third excitation electrode, the first receiving electrode, the second receiving electrode, and the third receiving electrode are disposed such that the fourth signal, the fifth signal, and the sixth signal are added so as to cancel each other, and that the first signal, the second signal, and the third signal are added so as to strengthen each other.

4. The acoustic wave element according to claim 3, wherein the first excitation electrode, the second excitation electrode, and the third excitation electrode are unidirectional electrodes that allow the first main acoustic wave, the second main acoustic wave, and the third main acoustic wave to propagate in directions toward the first receiving electrode, the second receiving electrode, and the third receiving electrode more efficiently than any direction other than the directions toward the first receiving electrode, the second receiving electrode, and the third receiving electrode, respectively, and
wherein the first receiving electrode, the second receiving electrode, and the third receiving electrode are unidirectional electrodes that receive the first main acoustic wave, the second main acoustic wave, and the third main acoustic wave in directions from the first excitation electrode, the second excitation electrode, and the third excitation electrode more efficiently than any direction other than the directions from the first excitation electrode, the second excitation electrode, and the third excitation electrode, respectively.

5. The acoustic wave element according to claim 3, wherein each of the first excitation electrode, the second excitation electrode, and the third excitation electrode is an interdigital transducer (IDT) electrode including a pair of comb-shaped electrodes each including a plurality of electrode fingers that interdigitate with each other,
wherein each of the first receiving electrode, the second receiving electrode, and the third receiving electrode is an IDT electrode including a pair of comb-shaped electrodes each including a plurality of electrode fingers that interdigitate with each other,
wherein the sensing portion includes a first outer edge and a second outer edge, the first outer edge facing the first excitation electrode, the second excitation electrode, and the third excitation electrode, the second outer edge facing the first receiving electrode, the second receiving electrode, and the third receiving electrode, and wherein a direction in which the first outer edge of the sensing portion extends and a direction in which the second outer edge of the sensing portion extends are different from both of a direction in which the plurality of electrode fingers of each of the first excitation electrode, the second excitation electrode, and the third excitation electrode extend and a direction in which the plurality of electrode fingers of each of the first receiving electrode, the second receiving electrode, and the third receiving electrode extend.

6. The acoustic wave element according to claim 3, further comprising a dielectric layer provided on the upper surface of the piezoelectric substrate for covering the first excitation electrode, the second excitation electrode, the third excitation electrode, the first receiving electrode, the second receiving electrode, and the third receiving electrode.

7. The acoustic wave element according to claim 6,
wherein the dielectric layer covers the first excitation electrode, the second excitation electrode, the third excitation electrode, the first receiving electrode, the second receiving electrode, the third receiving electrode, the first propagation path, the second propagation path, and the third propagation path, and
wherein the sensing portion is provided on an upper surface of the dielectric layer and above the first propagation path, the second propagation path, and the third propagation path.

8. The acoustic wave element according to claim 7, wherein the upper surface of the dielectric layer has a recess therein configured to be bound with the object substance.

9. The acoustic wave element according to claim 7,
wherein the sensing portion includes an adhesion layer provided on the upper surface of the dielectric layer, and
wherein an upper surface of the adhesion layer has a recess therein configured to bond to the object substance.

10. The acoustic wave element according to claim 6,
wherein an outer edge of the dielectric layer includes a first portion, a second portion, and a third portion opposite to the first receiving electrode, the second receiving electrode, and the third receiving electrode with respect to the first excitation electrode, the second excitation electrode, and the third excitation electrode, respectively
wherein the first excitation electrode is an interdigital transducer (IDT) electrode including a pair of comb-shaped electrodes each including a plurality of electrode fingers that interdigitate with each other,
wherein the second excitation electrode is an IDT electrode including a pair of comb-shaped electrodes each including a plurality of electrode fingers that interdigitate with each other,
wherein the third excitation electrode is an IDT electrode including a pair of comb-shaped electrodes each including a plurality of electrode fingers that interdigitate with each other, and
wherein a direction in which the first portion of the outer edge of the dielectric layer extends, a direction in which the second portion of the outer edge of the dielectric layer extends, and a direction in which the third portion of the outer edge of the dielectric layer extends are different from a direction in which the plurality of electrode fingers of the first excitation electrode extend, a direction in which the plurality of electrode fingers of the second excitation electrode extend, and a direction in which the plurality of electrode fingers of the third excitation electrode extend, respectively.

11. The acoustic wave element according to claim 6,
wherein an outer edge of the dielectric layer includes a first portion, a second portion, and a third portion opposite to the first excitation electrode, the second excitation electrode, and the third excitation electrode with respect to the first receiving electrode, the second receiving electrode, and the third receiving electrode, respectively,
wherein the first receiving electrode is an interdigital transducer (IDT) electrode including a pair of comb-shaped electrodes each including a plurality of electrode fingers that interdigitate with each other,
wherein the second receiving electrode is an IDT electrode including a pair of comb-shaped electrodes each including a plurality of electrode fingers that interdigitate with each other,
wherein the third receiving electrode is an IDT electrode including a pair of comb-shaped electrodes each having a plurality of electrode fingers that interdigitate with each other, and
wherein a direction in which the first portion of the outer edge of the dielectric layer extends, a direction in which the second portion of the outer edge of the dielectric layer extends, and a direction in which the third portion of the outer edge of the dielectric layer extends are different from a direction in which the plurality of electrode fingers of the first receiving electrode extend, a direction in which the plurality of electrode fingers of the second receiving electrode extend, and a direction in which the plurality of electrode fingers of the third receiving electrode extend, respectively.

12. The acoustic wave element according to claim 1, further comprising:
third to m-th excitation electrodes (m is an odd number not smaller than three);
third to m-th receiving electrodes; and
third to m-th propagation paths from the third to m-th excitation electrodes to the third to m-th receiving electrodes, respectively,
wherein the third to m-th excitation electrodes are configured to excite and output third to m-th main acoustic waves on the upper surface of the piezoelectric substrate, respectively
wherein the third to m-th receiving electrodes are configured to receive the third to m-th main acoustic waves output from the third to m-th excitation electrodes, respectively
wherein the third to m-th propagation paths are configured to allow the third to m-th main acoustic waves to propagate, respectively,
wherein the sensing portion is provided above the first to m-th propagation paths,
wherein the first to m-th main acoustic waves have a wavelength $\lambda$,
wherein two of first to m-th distances which are from the first to m-th excitation electrodes to the first to m-th receiving electrodes, respectively, are different from each other by a difference ranging from $\lambda/m+n\lambda-\lambda/18\cdot(m-1)$ to $\lambda/m+n\cdot\lambda+\lambda/18\cdot(m-1)$ (where n is an integer), and
wherein the third to m-th main acoustic waves pass through the sensing portion a plurality of times along the third to m-th propagation paths, respectively.

13. The acoustic wave element according to claim 1, further comprising:
a first reflector configured to reflect the first main acoustic wave; and
a second reflector configured to reflect the second main acoustic wave;
wherein the first propagation path is provided between the first receiving electrode and the first reflector,
wherein the second propagation path is provided between the second receiving electrode and the second reflector,
wherein the first excitation electrode is configured to excite and output a third main acoustic wave on the upper surface of the piezoelectric substrate, the third main acoustic wave reaching the first receiving electrode without passing through the sensing portion,
wherein the second excitation electrode is configured to excite and output a fourth main acoustic wave on the upper surface of the piezoelectric substrate, the fourth main acoustic wave reaching the second receiving electrode without passing through the sensing portion,
wherein the output first main acoustic wave passes through the first receiving electrode, then, is reflected by the first reflector along the first propagation path, and reaches the first receiving electrode to be received by the first receiving electrode,
wherein the output second main acoustic wave passes through the second receiving electrode, then, is reflected by the first reflector along the second propagation path, and reaches the second receiving electrode to be received by the second receiving electrode,
wherein the first receiving electrode is configured to receive the third main acoustic wave reaching the first receiving electrode and to output a third signal in response to the third main acoustic wave reaching the first receiving electrode,
wherein the second receiving electrode is configured to receive the fourth main acoustic wave reaching the second receiving electrode and to output a fourth signal in response to the fourth main acoustic wave reaching the second receiving electrode, and
wherein the first excitation electrode, the second excitation electrode, the first receiving electrode, the second receiving electrode, the first reflector, and the second reflector are disposed such that the third signal and the fourth signal are added so as to cancel each other, and that the first signal and the second signal are added so as to strengthen each other.

14. The acoustic wave element according to claim 13, wherein the first excitation electrode and the second excitation electrode are unidirectional electrodes that allow the first main acoustic wave and the second main acoustic wave to propagate in directions toward the first receiving electrode and the second receiving electrode more efficiently than any direction other than the directions toward the first receiving electrode and the second receiving electrode, respectively.

15. The acoustic wave element according to claim 13,
wherein the sensing portion includes a first outer edge and a second outer edge, the first outer edge facing the first receiving electrode and the second receiving electrode, the second outer edge facing the first reflector and the second reflector,
wherein each of the first receiving electrode and the second receiving electrode is an interdigital transducer (IDT) electrode including a pair of comb-shaped electrodes each including a plurality of electrode fingers that interdigitate with each other,
wherein each of the first reflector and the second reflector is a grating reflector including a plurality of electrode fingers, and
wherein a direction in which the first outer edge of the sensing portion extends and a direction in which the second outer edge of the sensing portion extends are different from both of a direction in which the plurality of electrode fingers of each of the first receiving electrode and the second receiving electrode extend and a direction in which the plurality of electrode fingers of each of the first reflector and the second reflector extend.

16. The acoustic wave element according to claim 13, further comprising a dielectric layer provided on the upper surface of the piezoelectric substrate for covering at least the first excitation electrode, the second excitation electrode, the first receiving electrode, the second receiving electrode, the first reflector, and the second reflector.

17. The acoustic wave element according to claim 13, further comprising
a dielectric layer provided on the upper surface of the piezoelectric substrate for covering at least the first excitation electrode, the second excitation electrode, the first receiving electrode, the second receiving electrode, the first propagation path, and the second propagation path,
wherein the sensing portion is provided on an upper surface of the dielectric layer and above the first propagation path and the second propagation path.

18. The acoustic wave element according to claim 17, wherein the upper surface of the dielectric layer has a recess therein configured to be bound with the object substance.

19. The acoustic wave element according to claim 17,
wherein the sensing portion includes an adhesion layer provided on the upper surface of the dielectric layer, and
wherein an upper surface of the adhesion layer has a recess configured to be bound with the object substance.

20. The acoustic wave element according to claim 16,
wherein an outer edge of the dielectric layer includes a first portion and a second portion opposite to the first receiving electrode and the second receiving electrode with respect to the first excitation electrode and the second excitation electrode, respectively,
wherein the first excitation electrode is an interdigital transducer (IDT) electrode including a pair of comb-shaped electrodes each including a plurality of electrode fingers that interdigitate with each other,
wherein the second excitation electrode is an IDT electrode including a pair of comb-shaped electrodes each including a plurality of electrode fingers that interdigitate with each other, and
wherein a direction in which the first portion of the outer edge of the dielectric layer extends and a direction in which the second portion of the outer edge of the dielectric layer extends are different from a direction in which the plurality of electrode fingers of the first excitation electrode extend and a direction in which the plurality of electrode fingers of the second excitation electrode extend, respectively.

21. The acoustic wave element according to claim 16,
wherein an outer edge of the dielectric layer includes a first portion and a second portion opposite to the first receiving electrode and the second receiving electrode with respect to the first reflector and the second reflector, respectively, wherein each of the first reflector and the second reflector is a grating reflector including a plurality of electrode fingers, and wherein a direction in which the first portion of the outer edge of the dielectric layer extends and a direction in which the second portion of the outer edge of the dielectric layer extends are different from a direction in which the plurality of electrode fingers of the first reflector extend and a direction in which the plurality of electrode fingers of the second reflector extend, respectively.

22. The acoustic wave element according to claim 17, wherein an outer edge of the dielectric layer includes a first portion and a second portion opposite to the first receiving electrode and the second receiving electrode with respect to the first excitation electrode and the second excitation electrode, respectively, wherein the first excitation electrode is an interdigital transducer (IDT) electrode including a pair of comb-shaped electrodes each including a plurality of electrode fingers that interdigitate with each other, wherein the second excitation electrode is an IDT electrode including a pair of comb-shaped electrodes each including a plurality of electrode fingers that interdigitate with each other, and wherein a direction in which the first portion of the outer edge of the dielectric layer extends and a direction in which the second portion of the outer edge of the dielectric layer extends are different from a direction in which the plurality of electrode fingers of the first excitation electrode extend and a direction in which the plurality of electrode fingers of the second excitation electrode extend, respectively.

23. The acoustic wave element according to claim 17, wherein an outer edge of the dielectric layer includes a first portion and a second portion opposite to the first receiving electrode and the second receiving electrode with respect to the first reflector and the second reflector, respectively, wherein each of the first reflector and the second reflector is a grating reflector including a plurality of electrode fingers, and wherein a direction in which the first portion of the outer edge of the dielectric layer extends and a direction in which the second portion of the outer edge of the dielectric layer extends are different from a direction in which the plurality of electrode fingers of the first reflector extend and a direction in which the plurality of electrode fingers of the second reflector extend, respectively.

24. The acoustic wave element according to claim 13, further comprising a shield electrode provided between each of the first excitation electrode and the second excitation electrode and each of the first receiving electrode and the second receiving electrode.

25. The acoustic wave element according to claim 1, further comprising:

a first reflector provided on the first propagation path; and a second reflector provided on the second propagation path, wherein the first excitation electrode is configured to excite a third main acoustic wave on the upper surface of the piezoelectric substrate, the third main acoustic wave reaching the first receiving electrode after passing through the sensing portion only once along the first propagation path, wherein the second excitation electrode is configured to excite a fourth main acoustic wave on the upper surface of the piezoelectric substrate, the fourth main acoustic wave reaching the second receiving electrode after passing through the sensing portion only once along the third propagation path, wherein the first receiving electrode is configured to receive the third main acoustic wave and to output a third signal in response to the received third main acoustic wave, wherein the second receiving electrode is configured to receive the fourth main acoustic wave and to output a fourth signal in response to the received fourth main acoustic wave, wherein the first excitation electrode, the second excitation electrode, the first receiving electrode, the second receiving electrode, the first reflector, and the second reflector are disposed such that the third signal and the fourth signal are added so as to cancel each other, and that the first signal and the second signal are added so as to strengthen each other.

26. The acoustic wave element according to claim 25, wherein the first excitation electrode and the second excitation electrode are unidirectional electrodes that allow the first main acoustic wave and the second main acoustic wave to propagate in directions toward the first receiving electrode and the second receiving electrode more efficiently than any direction other than the directions toward the first receiving electrode and the second receiving electrode, respectively, and wherein the first receiving electrode and the second receiving electrode are unidirectional electrodes that receive the first main acoustic waves-wave and the second main acoustic wave in directions from the first excitation electrode and the second excitation electrode more efficiently than any direction other than the directions from the first excitation electrode and the second excitation electrode, respectively.

27. The acoustic wave element according to claim 25, wherein the sensing portion includes a first outer edge and a second outer edge, the first outer edge facing the first excitation electrode and the second excitation electrode, the second outer edge facing the first receiving electrode and the second receiving electrode, wherein each of the first excitation electrode and the second excitation electrode is an interdigital transducer (IDT) electrode including a pair of comb-shaped electrodes each including a plurality of electrode fingers that interdigitate with each other, wherein each of the first receiving electrode and the second receiving electrode is an IDT electrode including a pair of comb-shaped electrodes each including a plurality of electrode fingers that interdigitate with each other, and wherein a direction in which the first outer edge of the sensing portion extends and a direction in which the second outer edge of the sensing portion extends are different from both of a direction in which the pluralities of electrode fingers of the first excitation electrode and the second excitation electrode extend and a direction in which the plurality of electrode fingers of the first receiving electrode and the second receiving electrode extend, respectively.

28. The acoustic wave element according to claim 25, further comprising a dielectric layer provided on the upper surface of the piezoelectric substrate for covering at least the first excitation electrode, the second excitation electrode, the first receiving electrode, the second receiving electrode, the first reflector, and the second reflector.

29. The acoustic wave element according to claim 28,
wherein the dielectric layer covers the first excitation electrode, the second excitation electrode, the first receiving electrode, the second receiving electrode, the first propagation path, and the second propagation path, and
wherein the sensing portion is provided on an upper surface of the dielectric layer and above the first propagation path and the second propagation path.

30. The acoustic wave element according to claim 29, wherein the upper surface of the dielectric layer has a recess therein configured to be bound with the object substance.

31. The acoustic wave element according to claim 29,
wherein the sensing portion includes an adhesion layer provided on the upper surface of the dielectric layer, and
wherein an upper surface of the adhesion layer has a recess therein configured to be bound with the object substance.

32. The acoustic wave element according to claim 28,
wherein an outer edge of the dielectric layer includes a first portion and a second portion opposite to the first receiving electrode and the second receiving electrode with respect to the first excitation electrode and the second excitation electrode, respectively,
wherein the first excitation electrode is an interdigital transducer (IDT) electrode including a pair of comb-shaped electrodes each including a plurality of electrode fingers that interdigitate with each other,
wherein the second excitation electrode is an IDT electrode including a pair of comb-shaped electrodes each including a plurality of electrode fingers that interdigitate with each other, and
wherein a direction in which the first portion of the outer edge of the dielectric layer extends and a direction in which the second portion of the outer edge of the dielectric layer extends are different from a direction in which the plurality of electrode fingers of the first excitation electrode extend and a direction in which the plurality of electrode fingers of the second excitation electrode extend, respectively.

33. The acoustic wave element according to claim 28,
wherein an outer edge of the dielectric layer includes a first portion and a second portion opposite to the first excitation electrode and the second excitation electrode with respect to the first receiving electrode and the second receiving electrode, respectively,
wherein the first receiving electrode is an interdigital transducer (IDT) electrode including a pair of comb-shaped electrodes each including a plurality of electrode fingers that interdigitate with each other,
wherein the second receiving electrode is an IDT electrode including a pair of comb-shaped electrodes each including a plurality of electrode fingers that interdigitate with each other, and
wherein a direction in which the first portion of the outer edge of the dielectric layer extends and a direction in which the second portion of the outer edge of the dielectric layer extends are different from a direction in which the plurality of electrode fingers of the first receiving electrode extend and a direction in which the plurality of electrode fingers of the second receiving electrode extend, respectively.

34. An acoustic wave sensor comprising:
the acoustic wave element according to claim 1; and
a detector configured to detect a characteristic of the first main acoustic wave received by the receiving electrodes.

35. An acoustic wave element comprising:
a piezoelectric substrate having an upper surface;
an excitation electrode configured to excite and output a main acoustic wave on the upper surface of the piezoelectric substrate;
a first reflector configured to reflect the main acoustic wave output from the excitation electrode;
a second reflector configured to reflect the main acoustic wave reflected by the first reflector;
a receiving electrode configured to receive the main acoustic wave reflected by the second reflector;
a propagation path configured to allow the main acoustic wave to propagate along the upper surface of the piezoelectric substrate from the excitation electrode to the receiving electrode via the first reflector and the second reflector; and
a sensing portion provided above the propagation path, and configured to react to an object substance,
wherein the propagation path is configured to allow the main acoustic wave to pass through the sensing portion a plurality of times.

36. The acoustic wave element according to claim 35,
wherein the sensing portion includes a first outer edge and a second outer edge, the first outer edge facing the excitation electrode, the second outer edge facing the receiving electrode, and
wherein the propagation path is configured to allow the main acoustic wave to pass a plurality of times through a region from the first outer edge to the second outer edge of the sensing portion.

37. The acoustic wave element according to claim 35,
wherein the excitation electrode is a unidirectional electrode that allows the main acoustic wave to propagate in a direction toward the first reflector more efficiently than any direction other than the direction toward the first reflector, and
wherein the receiving electrode is a unidirectional electrode that receives the main acoustic wave in a direction from the second reflector more efficiently than any direction other than the direction from the second reflector.

38. The acoustic wave element according to claim 35,
wherein the sensing portion includes a first outer edge and a second outer edge, the first outer edge facing the excitation electrode, the second outer edge facing the first reflector,
wherein the excitation electrode is an interdigital transducer (IDT) electrode including a pair of comb-shaped electrodes each including a plurality of electrode fingers that interdigitate with each other,
wherein the first reflector is a grating reflector including a plurality of electrode fingers, and
wherein a direction in which the first outer edge of the sensing portion extends and a direction in which the second outer edge of the sensing portion extends are different from both of a direction in which the plurality of electrode fingers of the excitation electrode extend and a direction in which the plurality of electrode fingers of the first reflector extend.

39. The acoustic wave element according to claim 35,
wherein the propagation path includes a portion from the excitation electrode to the first reflector, wherein the sensing portion includes a first outer edge and a second outer edge, the first outer edge facing the excitation electrode, the second outer edge facing the first reflector, and wherein a direction in which the first outer edge of the sensing portion extends and a direction in which the second outer edge of the sensing portion extends incline with respect to the portion of the propagation path.

40. The acoustic wave element according to claim 35, wherein the first reflector is a grating reflector including a plurality of electrode fingers, wherein the second reflector is a grating reflector including a plurality of electrode fingers, wherein the sensing portion includes a first outer edge and a second outer edge, the first outer edge facing the first reflector, the second outer edge facing the second reflector, and wherein a direction in which the first outer edge of the sensing portion extends and a direction in which the second outer edge of the sensing portion extends are different from both of a direction in which the plurality of electrode fingers of the first reflector extend and a direction in which the plurality of electrode fingers of the second reflector extend.

41. The acoustic wave element according to claim 35, wherein the propagation path includes a portion from the first reflector to the second reflector, wherein the sensing portion includes a first outer edge and a second outer edge, the first outer edge facing the first reflector, the second outer edge facing the second reflector, and wherein a direction in which the first outer edge of the sensing portion extends and a direction in which the second outer edge of the sensing portion extends incline with respect to the portion of the propagation path.

42. The acoustic wave element according to claim 35, wherein the receiving electrode is an interdigital transducer (IDT) electrode including a pair of comb-shaped electrodes each including a plurality of electrode fingers that interdigitate with each other, wherein the second reflector is a grating reflector including a plurality of electrode fingers, wherein the sensing portion includes a first outer edge and a second outer edge, the first outer edge facing the receiving electrode, the second outer edge facing the second reflector, and wherein a direction in which the first outer edge of the sensing portion extends and a direction in which the second outer edge of the sensing portion extends are different from both of a direction in which the plurality of electrode fingers of the receiving electrode extend and a direction in which the plurality of electrode fingers of the second reflector extend.

43. The acoustic wave element according to claim 35, wherein the propagation path includes a portion from the second reflector to the receiving electrode, wherein the sensing portion includes a first outer edge and a second outer edge, the first outer edge facing the receiving electrode, the second outer edge facing the second reflector, and wherein a direction in which the first outer edge of the sensing portion extends and a direction in which the second outer edge of the sensing portion extends incline with respect to the portion of the propagation path.

44. The acoustic wave element according to claim 35, further comprising a dielectric layer provided on the upper surface of the piezoelectric substrate for covering the excitation electrode, the receiving electrode, the first reflector, and the second reflector.

45. The acoustic wave element according to claim 44, wherein the dielectric layer further covers the propagation path, and wherein the sensing portion is provided on an upper surface of the dielectric layer.

46. The acoustic wave element according to claim 45, wherein the upper surface of the dielectric layer has a recess therein configured to be bound with the object substance.

47. The acoustic wave element according to claim 45, wherein the sensing portion includes an adhesion layer provided on the upper surface of the dielectric layer, and wherein the adhesion layer has an upper surface having a recess therein configured to be bound with the object substance.

48. The acoustic wave element according to claim 44, wherein the dielectric layer has an outer edge opposite to the first reflector with respect to the excitation electrode, wherein the excitation electrode is an interdigital transducer (IDT) electrode including a pair of comb-shaped electrodes each including a plurality of electrode fingers that interdigitate with each other, and wherein a direction in which the outer edge of the dielectric layer extends is different from a direction in which the plurality of electrode fingers of the excitation electrode extend.

49. The acoustic wave element according to claim 44, wherein the dielectric layer has an outer edge opposite to the second reflector with respect to the receiving electrode, wherein the receiving electrode is an interdigital transducer (IDT) electrode including a pair of comb-shaped electrodes each including a plurality of electrode fingers that interdigitate with each other, and wherein a direction in which the outer edge of the dielectric layer extends is different from a direction in which the plurality of electrode fingers of the receiving electrode extend.

50. An acoustic wave sensor comprising:

the acoustic wave element according to claim 35; and a detector configured to detect a characteristic of the main acoustic wave received by the receiving electrode.

* * * * *